(12) United States Patent
Hain et al.

(10) Patent No.: US 9,370,183 B2
(45) Date of Patent: Jun. 21, 2016

(54) **USE OF ALS INHIBITOR HERBICIDES FOR CONTROL OF UNWANTED VEGETATION IN ALS INHIBITOR HERBICIDE TOLERANT *BRASSICA*, SUCH AS *B. NAPUS*, PLANTS**

(75) Inventors: Ruediger Hain, Frankfurt (DE); Gerhard Johann, Burscheid (DE); Udo Bickers, Kelkheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/115,056

(22) PCT Filed: May 4, 2012

(86) PCT No.: PCT/EP2012/058232
§ 371 (c)(1),
(2), (4) Date: Jan. 30, 2014

(87) PCT Pub. No.: WO2012/150333
PCT Pub. Date: Nov. 8, 2012

(65) Prior Publication Data
US 2014/0135219 A1    May 15, 2014

Related U.S. Application Data

(60) Provisional application No. 61/483,096, filed on May 6, 2011.

(30) Foreign Application Priority Data

May 4, 2011    (DE) .................................... 11164770

(51) Int. Cl.
| A01N 47/36 | (2006.01) |
| A01N 43/40 | (2006.01) |
| A01N 43/48 | (2006.01) |
| A01N 43/653 | (2006.01) |
| A01N 43/66 | (2006.01) |
| A01N 43/50 | (2006.01) |
| A01N 43/54 | (2006.01) |
| A01N 47/38 | (2006.01) |
| A01N 43/90 | (2006.01) |

(52) U.S. Cl.
CPC ................ *A01N 43/66* (2013.01); *A01N 43/50* (2013.01); *A01N 43/54* (2013.01); *A01N 43/90* (2013.01); *A01N 47/36* (2013.01); *A01N 47/38* (2013.01)

(58) Field of Classification Search
None
See application file for complete search history.

(56) References Cited

U.S. PATENT DOCUMENTS

| 2,556,664 A | 6/1951 | Smith et al. |
| 2,695,225 A | 11/1954 | Witman |
| 2,696,225 A | 11/1954 | Witman |
| 2,903,478 A | 9/1959 | Lambrech |
| 2,913,327 A | 11/1959 | Tilles et al. |
| 3,120,434 A | 2/1964 | Pohland |
| 3,175,887 A | 3/1965 | Van Den Berg |
| 3,175,897 A | 3/1965 | Tilles et al. |
| 3,177,061 A | 4/1965 | Metivier et al. |
| 3,330,821 A | 7/1967 | Harman et al. |
| 3,442,945 A | 5/1969 | Olin et al. |
| 3,480,671 A | 11/1969 | Tilles et al. |
| 3,534,098 A | 10/1970 | Horrom et al. |
| 3,582,314 A | 6/1971 | Konnai et al. |
| 3,692,820 A | 9/1972 | Boroschewski et al. |
| 3,746,532 A | 7/1973 | Kimura et al. |
| 3,836,524 A | 9/1974 | Pitt |
| 3,852,314 A | 12/1974 | Hamanaka et al. |
| 3,894,078 A | 7/1975 | Fridinger |
| 3,937,730 A | 2/1976 | Vogel et al. |
| 3,952,056 A | 4/1976 | Vogel et al. |
| 4,127,405 A | 11/1978 | Levitt |
| 4,288,244 A | 9/1981 | Kirino et al. |
| 4,385,927 A | 5/1983 | Takematsu et al. |
| 4,394,506 A | 7/1983 | Levitt |
| 4,400,196 A | 8/1983 | Albrecht et al. |
| 4,420,325 A | 12/1983 | Sauers |
| 4,479,821 A | 10/1984 | Meyer et al. |
| 4,509,971 A | 4/1985 | Forster et al. |
| 4,551,531 A | 11/1985 | Meyer et al. |
| 4,593,104 A | 6/1986 | Eicken et al. |
| 4,601,747 A | 7/1986 | Willms et al. |
| 4,666,502 A | 5/1987 | Seckinger et al. |
| 4,668,277 A | 5/1987 | Yamamoto et al. |
| 4,671,819 A | 6/1987 | Meyer et al. |

(Continued)

FOREIGN PATENT DOCUMENTS

| CN | 1080116 | 1/1994 |
| DE | 1014380 | 8/1957 |

(Continued)

OTHER PUBLICATIONS

International Search Report for PCT/EP2012/058232 Mailed Aug. 8, 2012.

(Continued)

*Primary Examiner* — Alton Pryor
(74) *Attorney, Agent, or Firm* — McBee Moore Woodward Vanik IP, LLC

(57) ABSTRACT

The present invention relates to the use of the ALS inhibitor herbicides for controlling unwanted vegetation in ALS inhibitor herbicide tolerant *Brassica* plants, more especially, the present invention relates to the use of ALS inhibitor herbicides for control of unwanted vegetation in *Brassica* growing areas which *Brassica* plants comprise non-transgenic mutations of their endogenous acetolactate synthase (ALS) genes I and III.

12 Claims, 6 Drawing Sheets

(56) References Cited

U.S. PATENT DOCUMENTS

| | | |
|---|---|---|
| 4,718,937 A | 1/1988 | Willms et al. |
| 4,746,353 A | 5/1988 | Levitt |
| 4,789,393 A | 12/1988 | Hanagan |
| 4,802,907 A | 2/1989 | Takematsu et al. |
| 4,906,285 A | 3/1990 | Wada et al. |
| 4,908,467 A | 3/1990 | Meyer et al. |
| 4,932,999 A | 6/1990 | Saito et al. |
| 4,952,726 A | 8/1990 | Meyer et al. |
| 4,968,342 A | 11/1990 | Foerster et al. |
| 5,009,699 A | 4/1991 | Brady et al. |
| 5,090,991 A | 2/1992 | Foerster et al. |
| 5,118,339 A | 6/1992 | Tamaru et al. |
| 5,198,599 A | 3/1993 | Thill |
| 5,209,771 A | 5/1993 | Meyer |
| 5,332,717 A | 7/1994 | Luthy et al. |
| 5,378,824 A | 1/1995 | Bedbrook et al. |
| 5,428,002 A | 6/1995 | Luthy et al. |
| 5,457,085 A | 10/1995 | Seckinger et al. |
| 5,476,936 A | 12/1995 | Philipp et al. |
| 5,648,315 A | 7/1997 | Lorenz et al. |
| 5,922,646 A | 7/1999 | Schnabel et al. |
| 5,925,597 A | 7/1999 | Lorenz et al. |
| 5,990,047 A | 11/1999 | Hacker et al. |
| 6,159,900 A | 12/2000 | Bieringer et al. |
| 6,239,306 B1 | 5/2001 | Lorenz et al. |
| 6,329,323 B1 | 12/2001 | Bettarini et al. |
| 6,498,253 B1 | 12/2002 | Schnabel et al. |
| 7,074,743 B1 | 7/2006 | Hacker et al. |
| 7,482,308 B2 | 1/2009 | Araki et al. |
| 7,829,703 B2 | 11/2010 | Araki et al. |
| 8,008,484 B2 | 8/2011 | Araki et al. |
| 2007/0197390 A1 | 8/2007 | Araki et al. |
| 2007/0219199 A1 | 9/2007 | Araki et al. |
| 2007/0281859 A1* | 12/2007 | Sievernich et al. ........... 504/139 |
| 2008/0312084 A1 | 12/2008 | Araki et al. |
| 2009/0013424 A1 | 1/2009 | Yao et al. |
| 2010/0285964 A1 | 11/2010 | Waldraff et al. |

FOREIGN PATENT DOCUMENTS

| | | |
|---|---|---|
| DE | 1031571 | 6/1958 |
| DE | 1567151 | 7/1969 |
| DE | 1300947 | 8/1969 |
| DE | 2135768 | 1/1972 |
| DE | 2305495 | 8/1973 |
| DE | 2328340 | 12/1973 |
| DE | 2648008 | 5/1978 |
| DE | 2822155 | 11/1979 |
| DE | 3303388 | 8/1983 |
| DE | 1039779 | 9/1985 |
| EP | 0007677 | 2/1980 |
| EP | 0007677 A1 | 2/1980 |
| EP | 0048436 A1 | 3/1982 |
| EP | 0053011 | 6/1982 |
| EP | 0053011 A1 | 6/1982 |
| EP | 0084020 | 7/1983 |
| EP | 0084020 A2 | 7/1983 |
| EP | 0087780 | 9/1983 |
| EP | 0087780 B1 | 9/1983 |
| EP | 0120814 | 10/1984 |
| EP | 0120814 A2 | 10/1984 |
| EP | 0131258 | 1/1985 |
| EP | 0131258 A2 | 1/1985 |
| EP | 0131624 A1 | 1/1985 |
| EP | 0136061 | 4/1985 |
| EP | 0136061 A2 | 4/1985 |
| EP | 0142924 A2 | 5/1985 |
| EP | 0184385 | 6/1986 |
| EP | 0184385 A2 | 6/1986 |
| EP | 0193259 B1 | 9/1986 |
| EP | 0205271 | 12/1986 |
| EP | 0205271 A1 | 12/1986 |
| EP | 0206251 | 12/1986 |
| EP | 0206251 A1 | 12/1986 |
| EP | 0221044 B1 | 5/1987 |
| EP | 0239414 | 9/1987 |
| EP | 0239414 A1 | 9/1987 |
| EP | 0305939 | 3/1989 |
| EP | 0305939 A1 | 3/1989 |
| EP | 0315889 | 5/1989 |
| EP | 0315889 A2 | 5/1989 |
| EP | 0324569 | 7/1989 |
| EP | 0324569 A2 | 7/1989 |
| EP | 0336151 A2 | 10/1989 |
| EP | 0348737 | 1/1990 |
| EP | 0348737 A1 | 1/1990 |
| EP | 0360750 | 3/1990 |
| EP | 0360750 A2 | 3/1990 |
| EP | 0447004 | 9/1991 |
| EP | 0447004 A2 | 9/1991 |
| EP | 0476555 A2 | 3/1992 |
| EP | 0502014 A1 | 9/1992 |
| EP | 0582892 | 2/1994 |
| EP | 0658549 | 6/1995 |
| EP | 0658549 A1 | 6/1995 |
| EP | 0971902 | 1/2000 |
| EP | 0971902 A1 | 1/2000 |
| GB | 574995 | 1/1946 |
| GB | 869169 | 5/1961 |
| GB | 1040541 | 9/1966 |
| HU | 176582 | 3/1981 |
| JP | 55-127302 | 10/1980 |
| JP | 60-67463 | 4/1985 |
| JP | 1-98331 | 4/1989 |
| WO | 83/00329 | 2/1983 |
| WO | WO-8300329 A1 | 2/1983 |
| WO | WO-8402919 A1 | 8/1984 |
| WO | 88/04297 | 6/1988 |
| WO | 91/05781 | 5/1991 |
| WO | WO-9105781 A1 | 5/1991 |
| WO | WO-9107089 A1 | 5/1991 |
| WO | WO-9113972 A1 | 9/1991 |
| WO | WO-9119806 A1 | 12/1991 |
| WO | WO-9211376 A1 | 7/1992 |
| WO | 92/15576 | 9/1992 |
| WO | WO-9214827 A1 | 9/1992 |
| WO | WO-9215576 A1 | 9/1992 |
| WO | 93/09099 | 5/1993 |
| WO | WO-9309099 A2 | 5/1993 |
| WO | 95/10507 | 4/1995 |
| WO | WO-9510507 A1 | 4/1995 |
| WO | 95/59899 | 11/1995 |
| WO | WO-9529899 A1 | 11/1995 |
| WO | 96/41537 | 12/1996 |
| WO | WO-9641537 A1 | 12/1996 |
| WO | WO-9840361 A1 | 9/1998 |
| WO | 02/30921 | 4/2002 |
| WO | WO-0230921 A1 | 4/2002 |
| WO | 02/36595 | 5/2002 |
| WO | WO-0236595 A2 | 5/2002 |
| WO | 2005/096818 | 10/2005 |
| WO | WO-2005096818 A1 | 10/2005 |
| WO | 2006/008159 | 1/2006 |
| WO | 2008/124495 | 10/2008 |
| WO | WO-2008124495 A2 | 10/2008 |
| WO | 2009/031031 | 3/2009 |
| WO | 2009/046334 | 4/2009 |
| WO | 2009/053058 | 4/2009 |
| WO | WO-2009046334 A1 | 4/2009 |
| WO | WO-2009053058 A2 | 4/2009 |
| WO | 2010037061 | 4/2010 |

OTHER PUBLICATIONS

Altschul, et al., "Basic Local Alignment Search Tool", Journal of Molecular Biology, (1990), 215, pp. 403-410.

Ashigh, et al., "Characterization and diagnostic tests of resistance to acetohydroxyacid synthase inhibitors due to an Asp376Glu substitution in Amaranthus powellii", Pesticide Biochemistry and Physiology 95, (2009), pp. 38-46.

Beyer, et al., Sulfonylureas in Herbicides: Chemistry, Degradation, and Mode of Action; Marcel Decker, New York, 1988, pp. 117-1989.

(56) References Cited

OTHER PUBLICATIONS

Braun, et al., "The General Mitochondrial Processing Peptidase From Potato is an Integral Part of Cytochrome C Reductase of the Respiratory Chain", EMBO Journal, vol. 11, No. 9, (1992), pp. 3219-3227.
Chang, A.K., and Duggleby, R.G., "Herbicide-resistant forms of Arabidopsis thaliana acetohydroxyacid synthase: characterization of the catalytic properties and sensitivity to inhibitors of four defined mutants", (1998), Biochem J., 333, pp. 765-777.
Chipman, et al., "Biosynthesis of 2-aceto-2-hydroxy acids: acetolactate synthases and acetohydroxyacid synthases", Biochimica et Biophysica Acta 1385, (1998), pp. 401-419.
Duggleby, et al., "Systematic characterization of mutations in yeast acetohydroxyacid synthase", European Journal of Biochemistry, 270 (2003), pp. 2895-2904.
Duggleby, et al., "Structure and mechanism of inhibition of plant acetohydroxyacid synthase", Plant Physiology and Biochemistry, 46, (2008), pp. 309-324.
Duggleby, et al., "Acetohydroxyacid Synthase", Journal of Biochemistry and Molecular Biology, vol. 33, No. 1, Jan. 2000, pp. 1-36.
Duggleby, et al., "Structure and Properties of Acetohydroxyacid Synthase", in Thiamine: Catalytic Mechanisms in Normal and Disease States, vol. 11, Marcel Dekker, New York, 2004, pp. 251-274.
Hattori, et al., "An acetohydroxy acid synthase mutant reveals a single site involved in multiple herbicide resistance", Mol Gen Genet, (1995), 246, pp. 419-425.
Jander, et al., "Ethylmethanesulfonate Saturation Mutagenesis in Arabidopsis to Determine Frequency of Herbicide Resistance", (2003), Plant Physiol., 131, pp. 139-146.
Jesske, et al., Tagung der Vereinigung der Pflanzenzuchter and Saatgutkaufleute Österreichs, 2009, 171-172, ISBN: 978-3-902559-37-1.
Jung, et al., "Amino acid residues conferring herbicide resistance in tobacco acetohydroxy acid synthase", Biochem J., (2004), 383, pp. 53-61.
Kleschick, et al., "DE-498, a New Acetolactate Synthase Inhibiting Herbicide with Multicrop Selectivity", J. Agric. Food Chem., (1992), 40, pp. 1083-1085.
Kolkman, et al., "Acetohydroxyacid synthase mutations conferring resistance to imidazolinone or sulfonylurea herbicides in sunflower", Theoretical and Applied Genetics, (2004), 109, pp. 1147-1159.
Langeluddeke, et al., "Factors Affecting Herbicidal Activity and Selectivity", Proc. EWRS Symp., (1988), pp. 227-232.
Needleman, Saul B., and Wunsch, Christian D., "A General Method Applicable to the Search for Similarities in the Amino Acid Sequence of Two Proteins", J. Mol. Biol., (1970), 48, pp. 443-453, in the European Molecular Biology Open Software Suite (EMBOSS).
Pang, et al., "Molecular Basis of Sulfonylurea Herbicide Inhibition of Acetohydroxyacid Synthase", Journal of Biological Chemistry, vol. 278, No. 9, Feb. 28, 2003, pp. 7639-7644.
Pontzen, R., "Propoxycarbazone-sodium (BAY MKH 6561): systematic properties and basis of selectivity in wheat", Pflanzenschutz-Nachrichten Bayer, (2002), 55, pp. 37-52.
Prosch, et al., "Edaphic and Environmental Conditions Affecting Performance", Proceedings Southern Weed Science Society, (1992), 45, 3 pages.
Rice, et al., 2000, Trends in Genetics 16(6): 276-277; see e.g. http://www.ebi.ac.uk/emboss/align/index.html).
Shaner, Dale L., and O'Connor, Susan L. (Eds.), "The Imidazolinone Herbicides", CRC Press, Boca Raton, FL, 1991.
Shaner, Dale L., et al., "Potent Inhibitors of Acetohydroyacid Synthase", Plant Physiol., (1984), 76, pp. 545-546.
Shimizu, Tsutomu, "Action Mechanism of Pyrimidinyl Carboxy Herbicides", Pesticide Science, 1997, 22, pp. 245-256.
Shimizu, et al., "Acetolactate Synthase Inhibitors", in Herbicide Classes in Development, Boger, P., Wakabayashi, K., Hirai, K., (Eds.), Springer Verlag, Berlin, 2002, pp. 1-41.
Singh, et al., "Assay of Acetohydroxyacid Synthase", Analytical Biochemistry 171, (1988), pp. 173-179.
Sonnewald, et al., "Transgenic tobacco plants expressing yeast-derived invertase in either the cytosol, vacuole or apoplast: a powerful tool for studying sucrose metabolism and sink/source interactions", The Plant Journal, (1991), 1(1), pp. 95-106.
Tan, et al., "Imidazolinone-tolerant crops: history, current status and future", Pest Management Science, 61, (2005), pp. 246-257.
Tang, et al., "Genetic variation of yellow-seeded rapeseed lines (*Brassica napus* L.) from different genetic sources", Plant Breeding, vol. 116, Issue 5, Oct. 1997, pp. 471-474.
Tranel, P.J., and Wright, T.R., "Weed Science", (2002), 50, pp. 700-712.
Thompson, et al., "CLUSTAL W: improving the sensitivity of progressive multiple sequence alignment through sequence weighting, position-specific gap penalties and weight matrix choice", Nucleic Acids Research, Oxford University Press, (1994), vol. 22, No. 22, pp. 4673-4680.
Umbarger, H.E., "Amino Acid Biosynthesis and Its Regulation", Department of Biological Sciences, Purdue University, Ann. Rev. Biochem., (1978), 47, pp. 533-606.
Weed Research, "Glossary of Common Names and Abbreviations of Herbicides", Weed Research, (1986), vol. 26, pp. 441-445, or "The Pesticide Manual", 14th edition, The British Crop Protection Council, 2007, or 15th edition, 2010, or in the corresponding "e-Pesticide Manual", Version 5, (2010).
Weed Science, "Room for Growth: Our Responsibility", Proceedings Southern Weed Science Society, 36th Annual Meeting, Jan. 18-20, 1983, pp. 90-91.
Weed Science, Modern Agrochemicals, Weed Science Society Meeting, (1984), 18, 2004, pp. 14-15.
Wolter, et al., "rbcS genes in Solanum tuberosum: Conservation of transit peptide and exon shuffling during evolution", Proc. Natl. Acad. Sci. USA, vol. 85, Feb. 1988, pp. 846-850.
Yadav, et al., "Single amino acid substitutions in the enzyme acetolactate synthase confer resistance to the herbicide sulfometuron methyl", (1986), Proc. Natl. Acad. Sci. USA, vol. 83, Jun. 1986, pp. 4418-4422.

* cited by examiner

FIG. 1A

```
                        1                                                  50
    SEQ ID NO 9    (1)  ATGGCGGCGGCAACAACAACAACAACAACATCTTCTTCGATCTCCTTCTC
    SEQ ID NO 5    (1)  ATGGCGGCGGCAACATCG--------------TCTTCTCCGATCTCCTTAAC
    SEQ ID NO 1    (1)  ATGGCGGCGGCAACATCG--------------TCTTCTCCGATCTCCTTAAC
    SEQ ID NO 3    (1)  ATGGCGGCGGCAACATCG--------------TCTTCTCCGATCTCCTTAAC
    SEQ ID NO 7    (1)  ATGGCGGCGGCAACATCG--------------TCTTCTCCGATCTCCTTAAC
                        51                                                 100
    SEQ ID NO 9   (51)  CACCAAACCATCTCCTTCCTCCTCCAAATCACCATTACCAATCTCCAGAT
    SEQ ID NO 5   (39)  CGCTAAACCTTC---T-------TCCAAATCCCCTCTACCCATTTCCAGAT
    SEQ ID NO 1   (39)  CGCTAAACCTTC---T-------TCCAAATCCCCTCTACCCATTTCCAGAT
    SEQ ID NO 3   (39)  CGCTAAACCTTC---T-------TCCAAATCCCCTCTACCCATTTCCAGAT
    SEQ ID NO 7   (39)  CGCTAAACCTTC---T-------TCCAAATCCCCTCTACCCATTTCCAGAT
                        101                                                150
    SEQ ID NO 9  (101)  TCTCCCTCCCATTCTCGCTAAACCCCAACAAATCATCCTCCTCCTCCCGC
    SEQ ID NO 5   (80)  TCTCCCTTCCCTTCTCCTTAACCCCACAGAAAGA-------CTCCTCCCGT
    SEQ ID NO 1   (80)  TCTCCCTTCCCTTCTCCTTAACCCCACAGAAAGA-------CTCCTCCCGT
    SEQ ID NO 3   (80)  TCTCCCTTCCCTTCTCCTTAACCCCACAGAAACC-------CTCCTCCCGT
    SEQ ID NO 7   (80)  TCTCCCTTCCCTTCTCCTTAACCCCACAGAAACC-------CTCCTCCCGT
                        151                                                200
    SEQ ID NO 9  (151)  CGCCGCGGTATCAAATCCAGCTCTCCCTCCTCCATCTCCGCCGTGCTCAA
    SEQ ID NO 5  (124)  CTCCACCGTC-----------CTCTC-----GCCATCTCCGCCGTTCTCAA
    SEQ ID NO 1  (124)  CTCCACCGTC-----------CTCTC-----GCCATCTCCGCCGTTCTCAA
    SEQ ID NO 3  (124)  CTCCACCGTC-----------CACTC-----GCCATCTCCGCCGTTCTCAA
    SEQ ID NO 7  (124)  CTCCACCGTC-----------CTCTC-----GCCATCTCCGCCGTTCTCAA
                        201                                                250
    SEQ ID NO 9  (201)  CACAACCACCAATGTGACAACCACTCCCTCTCCAACCAAACCTACCAAAC
    SEQ ID NO 5  (159)  CTCACCCGTCAATGTCGCACCTCCTTCCCCTGAAA--AAACCGACAAGAA
    SEQ ID NO 1  (159)  CTCACCCGTCAATGTCGCACCTCCTTCCCCTGAAA--AAACCGACAAGAA
    SEQ ID NO 3  (159)  CTCACCCGTCAATGTCGCA-CC------T---GAAA--AAACCGACAAGAT
    SEQ ID NO 7  (159)  CTCACCCGTCAATGTCGCA-CC------T---GAAA--AAACCGACAAGAT
                        251                                                300
    SEQ ID NO 9  (251)  CCGAAACATTCATCTCCCGATTCGCTCCAGATCAACCCCGCAAAGGCGCT
    SEQ ID NO 5  (207)  CA--AGACTTTCGTCTCCCGCTACGCTCCCGACGAGCCCCGCAAGGGTGCT
    SEQ ID NO 1  (207)  CA--AGACTTTCGTCTCCCGCTACGCTCCCGACGAGCCCCGCAAGGGTGCT
    SEQ ID NO 3  (198)  CA--AGACTTTCATCTCCCGCTACGCTCCCGACGAGCCCCGCAAGGGTGCT
    SEQ ID NO 7  (198)  CA--AGACTTTCATCTCCCGCTACGCTCCCGACGAGCCCCGCAAGGGTGCT
                        301                                                350
    SEQ ID NO 9  (301)  GATATCCTCGTCGAAGCTTTAGAACGTCAAGGCGTAGAAACCGTATTCGC
    SEQ ID NO 5  (256)  GATATCCTCGTCGAAGCCCTCGAGCGTCAAGGCGTCGAAACCGTCTTTGC
    SEQ ID NO 1  (256)  GATATCCTCGTCGAAGCCCTCGAGCGTCAAGGCGTCGAAACCGTCTTCGC
    SEQ ID NO 3  (247)  GATATCCTCGTGGAAGCCCTCGAGCGTCAAGGCGTCGAAACCGTCTTCGC
    SEQ ID NO 7  (247)  GATATCCTCGTGGAAGCCCTCGAGCGTCAAGGCGTCGAAACCGTCTTCGC
                        351                                                400
    SEQ ID NO 9  (351)  TTACCCTGGAGGTGCATCAATGGAGATTCACCAAGCCTTAACCCGCTCTT
    SEQ ID NO 5  (306)  TTATCCCGGAGGTGCTTCCATGGAGATCCACCAAGCCTTGACTCGCTCCT
    SEQ ID NO 1  (306)  TTATCCCGGAGGTGCTTCCATGGAGATCCACCAAGCCTTGACTCGCTCCT
    SEQ ID NO 3  (297)  TTATCCCGGAGGTGCCTCCATGGAGATCCACCAAGCCTTGACTCGCTCCT
    SEQ ID NO 7  (297)  TTATCCCGGAGGTGCCTCCATGGAGATCCACCAAGCCTTGACTCGCTCCT
                        401                                                450
    SEQ ID NO 9  (401)  CCTCAATCCGTAACGTCCTTCCTCGTCACGAACAAGGAGGTGTATTCGCA
    SEQ ID NO 5  (356)  CCACCATCCGTAACGTCCTTCCCCGTCACGAACAAGGAGGAGTCTTCGCC
    SEQ ID NO 1  (356)  CCACCATCCGTAACGTCCTTCCCCGTCACGAACAAGGAGGAGTCTTCGCC
    SEQ ID NO 3  (347)  CCACCATCCGTAACGTCCTCCCCCGTCACGAACAAGGAGGAGTCTTCGCC
    SEQ ID NO 7  (347)  CCACCATCCGTAACGTCCTCCCCCGTCACGAACAAGGAGGAGTCTTCGCC
                        451                                                500
    SEQ ID NO 9  (451)  GCAGAAGGATACGCTCGATCCTCAGGTAAACCAGGTATCTGTATAGCCAC
    SEQ ID NO 5  (406)  GCCGAGGGTTACGCTCGTTCCTCCGGCAAACCGGGAATCTGCATAGCCAC
    SEQ ID NO 1  (406)  GCCGAGGGTTACGCTCGTTCCTCCGGCAAACCGGGAATCTGCATAGCCAC
    SEQ ID NO 3  (397)  GCCGAGGGTTACGCTCGTTCCTCCGGCAAACCGGGAATCTGCATAGCCAC
    SEQ ID NO 7  (397)  GCCGAGGGTTACGCTCGTTCCTCCGGCAAACCGGGAATCTGCATAGCCAC
```

FIG. 1B

```
                               501                                              550
         SEQ ID NO 9    (501)  TTCAGGTCCCGGAGCTACAAATCTCGTTAGCGGATTAGCCGATGCGTTGT
         SEQ ID NO 5    (456)  TTCGGGTCCCGGAGCTACCAACCTCGTCAGCGGGTTAGCAGACGCGATGC
         SEQ ID NO 1    (456)  TTCGGGTCCCGGAGCTACCAACCTCGTCAGCGGGTTAGCAGACGCGATGC
         SEQ ID NO 3    (447)  TTCGGGTCCCGGAGCTACCAACCTCGTCAGCGGGTTAGCCGACGCGATGC
         SEQ ID NO 7    (447)  TTCGGGTCCCGGAGCTACCAACCTCGTCAGCGGGTTAGCCGACGCGATGC
                               551                                              600
         SEQ ID NO 9    (551)  TAGATAGTGTTCCTCTTGTAGCAATCACAGGACAAGTCCCTCGTCGTATG
         SEQ ID NO 5    (506)  TTGACAGTGTTCCTCTTGTCGCCATTACAGGACAGGTCCCTCGCCGGATG
         SEQ ID NO 1    (506)  TTGACAGTGTTCCTCTTGTCGCCATTACAGGACAGGTCCCTCGCCGGATG
         SEQ ID NO 3    (497)  TTGACAGTGTTCCTCTCGTCGCCATCACAGGACAGGTCCCTCGCCGGATG
         SEQ ID NO 7    (497)  TTGACAGTGTTCCTCTCGTCGCCATCACAGGACAGGTCCCTCGCCGGATG
                               601                                              650
         SEQ ID NO 9    (601)  ATTGGTACAGATGCGTTTCAAGAGACTCCGATTGTTGAGGTAACGCGTTC
         SEQ ID NO 5    (556)  ATCGGTACTGACGTCTTCCAAGAGACACCAATCGTTGAGGTAACGAGGTC
         SEQ ID NO 1    (556)  ATCGGTACTGACGCCTTCCAAGAGACACCAATCGTTGAGGTAACGAGGTC
         SEQ ID NO 3    (547)  ATCGGTACTGACGCGTTCCAAGAGACGCCAATCGTTGAGGTAACGAGGTC
         SEQ ID NO 7    (547)  ATCGGTACTGACGCCTTCCAAGAGACGCCAATCGTTGAGGTAACGAGGTC
                               651                                              700
         SEQ ID NO 9    (651)  GATTACGAAGCATAACTATCTTGTGATGGATGTTGAAGATATCCCTAGGA
         SEQ ID NO 5    (606)  TATTACGAAACATAACTATTTGGTGATGGATGTTGATGACATACCTAGGA
         SEQ ID NO 1    (606)  TATTACGAAACATAACTATTTGGTGATGGATGTTGATGACATACCTAGGA
         SEQ ID NO 3    (597)  TATTACGAAACATAACTATCTGGTGATGGATGTTGATGACATACCTAGGA
         SEQ ID NO 7    (597)  TATTACGAAACATAACTATCTGGTGATGGATGTTGATGACATACCTAGGA
                               701                                              750
         SEQ ID NO 9    (701)  TTATTGAGGAAGCTTTCTTTTTAGCTACTTCTGGTAGACCTGGACCTGTT
         SEQ ID NO 5    (656)  TCGTTCAAGAAGCTTTCTTTCTAGCTACTTCCGGTAGACCCGGACCGGTT
         SEQ ID NO 1    (656)  TCGTTCAAGAAGCTTTCTTTCTAGCTACTTCCGGTAGACCCGGACCGGTT
         SEQ ID NO 3    (647)  TCGTTCAAGAAGCATTCTTTCTAGCTACTTCCGGTAGACCCGGACCGGTT
         SEQ ID NO 7    (647)  TCGTTCAAGAAGCATTCTTTCTAGCTACTTCCGGTAGACCCGGACCGGTT
                               751                                              800
         SEQ ID NO 9    (751)  TTGGTTGATGTTCCTAAAGATATTCAACAACAGCTTGCGGATTCCTAATTG
         SEQ ID NO 5    (706)  TTGGTTGATGTTCCTAAGGATATTCAGCAGCAGCTTGCGGATTCCTAACTG
         SEQ ID NO 1    (706)  TTGGTTGATGTTCCTAAGGATATTCAGCAGCAGCTTGCGGATTCCTAACTG
         SEQ ID NO 3    (697)  TTGGTTGATGTTCCTAAGGATATTCAGCAGCAGCTTGCGGATTCCTAACTG
         SEQ ID NO 7    (697)  TTGGTTGATGTTCCTAAGGATATTCAGCAGCAGCTTGCGGATTCCTAACTG
                               801                                              850
         SEQ ID NO 9    (801)  GGAACAGGCTATGAGATTACCTGGTTATATGTCTAGGATGCCTAAACCTC
         SEQ ID NO 5    (756)  GGATCAACCTATGCGCTTACCTGGCTACATGTCTAGGTTGCCTCAGCCTC
         SEQ ID NO 1    (756)  GGATCAACCTATGCGCTTACCTGGCTACATGTCTAGGTTGCCTCAGCCTC
         SEQ ID NO 3    (747)  GGATCAACCTATGCGCTTGCCTGGCTACATGTCTAGGCTGCCTCAGCCAC
         SEQ ID NO 7    (747)  GGATCAACCTATGCGCTTGCCTGGCTACATGTCTAGGCTGCCTCAGCCAC
                               851                                              900
         SEQ ID NO 9    (851)  CGGAAGATTCTCATTTGGAGCAGATTGTTAGGTTGATTTCTGAGTCTAAG
         SEQ ID NO 5    (806)  CGGAAGTTTCTCAGTTAGGTCAGATCGTTAGGTTGATCTCGGAGTCTAAG
         SEQ ID NO 1    (806)  CGGAAGTTTCTCAGTTAGGTCAGATCGTTAGGTTGATCTCGGAGTCTAAG
         SEQ ID NO 3    (797)  CGGAAGTTTCTCAGTTAGGCCAGATCGTTAGGTTGATCTCGGAGTCTAAG
         SEQ ID NO 7    (797)  CGGAAGTTTCTCAGTTAGGCCAGATCGTTAGGTTGATCTCGGAGTCTAAG
                               901                                              950
         SEQ ID NO 9    (901)  AAGCCTGTGTTGTATGTTGGTGGTGGTTGTTTGAATTCTAGCGATGAATT
         SEQ ID NO 5    (856)  AGGCCTGTTTTGTACGTTGGTGGTGGAAGCTTGAACTCGAGTGAAGAACT
         SEQ ID NO 1    (856)  AGGCCTGTTTTGTACGTTGGTGGTGGAAGCTTGAACTCGAGTGAAGAACT
         SEQ ID NO 3    (847)  AGGCCTGTTTTGTACGTTGGTGGTGGAAGCTTGAACTCGAGTGAAGAACT
         SEQ ID NO 7    (847)  AGGCCTGTTTTGTACGTTGGTGGTGGAAGCTTGAACTCGAGTGAAGAACT
                               951                                             1000
         SEQ ID NO 9    (951)  GGGTAGGTTGTTGAGCTTACGGGGATCCCTGTTGCGAGTACGTTGATGG
         SEQ ID NO 5    (906)  GGGGAGATTTGTCGAGCTTACTGGGATCCCCGTTGCGAGTACTTTGATGG
         SEQ ID NO 1    (906)  GGGGAGATTTGTCGAGCTTACTGGGATCCCCGTTGCGAGTACTTTGATGG
         SEQ ID NO 3    (897)  GGGGAGATTTGTCGAGCTTACTGGGATCCCTGTTGCGAGTACGTTGATGG
         SEQ ID NO 7    (897)  GGGGAGATTTGTCGAGCTTACTGGGATCCCTGTTGCGAGTACGTTGATGG
                              1001                                             1050
         SEQ ID NO 9   (1001)  GGCTGGGATCTTATCCTTGTGATGATGAGTTGTCGTTACATATGCTTGGA
         SEQ ID NO 5    (956)  GGCTTGGCTCTTATCCTTGTAACGATGAGTTGTCCCTGCAGATGCTTGGC
         SEQ ID NO 1    (956)  GGCTTGGCTCTTATCCTTGTAACGATGAGTTGTCCCTGCAGATGCTTGGC
         SEQ ID NO 3    (947)  GGCTTGGCTCTTATCCTTGTAACGATGAGTTGTCCCTGCAGATGCTTGGC
         SEQ ID NO 7    (947)  GGCTTGGCTCTTATCCTTGTAACGATGAGTTGTCCCTGCAGATGCTTGGC
```

FIG. 1C

```
                         1051                                              1100
SEQ ID NO 9     (1051)   ATGCATGGGACTGTGTATGCAAATTACGCTGTGGAGCATAGTGATTTGTT
SEQ ID NO 5     (1006)   ATGCACGGGACTGTGTATGCTAACTACGCTGTGGAGCATAGTGATTTGTT
SEQ ID NO 1     (1006)   ATGCACGGGACTGTGTATGCTAACTACGCTGTGGAGCATAGTGATTTGTT
SEQ ID NO 3     (997)    ATGCACGGGACTGTGTATGCTAACTACGCTGTGGAGCATAGTGATTTGTT
SEQ ID NO 7     (997)    ATGCACGGGACTGTGTATGCTAACTACGCTGTGGAGCATAGTGATTTGTT
                         1101                                              1150
SEQ ID NO 9     (1101)   GTTGGCGTTTGGGGTAAGGTTTGATGATCGTGTCACGGGTAAGCTTGAGG
SEQ ID NO 5     (1056)   GCTGGCGTTTGGTGTTAGGTTTGATGACCGTGTCACGGGAAAGCTCGAGG
SEQ ID NO 1     (1056)   GCTGGCGTTTGGTGTTAGGTTTGATGACCGTGTCACGGGAAAGCTCGAGG
SEQ ID NO 3     (1047)   GCTGGCGTTTGGTGTTAGGTTTGATGACCGTGTCACGGGAAAGCTCGAGG
SEQ ID NO 7     (1047)   GCTGGCGTTTGGTGTTAGGTTTGATGACCGTGTCACGGGAAAGCTCGAGG
                         1151                                              1200
SEQ ID NO 9     (1151)   CTTTTGCTAGTAGGGCTAAGATTGTTCATATTGATATTGACTCGGCTGAG
SEQ ID NO 5     (1106)   CTTTCGCTAGCAGGGCTAAAATTGTGCACATAGACATTGATTCTGCTGAG
SEQ ID NO 1     (1106)   CTTTCGCTAGCAGGGCTAAAATTGTGCACATAGACATTGATTCTGCTGAG
SEQ ID NO 3     (1097)   CGTTTGCGAGCAGGGCTAAGATTGTGCACATAGACATTGATTCTGCTGAG
SEQ ID NO 7     (1097)   CGTTTGCGAGCAGGCGCTAAGATTGTGCACATAGACATTGATTCTGCTGAG
                         1201                                              1250
SEQ ID NO 9     (1201)   ATTGGGAAGAATAAGACTCCTCATGTGTCTGTGTGTGGTGATGTTAAGCT
SEQ ID NO 5     (1156)   ATTGGGAAGAATAAGACACCTCACGTGTCTGTGTGTGGTGATGTAAAGCT
SEQ ID NO 1     (1156)   ATTGGGAAGAATAAGACACCTCACGTGTCTGTGTGTGGTGATGTAAAGCT
SEQ ID NO 3     (1147)   ATTGGGAAGAATAAGCACCTCACGTGTCTGTGTGTGGTGATGTAAAGCT
SEQ ID NO 7     (1147)   ATTGGGAAGAATAAGACACCTCACGTGTCTGTGTGTGGTGATGTAAAGCT
                         1251                                              1300
SEQ ID NO 9     (1251)   GGCTTTGCAAGGGATGAATAAGGTTCTTGAGAACCGAGCGGAGGAGCTTA
SEQ ID NO 5     (1206)   GGCTTTGCAAGGGATGAACAAGGTTCTTGAGAACCGGGCGGAGGAGCTCA
SEQ ID NO 1     (1206)   GGCTTTGCAAGGGATGAACAAGGTTCTTGAGAACCGGGCGGAGGAGCTCA
SEQ ID NO 3     (1197)   GGCTTTGCAAGGGATGAACAAGGTTCTTGAGAACCGGGCGGAGGAGCTCA
SEQ ID NO 7     (1197)   GGCTTTGCAAGGGATGAACAAGGTTCTTGAGAACCGGGCGGAGGAGCTCA
                         1301                                              1350
SEQ ID NO 9     (1301)   AGCTTGATTTTGGAGTTTGGAGGAATGAGTTGAACGTACAGAAACAGAAG
SEQ ID NO 5     (1256)   AGCTTGATTTCGGTGTTTGGAGGAGTGAGTTGAGCGAGCAGAAACAGAAG
SEQ ID NO 1     (1256)   AGCTTGATTTCGGTGTTTGGAGGAGTGAGTTGAGCGAGCAGAAACAGAAG
SEQ ID NO 3     (1247)   AGCTTGATTTCGGTGTTTGGAGGAGTGAGTTGAGCGAGCAGAAACAGAAG
SEQ ID NO 7     (1247)   AGCTTGATTTCGGTGTTTGGAGGAGTGAGTTGAGCGAGCAGAAACAGAAG
                         1351                                              1400
SEQ ID NO 9     (1351)   TTTCCGTTGAGCTTTAAGACGTTTGGGGAAGCTATTCCTCCACAGTATGC
SEQ ID NO 5     (1306)   TTCCCTTTGAGCTTCAAAACGTTTGGAGAAGCCATTCCTCCGCAGTACGC
SEQ ID NO 1     (1306)   TTCCCTTTGAGCTTCAAAACGTTTGGAGAAGCCATTCCTCCGCAGTACGC
SEQ ID NO 3     (1297)   TTCCCGTTGAGCTTCAAAACGTTTGGAGAAGCCATTCCTCCGCAGTACGC
SEQ ID NO 7     (1297)   TTCCCGTTGAGCTTCAAAACGTTTGGAGAAGCCATTCCTCCGCAGTACGC
                         1401                                              1450
SEQ ID NO 9     (1401)   GATTAAGGTCCTTGATGAGTTGACTGATGGAAAAGCCATAATAAGTACTG
SEQ ID NO 5     (1356)   GATTCAGATCCTCGAGCAGCTAACCGAAGGGAAGGCAATTATCAGTACTG
SEQ ID NO 1     (1356)   GATTCAGATCCTCGACGAGCTAACCGAAGGGAAGGCAATTATCAGTACTG
SEQ ID NO 3     (1347)   GATTCAGGTCCTAGACGAGCTAACCCAAGGGAAGGCAATTATCAGTACTG
SEQ ID NO 7     (1347)   GATTCAGGTCCTAGACGAGCTAACCCAAGGGAAGGCAATTATCAGTACTG
                         1451                                              1500
SEQ ID NO 9     (1451)   GTGTCGGGCAACATCAAATGTGGGCGGCGCAGTTCTACAATTACAAGAAA
SEQ ID NO 5     (1406)   GTGTTGGACAGCATCAGATGTGGGCGGCGCAGTTTTACAAGTACAGGAAG
SEQ ID NO 1     (1406)   GTGTTGGACAGCATCAGATGTGGGCGGCGCAGTTTTACAAGTACAGGAAG
SEQ ID NO 3     (1397)   GTGTTGGACAGCATCAGATGTGGGCGGCGCAGTTTTACAAGTACAGGAAG
SEQ ID NO 7     (1397)   GTGTTGGACAGCATCAGATGTGGGCGGCGCAGTTTTACAAGTACAGGAAG
                         1501                                              1550
SEQ ID NO 9     (1501)   CCAAGGCAGTGGCTATCATCAGGAGGCCTTGGAGCTATGGGATTGGACT
SEQ ID NO 5     (1456)   CCGAGACAGTGGCTGTCGTCATCAGGCCTCGGAGCTATGGGTTTTGGACT
SEQ ID NO 1     (1456)   CCGAGACAGTGGCTGTCGTCATCAGGCCTCGGAGCTATGGGTTTTGGACT
SEQ ID NO 3     (1447)   CCGAGGCAGTGGCTGTCGTCCTCAGGACTCGGAGCTATGGGTTTCGGACT
SEQ ID NO 7     (1447)   CCGAGGCAGTGGCTGTCGTCCTCAGGACTCGGAGCTATGGGTTTCGGACT
                         1551                                              1600
SEQ ID NO 9     (1551)   TCCTGCTGCGATTGGAGCGTCTGTTGCTAACCCTGATGCGATAGTTGTGG
SEQ ID NO 5     (1506)   TCCTGCTGCGATTGGAGCGTCTGTGGCGAACCCTGATGCGATTGTTGTGG
SEQ ID NO 1     (1506)   TCCTGCTGCGATTGGAGCGTCTGTGGCGAACCCTGATGCGATTGTTGTGG
SEQ ID NO 3     (1497)   TCCTGCTGCGATTGGAGCGTCTGTGGCGAACCCTGATGCGATTGTTGTGG
SEQ ID NO 7     (1497)   TCCTGCTGCGATTGGAGCGTCTGTGGCGAACCCTGATGCGATTGTTGTGG
```

FIG. 1D

```
                      1601                                              1650
SEQ ID NO 9  (1601) ATATTGACGGAGATGGAAGCTTTATAATGAATGTGCAAGAGCTAGCCACT
SEQ ID NO 5  (1556) ATATTGACGGTGATGGAAGCTTCATAATGAACGTTCAAGAGCTGGCCACA
SEQ ID NO 1  (1556) ATATTGACGGTGATGGAAGCTTCATAATGAACGTTCAAGAGCTGGCCACA
SEQ ID NO 3  (1547) ACATTGACGGTGATGGAAGCTTCATAATGAACGTTCAAGAGCTGGCCACA
SEQ ID NO 7  (1547) ACATTGACGGTGATGGAAGCTTCATAATGAACGTTCAAGAGCTGGCCACA
                      1651                                              1700
SEQ ID NO 9  (1651) ATCGTGTAGAGAATCTTCCAGTGAAGGTACTTTTATTAAACAACCAGCA
SEQ ID NO 5  (1606) ATCCGTGTAGAGAATCTTCCTGTGAAGATACTCTTGTTAAACAACCAGCA
SEQ ID NO 1  (1606) ATCCGTGTAGAGAATCTTCCTGTGAAGATACTCTTGTTAAACAACCAGCA
SEQ ID NO 3  (1597) ATCCGTGTAGAGAATCTTCCTGTGAAGATACTCTTGTTAAACAACCAGCA
SEQ ID NO 7  (1597) ATCCGTGTAGAGAATCTTCCTGTGAAGATACTCTTGTTAAACAACCAGCA
                      1701                                              1750
SEQ ID NO 9  (1701) TCTTGGCATGGTTATGCAATGGCAAGATCGGTTCTACAAAGCTAACCGAG
SEQ ID NO 5  (1656) TCTTGGGATGGTCATGCAATGGGAAGATCGGTTCTACAAAGCTAACAGAG
SEQ ID NO 1  (1656) TCTTGGGATGGTCATGCAATGGGAAGATCGGTTCTACAAAGCTAACAGAG
SEQ ID NO 3  (1647) TCTTGGGATGGTCATGCAATGGGAAGATCGGTTCTACAAAGCTAACAGAG
SEQ ID NO 7  (1647) TCTTGGGATGGTCATGCAATTGGAAGATCGGTTCTACAAAGCTAACAGAG
                      1751                                              1800
SEQ ID NO 9  (1751) CTCACACATTTCTCGGGGATCCGGCTCAGGAGGACGAGATATTCCCGAAC
SEQ ID NO 5  (1706) CTCACACTTATCTCGGGGACCCGGCAAGGGAGAACGAGATCTTCCCTAAC
SEQ ID NO 1  (1706) CTCACACTTATCTCGGGGACCCGGCAAGGGAGAACGAGATCTTCCCTAAC
SEQ ID NO 3  (1697) CTCACACTTATCTCGGGGACCCGGCAAGGGAGAACGAGATCTTCCCTAAC
SEQ ID NO 7  (1697) CTCACACTTATCTCGGGGACCCGGCAAGGGAGAACGAGATCTTCCCTAAC
                      1801                                              1850
SEQ ID NO 9  (1801) ATGTTGCTGTTTGCAGCAGCTTGCGGGATTCCAGCGGCGAGGGTGACAAA
SEQ ID NO 5  (1756) ATGCTGCAGTTTGCAGGAGCTTGCGGGATTCCAGCTGCGAGAGTGACGAA
SEQ ID NO 1  (1756) ATGCTGCAGTTTGCAGGAGCTTGCGGGATTCCAGCTGCGAGAGTGACGAA
SEQ ID NO 3  (1747) ATGCTGCAGTTTGCAGGAGCTTGCGGGATTCCAGCTGCGAGAGTGACGAA
SEQ ID NO 7  (1747) ATGCTGCAGTTTGCAGGAGCTTGCGGGATTCCAGCTGCGAGAGTGACGAA
                      1851                                              1900
SEQ ID NO 9  (1851) GAAAGCAGATCTCCGAGAAGCTATTCAGACAATGCTGGATACACCAGGAC
SEQ ID NO 5  (1806) GAAAGAAGAACTCCGAGAAGCTATTCAGACAATGCTGGATACACCAGGAC
SEQ ID NO 1  (1806) GAAAGAAGAACTCCGAGAAGCTATTCAGACAATGCTGGATACACCAGGAC
SEQ ID NO 3  (1797) GAAAGAAGAACTCCGAGAAGCTATTCAGACAATGCTGGATACACCTGGAC
SEQ ID NO 7  (1797) GAAAGAAGAACTCCGAGAAGCTATTCAGACAATGCTGGATACACCTGGAC
                      1901                                              1950
SEQ ID NO 9  (1901) CTTACCTGTTGGATGTGATTTGTCCGCACCAAGAACATGTGTTGCCGATG
SEQ ID NO 5  (1856) CATACCTGTTGGATGTGATATGTCCGCACCAAGAACATGTGTTACCGATG
SEQ ID NO 1  (1856) CATACCTGTTGGATGTGATATGTCCGCACCAAGAACATGTGTTACCGATG
SEQ ID NO 3  (1847) CGTACCTGTTGGATGTCATCTGTCCGCACCAAGAACATGTGTTACCGATG
SEQ ID NO 7  (1847) CGTACCTGTTGGATGTCATCTGTCCGCACCAAGAACATGTGTTACCGATG
                      1951                                              2000
SEQ ID NO 9  (1951) ATCCCGAGTGGTGGCACTTTCAACGATGTCATAACGGAAGGAGATGGCCG
SEQ ID NO 5  (1906) ATCCCAAGTGGTGGCACTTTCAAAGATGTAATAACAGAAGGGGATGGTCG
SEQ ID NO 1  (1906) ATCCCAAGTGGTGGCACTTTCAAAGATGTAATAACAGAAGGGGATGGTCG
SEQ ID NO 3  (1897) ATCCCAAGTGGTGGCACTTTCAAAGATGTAATAACCGAAGGGGATGGTCG
SEQ ID NO 7  (1897) ATCCCAAGTGGTGGCACTTTCAAAGATGTAATAACCGAAGGGGATGGTCG
                      2001     2013
SEQ ID NO 9  (2001) GATTAAATACTGA
SEQ ID NO 5  (1956) CACTAAGTACTGA
SEQ ID NO 1  (1956) CACTAAGTACTGA
SEQ ID NO 3  (1947) CACTAAGTACTGA
SEQ ID NO 7  (1947) CACTAAGTACTGA
```

FIG. 2A

```
                    1                                                  50
SEQ ID NO 10    (1) MAAATTTTTTSSSISFSTKPSPSSSKSPLPISRFSLPFSLNPNKSSSSSR
SEQ ID NO 2     (1) -----MAAATSSSPISLTAKPS----SKSPLPISRFSLPFSLTPQKDSSRLH
SEQ ID NO 6     (1) -----MAAATSSSPISLTAKPS----SKSPLPISRFSLPFSLTPQKDSSRLH
SEQ ID NO 4     (1) -----MAAATSSSPISLTAKPS----SKSPLPISRFSLPFSLTPQKPSSRLH
SEQ ID NO 8     (1) -----MAAATSSSPISLTAKPS---SKSPLPISRFSLPFSLTPQKPSSRLH
                    51                                                100
SEQ ID NO 10   (51) RRGIKSSSPSSISAVLNTTTNVTTTPSPTKPTKPETFISRFAPDQPRKGA
SEQ ID NO 2    (44) R-------PLAISAVLNSPVNVAP-PSPEKTDKNKTFVSRYAPDEPRKGA
SEQ ID NO 6    (44) R-------PLAISAVLNSPVNVAP-PSPEKTDKNKTFVSRYAPDEPRKGA
SEQ ID NO 4    (44) R-------PLAISAVLNSPVNVAP----EKTDKIKTFISRYAPDEPRKGA
SEQ ID NO 8    (44) R-------PLAISAVLNSPVNVAP----EKTDKIKTFISRYAPDEPRKGA
                    101                                               150
SEQ ID NO 10  (101) DILVEALERQGVETVFAYPGGASMEIHQALTRSSSIRNVLPRHEQGGVFA
SEQ ID NO 2    (86) DILVEALERQGVETVFAYPGGASMEIHQALTRSSTIRNVLPRHEQGGVFA
SEQ ID NO 6    (86) DILVEALERQGVETVFAYPGGASMEIHQALTRSSTIRNVLPRHEQGGVFA
SEQ ID NO 4    (83) DILVEALERQGVETVFAYPGGASMEIHQALTRSSTIRNVLPRHEQGGVFA
SEQ ID NO 8    (83) DILVEALERQGVETVFAYPGGASMEIHQALTRSSTIRNVLPRHEQGGVFA
                    151                                               200
SEQ ID NO 10  (151) AEGYARSSGKPGICIATSGPGATNLVSGLADALLDSVPLVAITGQVPRRM
SEQ ID NO 2   (136) AEGYARSSGKPGICIATSGPGATNLVSGLADAMLDSVPLVAITGQVPRRM
SEQ ID NO 6   (136) AEGYARSSGKPGICIATSGPGATNLVSGLADAMLDSVPLVAITGQVPRRM
SEQ ID NO 4   (133) AEGYARSSGKPGICIATSGPGATNLVSGLADAMLDSVPLVAITGQVPRRM
SEQ ID NO 8   (133) AEGYARSSGKPGICIATSGPGATNLVSGLADAMLDSVPLVAITGQVPRRM
                    201                                               250
SEQ ID NO 10  (201) IGTDAFQETPIVEVTRSITKHNYLVMDVEDIPRIIEEAFFLATSGRPGPV
SEQ ID NO 2   (186) IGTDAFQETPIVEVTRSITKHNYLVMDVDDIPRIVQEAFFLATSGRPGPV
SEQ ID NO 6   (186) IGTDVFQETPIVEVTRSITKHNYLVMDVDDIPRIVQEAFFLATSGRPGPV
SEQ ID NO 4   (183) IGTDAFQETPIVEVTRSITKHNYLVMDVDDIPRIVQEAFFLATSGRPGPV
SEQ ID NO 8   (183) IGTDAFQETPIVEVTRSITKHNYLVMDVDDIPRIVQEAFFLATSGRPGPV
                    251                                               300
SEQ ID NO 10  (251) LVDVPKDIQQQLAIPNWEQAMRLPGYMSRMPKPPEDSHLEQIVRLISESK
SEQ ID NO 2   (236) LVDVPKDIQQQLAIPNWDQPMRLPGYMSRLPQPPEVSQLGQIVRLISESK
SEQ ID NO 6   (236) LVDVPKDIQQQLAIPNWDQPMRLPGYMSRLPQPPEVSQLGQIVRLISESK
SEQ ID NO 4   (233) LVDVPKDIQQQLAIPNWDQPMRLPGYMSRLPQPPEVSQLGQIVRLISESK
SEQ ID NO 8   (233) LVDVPKDIQQQLAIPNWDQPMRLPGYMSRLPQPPEVSQLGQIVRLISESK
                    301                                               350
SEQ ID NO 10  (301) KPVLYVGGGCLNSSDELGRFVELTGIPVASTLMGLGSYPCDDELSLHMLG
SEQ ID NO 2   (286) RPVLYVGGGSLNSSEELGRFVELTGIPVASTLMGLGSYPCNDELSLQMLG
SEQ ID NO 6   (286) RPVLYVGGGSLNSSEELGRFVELTGIPVASTLMGLGSYPCNDELSLQMLG
SEQ ID NO 4   (283) RPVLYVGGGSLNSSEELGRFVELTGIPVASTLMGLGSYPCNDELSLQMLG
SEQ ID NO 8   (283) RPVLYVGGGSLNSSEELGRFVELTGIPVASTLMGLGSYPCNDELSLQMLG
                    351                                               400
SEQ ID NO 10  (351) MHGTVYANYAVEHSDLLLAFGVRFDDRVTGKLEAFASRAKIVHIDIDSAE
SEQ ID NO 2   (336) MHGTVYANYAVEHSDLLLAFGVRFDDRVTGKLEAFASRAKIVHIDIDSAE
SEQ ID NO 6   (336) MHGTVYANYAVEHSDLLLAFGVRFDDRVTGKLEAFASRAKIVHIDIDSAE
SEQ ID NO 4   (333) MHGTVYANYAVEHSDLLLAFGVRFDDRVTGKLEAFASRAKIVHIDIDSAE
SEQ ID NO 8   (333) MHGTVYANYAVEHSDLLLAFGVRFDDRVTGKLEAFASRAKIVHIDIDSAE
                    401                                               450
SEQ ID NO 10  (401) IGKNKTPHVSVCGDVKLALQGMNKVLENRAEELKLDFGVWRNELNVQKQK
SEQ ID NO 2   (386) IGKNKTPHVSVCGDVKLALQGMNKVLENRAEELKLDFGVWRSELSEQKQK
SEQ ID NO 6   (386) IGKNKTPHVSVCGDVKLALQGMNKVLENRAEELKLDFGVWRSELSEQKQK
SEQ ID NO 4   (383) IGKNKTPHVSVCGDVKLALQGMNKVLENRAEELKLDFGVWRSELSEQKQK
SEQ ID NO 8   (383) IGKNKTPHVSVCGDVKLALQGMNKVLENRAEELKLDFGVWRSELSEQKQK
```

FIG. 2B

```
                       451                                                500
    SEQ ID NO 10  (451) FPLSFKTFGEAIPPQYAIKVLDELTDGKAIISTGVGQHQMWAAQFYNYKK
    SEQ ID NO  2  (436) FPLSFKTFGEAIPPQYAIQILDELTEGKAIISTGVGQHQMWAAQFYKYRK
    SEQ ID NO  6  (436) FPLSFKTFGEAIPPQYAIQILDELTEGKAIISTGVGQHQMWAAQFYKYRK
5   SEQ ID NO  4  (433) FPLSFKTFGEAIPPQYAIQVLDELTQGKAIISTGVGQHQMWAAQFYKYRK
    SEQ ID NO  8  (433) FPLSFKTFGEAIPPQYAIQVLDELTQGKAIISTGVGQHQMWAAQFYKYRK
                       501                                                550
    SEQ ID NO 10  (501) PRQWLSSGGLGAMGFGLPAAIGASVANPDAIVVDIDGDGSFIMNVQELAT
    SEQ ID NO  2  (486) PRQWLSSSGLGAMGFGLPAAIGASVANPDAIVVDIDGDGSFIMNVQELAT
10  SEQ ID NO  6  (486) PRQWLSSSGLGAMGFGLPAAIGASVANPDAIVVDIDGDGSFIMNVQELAT
    SEQ ID NO  4  (483) PRQWLSSSGLGAMGFGLPAAIGASVANPDAIVVDIDGDGSFIMNVQELAT
    SEQ ID NO  8  (483) PRQWLSSSGLGAMGFGLPAAIGASVANPDAIVVDIDGDGSFIMNVQELAT
                       551                                                600
    SEQ ID NO 10  (551) IRVENLPVKVLLLNNQHLGMVMQWQDRFYKANRAHTFLGDPAQEDEIFPN
15  SEQ ID NO  2  (536) IRVENLPVKILLLNNQHLGMVMQWEDRFYKANRAHTYLGDPARENEIFPN
    SEQ ID NO  6  (536) IRVENLPVKILLLNNQHLGMVMQWEDRFYKANRAHTYLGDPARENEIFPN
    SEQ ID NO  4  (533) IRVENLPVKILLLNNQHLGMVMQWEDRFYKANRAHTYLGDPARENEIFPN
    SEQ ID NO  8  (533) IRVENLPVKILLLNNQHLGMVMQLEDRFYKANRAHTYLGDPARENEIFPN
                       601                                                650
20  SEQ ID NO 10  (601) MLLFAAACGIPAARVTKKADLREAIQTMLDTPGPYLLDVICPHQEHVLPM
    SEQ ID NO  2  (586) MLQFAGACGIPAARVTKKEELREAIQTMLDTPGPYLLDVICPHQEHVLPM
    SEQ ID NO  6  (586) MLQFAGACGIPAARVTKKEELREAIQTMLDTPGPYLLDVICPHQEHVLPM
    SEQ ID NO  4  (583) MLQFAGACGIPAARVTKKEELREAIQTMLDTPGPYLLDVICPHQEHVLPM
    SEQ ID NO  8  (583) MLQFAGACGIPAARVTKKEELREAIQTMLDTPGPYLLDVICPHQEHVLPM
25                     651       670
    SEQ ID NO 10  (651) IPSGGTFNDVITEGDGRIKY
    SEQ ID NO  2  (636) IPSGGTFKDVITEGDGRTKY
    SEQ ID NO  6  (636) IPSGGTFKDVITEGDGRTKY
    SEQ ID NO  4  (633) IPSGGTFKDVITEGDGRTKY
30  SEQ ID NO  8  (633) IPSGGTFKDVITEGDGRTKY
```

USE OF ALS INHIBITOR HERBICIDES FOR CONTROL OF UNWANTED VEGETATION IN ALS INHIBITOR HERBICIDE TOLERANT *BRASSICA*, SUCH AS *B. NAPUS*, PLANTS

CROSS REFERENCE TO RELATED APPLICATIONS

This application is a §371 National Stage Application of PCT/EP2012/058232, filed May 4, 2012, which claims priority to European Application No. 11164770.7, filed May 4, 2011, and U.S. Provisional Application No. 61/483,096, filed May 6, 2011.

BACKGROUND OF THE INVENTION

1. Field of the Invention

The present invention relates to the technical field of crop protection by using ALS (acetolactate synthase; also known as AHAS (acetohydroxyacid synthase; EC 2.2.1.6; formerly EC 4.1.3.18)) inhibitor herbicides against unwanted vegetation in areas of growing *Brassica* plants (preferably *B. napus* plants) that are tolerant against ALS inhibitor herbicides by comprising non-transgenic mutations of its endogenous acetolactate synthase (ALS) I and III genes.

2. Description of Related Art

Since more than 40 years, herbicides are the preferred tools to control weeds in *B. napus*. The products used for this purpose, namely Metazachlor, Dimethachlor, Quinmerac, Clomazone, Metolachlor, Napropamide, Clopyralid, Propyzamide, Propaquizafop, Fluazifop and others allow suppressing weeds in *B. napus* fields without damaging the crop. Nevertheless, under adverse environmental conditions the efficacy of these products leaves room for improvements, especially if noxious weeds like *Geranium dissectum, Centaurea cyanus, Sinapis arvensis* and/or *Alopecurus myosuroides* germinate over an extended period of time.

The ALS/AHAS enzyme is present in bacteria, fungi, and plants and from various organisms protein isolates have been obtained and their corresponding amino acid/nucleic acid sequences as well as their biochemical characteristics have been determined/characterized (see, e.g., Umbarger et al., Annu. Rev. Biochem. (1978), 47, 533-606; Chiman et al., Biochim Biophys. Acta (1998), 1385, 401-419; Duggleby and Pang, J. Biochem. Mol. Biol. (2000), 33, 1-36; Duggleby: Structure and Properties of Acetohydroxyacid Synthase in Thiamine: Catalytic Mechanisms in Normal and Disease States, Vol 11, Marcel Dekker, New York, 2004, 251-274).

The use of herbicidal compounds belonging to the class of ALS inhibitors, like (a) sulfonylurea herbicides (Beyer E. M et al. (1988), Sulfonylureas in Herbicides: Chemistry, Degradation, and Mode of Action; Marcel Dekker, New York, 1988, 117-189), (b) sulfonylaminocarbonyltriazolinone herbicides (Pontzen, R., Pflanz.-Nachrichten Bayer, 2002, 55, 37-52), (c) imidazolinone herbicides (Shaner, D. L., et al., Plant Physiol., 1984, 76, 545-546; Shaner, D. L., and O'Connor, S. L. (Eds.) The Imidazolinone Herbicides, CRC Press, Boca Raton, Fla., 1991), (d) triazolopyrimidine herbicides (Kleschick, W. A. et al., Agric. Food Chem., 1992, 40, 1083-1085), and (e) pyrimidinyl(thio)benzoate herbicides (Shimizu, T. J., Pestic. Sci., 1997, 22, 245-256; Shimizu, T. et al., Acetolactate Syntehase Inhibitors in Herbicide Classes in Development, Boger, P., Wakabayashi. K., Hirai, K., (Eds.), Springer Verlag, Berlin, 2002, 1-41) for the control of unwanted vegetation in various crop cultures is well known in agriculture.

A broad variety of ALS/AHAS inhibitor herbicides enable a farmer to control a wide range of weed species independently of their growth stages, but these highly efficient herbicides cannot be used in *B. napus* because this crop is highly susceptible against/affected by these ALS inhibitor herbicides. Nevertheless, these ALS inhibitor herbicides show an excellent herbicidal activity against broadleaf and grass weed species. The first herbicides based on ALS inhibitors were developed for their use in agriculture already 30 years ago. Nowadays, active ingredients of this class exhibit a strong weed control and are widely used in maize and cereals.

A flexible way to obtain *B. napus* plants that tolerate ALS inhibitor herbicide treatment is to generate mutants that are tolerant to agronomically useful/necessary quantities of ALS inhibitor herbicides in order to control serious unwanted vegetation in *B. napus* plantings.

Since ALS inhibitor herbicides were introduced into agriculture it was observed that susceptible plant species, including naturally occurring weeds, occasionally develop spontaneous tolerance to this class of herbicides. Single base pair substitutions at specific sites of the ALS gene usually lead to more or less resistant ALS enzyme variants which show different levels of inhibition by the ALS inhibitor herbicides.

Plants conferring mutant ALS alleles therefore show different levels of tolerance to ALS inhibitor herbicides, depending on the chemical structure of the ALS inhibitor herbicide and the site of the point mutation(s) in the ALS gene and the hereby encoded ALS protein.

Several mutants (naturally occurring in weeds but also artificially induced in crops by either mutation or transgenic approaches) of the ALS conferring tolerance to one or more chemicals defined under the above given ALS inhibitor herbicide classes/groups are known at various parts of the enzyme (i.e. in the α-, β-, and γ-domain of the ALS h are known and have been identified in various organisms, including plants (U.S. Pat. No. 5,378,82; Duggleby, R. G. et al., (2008), Plant Physiol. and Biochem., pp 309-324; Siyuan, T. et al. (2005), Pest Management Sci., 61, pp 246-257; Jung, S. (2004) Biochem J., pp 53-61; Kolkman, J. M. (2004), Theor. Appl. Genet., 109, pp 1147-1159; Duggleby, R. G. et al (2003), Eur. J. Biochem., 270, pp 1295-2904; Pang, S. S., et al. (2003), J. Biol. Chem., pp 7639-7644); Yadav, N. et al., (1986), Proc. Natl. Acad. Sci., 83, pp 4418-4422), Jander G. et al. (2003), Plant Physiol., 131, pp. 139-146); Tranel, P. J., and Wright, T. R. (2002), Weed Science, 50, pp 700-712); Chang, A. K., and Duggleby, R. G. (1998), Biochem J., 333, pp. 765-777).

Among the artificially obtained various mutants, it has already been described that these are tolerant against various classes of ALS inhibitor herbicides, like against certain sulfonylureas or representative compounds of the class of imidazolinones.

EP-A-0360750 describes the production of ALS inhibitor herbicide tolerant plants by producing an increased amount of the attacked ALS inside the plant. Such plants show an increased tolerance against certain sulfonyureas, like chlorsulfuron, sulfometuron-methyl, and triasulfuron.

U.S. Pat. No. 5,198,599 describes sulfonylurea and imidazolinone tolerant plants that have been obtained via a selection process and which show a tolerance against chlorsulfuron, bensulfuron, chlorimuron, thifensulfuron and sulfometuron.

WO09/046334 describes mutated acetohydroxyacid synthase (AHAS) nucleic acids and the proteins encoded by the mutated nucleic acids, as well as canola plants, cells, and seeds comprising the mutated genes, whereby the plants display increased tolerance to imidazolinones and sulfonylureas.

WO09/031031 discloses herbicide-resistant *Brassica* plants and novel polynucleotide sequences that encode wild-type and imidazolinone-resistant *Brassica* acetohydroxyacid synthase large subunit proteins, seeds, and methods using such plants.

U.S. patent application Ser. No. 09/0013424 describes improved imidazolinone herbicide resistant *Brassica* lines, including *Brassica juncea*, methods for generation of such lines, and methods for selection of such lines, as well as *Brassica* AHAS genes and sequences and a gene allele bearing a point mutation that gives rise to imidazolinone herbicide resistance.

WO08/124495 discloses nucleic acids encoding mutants of the acetohydroxyacid synthase (AHAS) large subunit comprising at least two mutations, for example double and triple mutants, which are useful for producing transgenic or non-transgenic plants with improved levels of tolerance to AHAS-inhibiting herbicides. The invention also provides expression vectors, cells, plants comprising the polynucleotides encoding the AHAS large subunit double and triple mutants, plants comprising two or more AHAS large subunit single mutant polypeptides, and methods for making and using the same.

WO 2010/037061 describes transgenic and non-transgenic plants with improved tolerance to AHAS-inhibiting herbicides such as an oilseed rape which is tolerant towards one specific class of ALS inhibitors, the Imidazolinone herbicides.

Tan et al. (Pest. Manag. Sci (2005), 61: 246-257) inter alia refers to imidazolinone-tolerant oilseed rape.

As it relates to the compounds known acting as ALS inhibitor herbicides, these can be grouped in several classes.

Compounds from the group of the (sulfon)amides are already known as herbicidally active compounds for controlling unwanted vegetation; see, for example, EP 239414, U.S. Pat. No. 4,288,244, DE 3303388, U.S. Pat. No. 5,457,085, U.S. Pat. No. 3,120,434, U.S. Pat. No. 3,480,671, EP 206251, EP 205271, U.S. Pat. No. 2,556,664, U.S. Pat. No. 3,534,098, EP 53011, U.S. Pat. No. 4,385,927, EP 348737, DE 2822155, U.S. Pat. No. 3,894,078, GB 869169, EP 447004, DE 1039779, HU 176582, U.S. Pat. No. 3,442,945, DE 2305495, DE 2648008, DE 2328340, DE 1014380, HU 53483, U.S. Pat. No. 4,802,907, GB1040541, U.S. Pat. No. 2,903,478, U.S. Pat. No. 3,177,061, U.S. Pat. No. 2,695,225, DE 1567151, GB 574995, DE 1031571, U.S. Pat. No. 3,175,897, JP 1098331, U.S. Pat. No. 2,913,327, WO 8300329, JP 80127302, DE 1300947, DE 2135768, U.S. Pat. No. 3,175,887, U.S. Pat. No. 3,836,524, JP 85067463, U.S. Pat. No. 3,582,314, U.S. Pat. No. 53,330,821, EP 131258, U.S. Pat. No. 4,746,353, U.S. Pat. No. 4,420,325, U.S. Pat. No. 4,394,506, U.S. Pat. No. 4,127,405, U.S. Pat. No. 4,479,821, U.S. Pat. No. 5,009,699, EP 136061, EP 324569, EP 184385, WO 2002030921, WO 09215576, WO 09529899, U.S. Pat. No. 4,668,277, EP 305939, WO 09641537, WO 09510507, EP 7677, CN 01080116, U.S. Pat. No. 4,789,393, EP 971902, U.S. Pat. No. 5,209,771, EP 84020, EP 120814, EP 87780, WO 08804297, EP 5828924, WO 2002036595, U.S. Pat. No. 5,476,936, WO 2009/053058 and the literature cited in the publications mentioned above.

Compounds from the group of the imidazolinones are already known as herbicidally active compounds for controlling unwanted vegetation; see, for example Proc. South. Weed Sci. Soc. 1992. 45, 341, Proc. South. Weed Sci. Soc. Annu. Mtg. 36th, 1983, 29, Weed Sci. Soc. Annu. Mtg. 36th, 1983, 90-91, Weed Sci. Soc. Mtg., 1984, 18, Modern Agrochemicals, 2004, 14-15.

Compounds from the group of the pyrimidinyl(thio)benzoates are already known as herbicidally active compounds for controlling unwanted vegetation; see, for example U.S. Pat. No. 4,906,285, EP 658549, U.S. Pat. No. 5,118,339, WO 91/05781, U.S. Pat. No. 4,932,999, and EP 315889.

Compounds from the group of the sulfonanilids are already known as herbicidally active compounds for controlling unwanted vegetation; see, for example WO 93/09099, WO 2006/008159, and WO 2005/096818.

For example, the majority of European cars and trucks run on diesel fuel and an estimated 66% of total rapeseed oil supply in the European Union is expected to be used for biodiesel production in the next years. Rapeseed oil is the preferred oil stock for biodiesel production in most of Europe, accounting for about 80% of the feedstock (partly because rapeseed produces more oil per unit of land area compared to other oil sources, such as soy beans). Thus, it would be highly desirable to use one or more ALS inhibitor herbicides for control of unwanted vegetation in *B. napus* plants which are tolerant to such ALS inhibitor herbicides.

This problem was solved according to present invention.

The present invention relates to the use of one or more ALS inhibitor herbicide(s) for controlling unwanted vegetation in *Brassica* growing area, preferably *B. napus* growing area, which *Brassica* plants, preferably *B. napus* plants, comprise an altered ALS I *Brassica*, preferably *B. napus*, polypeptide comprising an amino acid different from an amino acid corresponding to at least one position selected from the group consisting of alanine205 (A205), trypthophane574 (W574), serine653 (S653) and glycine654 (G654) of SEQ ID NO: 10; and an altered ALS III *Brassica*, preferably *B. napus*, polypeptide comprising an amino acid different from an amino acid corresponding to at least one position selected from the group consisting of alanine205 (A205), trypthophane574 (W574), serine653 (S653) and glycine654 (G654) of SEQ ID NO: 10.

SUMMARY

One aspect of the present invention refers to the use of one or more ALS inhibitor herbicide(s) for controlling unwanted vegetation in *Brassica* growing area, preferably *B. napus* growing area, which *Brassica* plants, preferably *B. napus* plants, comprise an altered ALS I *Brassica*, preferably *B. napus*, polypeptide comprising an amino acid different from an amino acid corresponding to at least one position selected from the group consisting of alanine205 (A205), trypthophane574 (W574), serine653 (S653) and glycine654 (G654) of SEQ ID NO: 10; and an altered ALS III *Brassica*, preferably *B. napus*, polypeptide comprising an amino acid different from an amino acid corresponding to at least one position selected from the group consisting of alanine205 (A205), trypthophane574 (W574), serine653 (S653) and glycine654 (G654) of SEQ ID NO: 10.

One embodiment refers to the use according to the invention, wherein the ALS inhibitor herbicide(s) belong(s) to: the group of the (sulfon)amides (group (A)) consisting of: the subgroup (A1) of the sulfonylureas, consisting of: amidosulfuron [CAS RN 120923-37-7] (=A1-1); azimsulfuron [CAS RN 120162-55-2] (=A1-2); bensulfuron-methyl [CAS RN 83055-99-6] (=A1-3); chlorimuron-ethyl [CAS RN 90982-32-4] (=A1-4); chlorsulfuron [CAS RN 64902-72-3] (=A1-5); cinosulfuron [CAS RN 94593-91-6] (=A1-6); cyclosulfamuron [CAS RN 136849-15-5] (=A1-7);

ethametsulfuron-methyl [CAS RN 97780-06-8] (=A1-8); ethoxysulfuron [CAS RN 126801-58-9] (=A1-9); flazasulfuron [CAS RN 104040-78-0] (=A1-10); flucetosulfuron [CAS RN 412928-75-7] (=A1-11); flupyrsulfuron-methyl-sodium [CAS RN 144740-54-5] (=A1-12); foramsulfuron [CAS RN 173159-57-4] (=A1-13); halosulfuron-methyl [CAS RN 100784-20-1] (=A1-14); imazosulfuron [CAS RN 122548-33-8] (=A1-15); iodosulfuron-methyl-sodium [CAS RN 144550-36-7] (=A1-16); mesosulfuron-methyl [CAS RN 208465-21-8] (=A1-17); metsulfuron-methyl [CAS RN 74223-64-6] (=A1-18); monosulfuron [CAS RN 155860-63-2] (=A1-19); nicosulfuron [CAS RN 111991-09-4] (=A1-20); orthosulfamuron [CAS RN 213464-77-8] (=A1-21); oxasulfuron [CAS RN 144651-06-9] (=A1-22); primisulfuron-methyl [CAS RN 86209-51-0] (=A1-23); prosulfuron [CAS RN 94125-34-5] (=A1-24); pyrazosulfuron-ethyl [CAS RN 93697-74-6] (=A1-25); rimsulfuron [CAS RN 122931-48-0] (=A1-26); sulfometuron-methyl [CAS RN 74222-97-2] (=A1-27); sulfosulfuron [CAS RN 141776-32-1] (=A1-28); thifensulfuron-methyl [CAS RN 79277-27-3] (=A1-29); triasulfuron [CAS RN 82097-50-5] (=A1-30); tribenuron-methyl [CAS RN 101200-48-0] (=A1-31); trifloxysulfuron [CAS RN 145099-21-4] (sodium) (=A1-32); triflusulfuron-methyl [CAS RN 126535-15-7] (=A1-33); tritosulfuron [CAS RN 142469-14-5] (=A1-34); NC-330 [CAS RN 104770-29-8] (=A1-35); NC-620 [CAS RN 868680-84-6] (=A1-36); TH-547 [CAS RN 570415-88-2] (=A1-37); monosulfuron-methyl [CAS RN 175076-90-1] (=A1-38); 2-iodo-N-[(4-methoxy-6-methyl-1,3,5-triazinyl)carbamoyl] benzene-sulfonamide (=A1-39); a compound of the general formula (I)

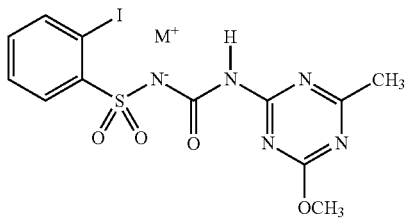

(I)

where M$^+$ denotes the respective salt of the compound (I), i.e. its lithium salt (=A1-40); its sodium salt (=A1-41); its potassium salt (=A1-42); its magnesium salt (=A1-43); its calcium (=A1-44); its ammonium salt (=A1-45); its methylammonium salt (=A1-46); its dimethylammonium salt (=A1-47); its tetramethylammonium salt (=A1-48); its ethylammonium salt (=A1-49); its diethylammonium salt (=A1-50); its tetraethylammonium salt (=A1-51); its propylammonium salt (=A1-52); its tetrapropylammonium salt (=A1-53); its isopropylammonium salt (=A1-54); its diisopropylammonium salt (=A1-55); its butylammonium salt (=A1-56); its tetrabutylammonium salt (=A1-57); its (2-hydroxyeth-1-yl)ammonium salt (=A1-58); its bis-N,N-(2-hydroxyeth-1-yl)ammonium salt (=A1-59); its tris-N,N,N-(2-hydroxyeth-1-yl)ammonium salt (=A1-60); its 1-phenylethylammonium salt (=A1-61); its 2-phenylethylammonium salt (=A1-62); its trimethylsulfonium salt (=A1-63); its trimethyloxonium salt (=A1-64); its pyridinium salt (=A1-65); its 2-methylpyridinium salt (=A1-66); its 4-methylpyridinium salt (=A1-67); its 2,4-dimethylpyridinium salt (=A1-68); its 2,6-dimethylpyridinium salt (=A1-69); its piperidinium salt (=A1-70); its imidazolium salt (=A1-71); its morpholinium salt (=A1-72); its 1,5-diazabicyclo[4.3.0]non-7-enium salt (=A1-73); its 1,8-diazabicyclo[5.4.0]undec-7-enium salt (=A1-74);

or a compound of the formula (II) or salts thereof

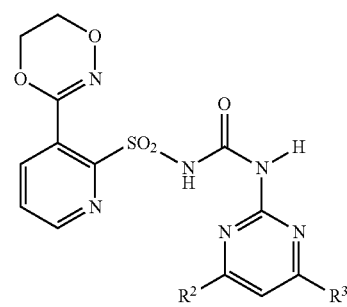

(II)

with R$^2$, and R$^3$ having the meaning as defined in the below table

| Compound | R$^2$ | R$^3$ |
| --- | --- | --- |
| A1-75 | OCH$_3$ | OC$_2$H$_5$ |
| A1-76 | OCH$_3$ | CH$_3$ |
| A1-77 | OCH$_3$ | C$_2$H$_5$ |
| A1-78 | OCH$_3$ | CF$_3$ |
| A1-79 | OCH$_3$ | OCF$_2$H |
| A1-80 | OCH$_3$ | NHCH$_3$ |
| A1-81 | OCH$_3$ | N(CH$_3$)$_2$ |
| A1-82 | OCH$_3$ | Cl |
| A1-83 | OCH$_3$ | OCH$_3$ |
| A1-84 | OC$_2$H$_5$ | OC$_2$H$_5$ |
| A1-85 | OC$_2$H$_5$ | CH$_3$ |
| A1-86 | OC$_2$H$_5$ | C$_2$H$_5$ | or the compound of formula (III) (=A1-87), i.e. the sodium salt of compound (A1-83)

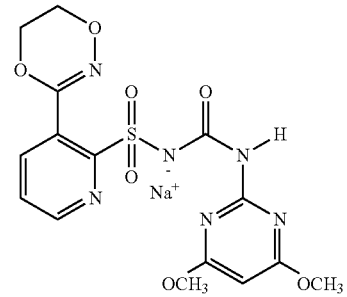

(III)

or the compound of formula (IV) (=A1-88), i.e. the sodium salt of compound (A1-82)

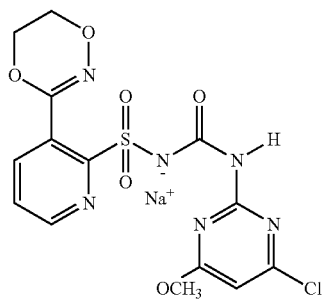

(IV)

the subgroup of the sulfonylaminocarbonyltriazolinones (subgroup ((A2)), consisting of: flucarbazone-sodium [CAS RN 181274-17-9] (=A2-1); propoxycarbazone-sodium [CAS RN 181274-15-7] (=A2-2); thiencarbazone-methyl [CAS RN 317815-83-1] (=A2-3);

the subgroup of the triazolopyrimidines (subgroup (A2)), consisting of: cloransulam-methyl [147150-35-4] (=A3-1); diclosulam [CAS RN 145701-21-9] (=A3-2); florasulam [CAS RN 145701-23-1] (=A3-3); flumetsulam [CAS RN 98967-40-9] (=A3-4); metosulam [CAS RN 139528-85-1] (=A3-5); penoxsulam [CAS RN 219714-96-2] (=A3-6); pyroxsulam [CAS RN 422556-08-9] (=A3-7);

the subgroup of the sulfonanilides (subgroup (A4)), consisting of: compounds or salts thereof from the group described by the general formula (I):

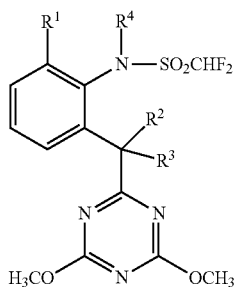

(V)

in which $R^1$ is halogen, preferably fluorine or chlorine, $R^2$ is hydrogen and $R^3$ is hydroxyl or $R^2$ and $R^3$ together with the carbon atom to which they are attached are a carbonyl group C=O and $R^4$ is hydrogen or methyl;

and more especially compounds of the below given chemical structure (A4-1) to (A4-8)

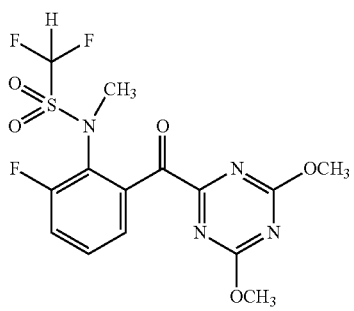

(A4-1)

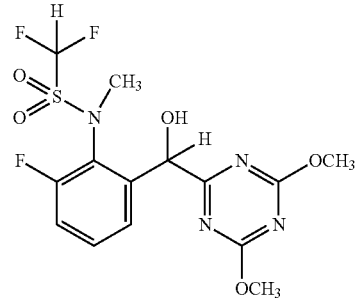

(A4-2)

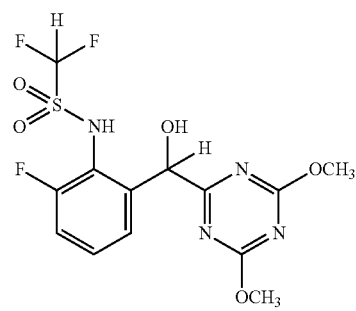

(A4-3)

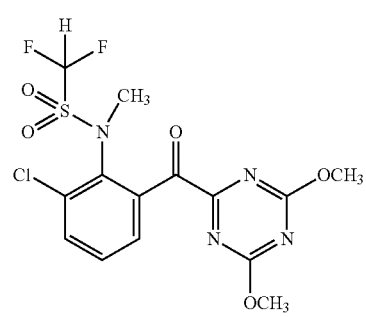

(A4-4)

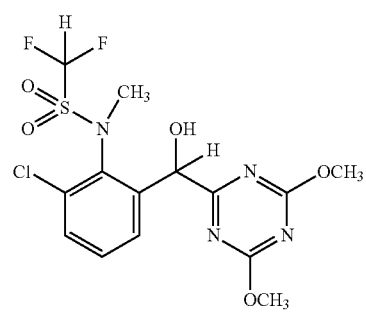

(A4-5)

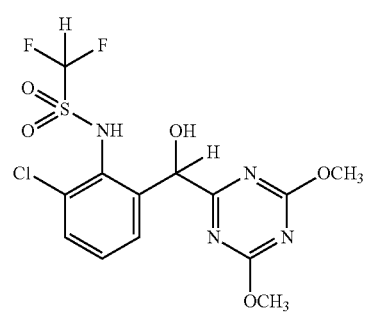

(A4-6)

-continued (A4-7)

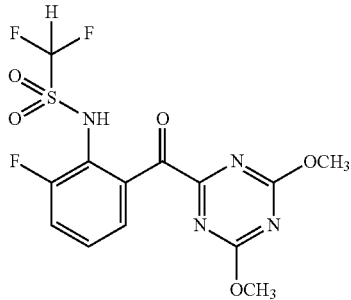

(A4-8)

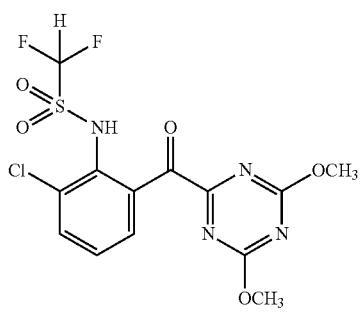

the group of the imidazolinones (group (B)), consisting of:
imazamethabenzmethyl [CAS RN 81405-85-8] (=B1-1); imazamox [CAS RN 114311-32-9] (=B1-2); imazapic [CAS RN 104098-48-8] (=B1-3); imazapyr [CAS RN 81334-34-1] (=B1-4); imazaquin [CAS RN 81335-37-7] (=B1-5); imazethapyr [CAS RN 81335-77-5] (=B1-6); SYP-298 [CAS RN 557064-77-4] (=B1-7); and SYP-300 [CAS RN 374718-10-2] (=B1-8);
the group of the pyrimidinyl(thio)benzoates (group (C)), consisting of:
the subgroup of the pyrimidinyloxybenzoeacids (subgroup (C1)) consisting of: bispyribac-sodium [CAS RN 125401-92-5] (=C1-1); pyribenzoxim [CAS RN 168088-61-7] (=C1-2); pyriminobac-methyl [CAS RN 136191-64-5] (=C1-3); pyribambenz-isopropyl [CAS RN 420138-41-6] (=C1-4); and pyribambenz-propyl [CAS RN 420138-40-5] (=C1-5);
the subgroup of the pyrimidinylthiobenzoeacids (subgroup (C2)), consisting of: pyriftalid [CAS RN 135186-78-6] (=C2-1); and pyrithiobac-sodium [CAS RN 123343-16-8] (=C2-2).

Another embodiment refers to the use according to the invention, wherein the ALS inhibitor herbicide(s) belong(s) to the group consisting of: amidosulfuron [CAS RN 120923-37-7] (=A1-1); chlorimuron-ethyl [CAS RN 90982-32-4] (=A1-4); chlorsulfuron [CAS RN 64902-72-3] (=A1-5); ethametsulfuron-methyl [CAS RN 97780-06-8] (=A1-8); ethoxysulfuron [CAS RN 126801-58-9] (=A1-9); flupyrsulfuron-methyl-sodium [CAS RN 144740-54-5] (=A1-12); foramsulfuron [CAS RN 173159-57-4] (=A1-13); iodosulfuron-methyl-sodium [CAS RN 144550-36-7] (=A1-16); mesosulfuron-methyl [CAS RN 208465-21-8] (=A1-17); metsulfuron-methyl [CAS RN 74223-64-6] (=A1-18); monosulfuron [CAS RN 155860-63-2] (=A1-19); nicosulfuron [CAS RN 111991-09-4] (=A1-20); rimsulfuron [CAS RN 122931-48-0] (=A1-26); sulfosulfuron [CAS RN 141776-32-1] (=A1-28); thifensulfuron-methyl [CAS RN 79277-27-3] (=A1-29); tribenuron-methyl [CAS RN 101200-48-0] (=A1-31); triflusulfuron-methyl [CAS RN 126535-15-7] (=A1-33); 2-iodo-N-[(4-methoxy-6-methyl-1,3,5-triazinyl)carbamoyl] benzene-sulfonamide (=A1-39); 2-iodo-N-[(4-methoxy-6-methyl-1,3,5-triazinyl)carbamoyl]benzene-sulfonamide sodium salt (=A1-41); (A1-83) or its sodium salt (=A1-87); flucarbazone-sodium [CAS RN 181274-17-9] (=A2-1); propoxycarbazone-sodium [CAS RN 181274-15-7] (=A2-2); thiencarbazone-methyl [CAS RN 317815-83-1] (=A2-3); florasulam [CAS RN 145701-23-1] (=A3-3); metosulam [CAS RN 139528-85-1] (=A3-5); pyroxsulam [CAS RN 422556-08-9] (=A3-7); (A4-1); (A4-2); (A4-3); imazamox [CAS RN 114311-32-9] (=B1-2); and bispyribac-sodium [CAS RN 125401-92-5] (=C1-1).

Another embodiment refers to the use according to the present invention, wherein the ALS inhibitor herbicide(s) belong(s) to the group consisting of: amidosulfuron [CAS RN 120923-37-7] (=A1-1); foramsulfuron [CAS RN 173159-57-4] (=A1-13); sodium salt of compound of formula (I) (=A1-41); compound of formula (III) (=A1-41); thiencarbazone-methyl [CAS RN 317815-83-1] (=A2-3); imazamox [CAS RN 114311-32-9] (=B1-2); and bispyribac-sodium [CAS RN 125401-92-5] (=C1-1).

Yet another embodiment refers to the use according to the present invention, wherein the Brassica plants are B. napus plants comprising an ALS I B. napus polypeptide containing an amino acid different from alanine at a position of said ALS I B. napus polypeptide corresponding to position 190 of SEQ ID NO: 2, and wherein an ALS III B. napus polypeptide containing an amino acid different from tryptophan at a position of said ALS III polypeptide corresponding to position 556 of SEQ ID NO: 4.

Yet another embodiment refers to the use according to the present invention, wherein the ALS inhibitor herbicide(s) are used in combination with non-ALS inhibitor herbicides (i.e. herbicides showing a mode of action that is different to the inhibition of the ALS enzyme [acetohydroxyacid synthase; EC 2.2.1.6] (group D herbicides), and wherein the non ALS inhibitor herbicide(s) is/are selected form the group consisting of: acetochlor (=D1), carbetamide (=D56), fenoxaprop-P-ethyl (=D164), fluazifop-P-BCS 11-3055 foreign country text 04.05.2012 MK/RAK butyl (=D174), haloxyfop-P-methyl (=D222), metolachlor (=D275), dimethenamid (=D132), napropamide (=D290), pethoxamid (=D317), propaquizafop (=D341), propisochlor (=D344), propyzamide (=D345), quinmerac (=D363), propachlor (D 427), clomazone (=D83), clopyralid (=D86), dimethachlor (=D130), metazachlor (=D265), picloram (=D321), and quizalofop-P-ethyl (=D368).

Yet another embodiment refers to the use according to the present invention, wherein the ALS inhibitor herbicide(s) are used in combination with non-ALS inhibitor herbicide(s) is/are selected form the group consisting of: clomazone (=D83), clopyralid (=D86), dimethachlor (=D130), metazachlor (=D265), picloram (=D321), and quizalofop-P-ethyl (=D368).

Another aspect of the present invention refers to a method for controlling unwanted vegetation in Brassica, preferably B. napus, plant growing areas by applying one or more ALS inhibitor herbicide(s) alone or in combination with one or more herbicide(s) that do(es) not belong to the class of ALS inhibitor herbicides for weed control in Brassica growing areas, preferably B. napus growing areas, which Brassica plants, preferably B. napus plants, comprise an altered ALS I Brassica, preferably B. napus, polypeptide comprising an amino acid different from an amino acid corresponding to at least one position selected from the group consisting of alanine205 (A205), trypthophane574 (W574), serine653 (S653) and glycine654 (G654) of SEQ ID NO: 10; and an altered ALS III Brassica, preferably B. napus, polypeptide comprising an amino acid different from an amino acid corresponding to at least one position selected from the group consisting alanine205 (A205), trypthophane574 (W574), serine653 (S653) and glycine654 (G654) of SEQ ID NO: 10.

One embodiment refers to a method according to the present invention for controlling unwanted vegetation, and wherein the ALS inhibitor herbicide(s) are taken from the groups as defined in [0028].

One embodiment refers to a method according to the present invention, and wherein the ALS inhibitor herbicide(s) are taken from the groups as defined in [0029].

One embodiment refers to a method according to the present invention, and wherein the non ALS inhibitor herbicide(s) are taken from the group as defined in [0032].

One embodiment refers to a method according to the present invention, and wherein the non ALS inhibitor herbicide(s) are taken from the group as defined in [0033].

BRIEF DESCRIPTION OF THE SEQUENCES

*A. thaliana* sequences SEQ ID NOs: 9 (nucleotide AY042819) and 10 (protein AAK68759), and wild type *B. napus* sequences SEQ ID NOs: 1 (ALS1 nucleotide Z11524) and 3 (ALS3 nucleotide Z11526) were taken from the ncbi-genebank (see world wide web: http://www.ncbi.nlm.nih.gov/genbank/). SEQ ID NOs: 2 and 4 are the protein sequences encoded by SEQ ID NOs: 1 and 3, respectively.

SEQ ID No. 1: Nucleic acid sequence encoding *B. napus* wild type ALS I gb Z11524.

SEQ ID No. 2: *B. napus* ALS I amino acid sequence derived from SEQ ID No. 1.

SEQ ID No. 3: Nucleic acid sequence encoding *B. napus* wild type ALS III gb Z11526.

SEQ ID No. 4: *B. napus* ALS III amino acid sequence derived from SEQ ID No. 3.

SEQ ID No. 5: Nucleic acid sequence encoding *B. napus* ALS I protein containing an A190V mutation.

SEQ ID No. 6: *B. napus* A190V ALS1 amino acid sequence derived from SEQ ID No. 5 (position 190 of SEQ ID NO: 6 corresponds to position 205 of SEQ ID NO: 10).

SEQ ID No. 7: Nucleic acid sequence encoding *B. napus* ALS III protein containing an W556L mutation.

SEQ ID No. 8: *B. napus* W556L ALS3 amino acid sequence derived from SEQ ID No. 7 (position 556 of SEQ ID NO: 8 corresponds to position 574 of SEQ ID NO: 10).

SEQ ID No. 9: Nucleic acid sequence encoding *A. thaliana* ALS gene.

SEQ ID No. 10: *A. thaliana* amino acid sequence derived from SEQ ID No. 9.

BRIEF DESCRIPTION OF THE DRAWINGS

FIGS. 1A-1D: Alignment of SEQ ID Nos: 9, 5, 1, 3, 7
FIGS. 2A-2B: Alignment of SEQ ID Nos: 10, 2, 6, 4, 8

DETAILED DESCRIPTION OF A PREFERRED EMBODIMENT

It must be noted that as used herein, the terms "a", "an", and "the", include singular and plural references unless the context clearly indicates otherwise, i.e., such terms may refer to "one", "one or more" or "at least one". Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Plant

The term "*Brassica*" (abbreviation "B.") or "*Brassica* plant" (abbreviation "B. plant") as used herein refers to the genus of plants in the mustard family (Brassicaceae). The members of the genus may be collectively known either as cabbages, or as mustards. The genus "*Brassica*" encompasses, e.g., *B. carinata, B. elongata, B. fruticulosa, B. juncea, B. napu, B. narinosa, B. nigra, B. oleracea, B. perviridis, B. rapa, B. rupestris, B. septiceps,* and *B. tournefortii*. The skilled person will understand that the term not only encompasses *B. napus* but also other hybrids which have at least one parent plant of the genus "*Brassica*".

When used herein the term "*Brassica napus*" is abbreviated as "*B. napus*". Furthermore, the term "oilseed rape" is used herein. Said three terms are interchangeably used and should be understood to fully comprise the cultivated forms of *B. napus* as defined in, e.g., Tang et al, Plant Breeding, Volume 116, Issue 5, pages 471-474, October 1997 and Jesske et al., Tagung der Vereinigung der Pflanzenzüchter and Saatgutkaufleute Österreichs, 2009, 171-172, ISBN: 978-3-902559-37-1). Similarly, for example, the term "*Arabidopsis thaliana*" is abbreviated as "*A. thaliana*". Both terms are interchangeably used herein.

In the present invention, *Brassica* plants, preferably oilseed rape (*B. napus*) plants, are described which comprise an altered ALS I polypeptide comprising an amino acid different from an amino acid corresponding to at least one position selected from the group consisting of alanine205 (A205), trypthophane574 (W574), serine653 (S653) and glycine654 (G654) of SEQ ID NO: 10; and an altered ALS III polypeptide conta carrying a point mutation at a position corresponding to at least one position from the group selected from A205, W574, S653 and G654 of SEQ ID NO: 10.

In one embodiment, *Brassica* plants, such as oilseed rape (*B. napus*) plants, are described which comprise non-transgenic mutations of its endogenous ALS genes, wherein an ALS I gene encodes an ALS I polypeptide comprising at least one amino acid different from those of positions selected from the group consisting of A205, W574, S653 and G654 of SEQ ID NO: 10; and wherein an ALS III gene encodes an ALS III polypeptide comprising at least one amino acid different from those of positions selected from the group consisting of A205, W574, S653 and G654 of SEQ ID NO: 10. In one embodiment, said *Brassica* plants comprise non-transgenic mutations of its endogenous ALS genes, wherein an ALS I gene encodes an ALS I polypeptide comprising at least one amino acid different from those of positions selected from the group consisting of A205, W574, S653 and G654 of SEQ ID NO: 10; and wherein an ALS III gene encodes an ALS III polypeptide comprising at least one amino acid different from those of positions selected from the group consisting of A205, W574, S653 and G654 of SEQ ID NO: 10 with the proviso that the at least one amino acid different from S653 is not asparagine if the at least one amino acid different from W574 is leucine.

In one embodiment, oilseed rape (*B. napus*) plants are described comprising an ALS I polypeptide containing an amino acid different from alanine at a position of said ALS I polypeptide corresponding to position 190 of SEQ ID NO: 2 (this equals position 205 of the referenced *Arabidopsis thaliana* sequence as shown in SEQ ID NO: 10) and an ALS III polypeptide containing an amino acid different from tryptophan at a position of said ALS III polypeptide corresponding to position 556 of SEQ ID NO: 4 (this equals position 574 of the referenced *Arabidopsis thaliana* sequence as shown in SEQ ID NO: 10).

In one embodiment, oilseed rape (*B. napus*) plants are described comprising an altered ALS I gene having a codon encoding an amino acid different from Ala, preferably Val, at a position corresponding to position 190 of SEQ ID NO: 2 (position 205 of SEQ ID NO: 10) and an altered oilseed rape ALS III gene having a codon encoding an amino acid different from Trp, preferably Leu, at a position corresponding to position 556 of SEQ ID NO: 4 (position 574 of SEQ ID NO: 10).

For example, seeds of plants in accordance with the present invention comprising an ALS I gene of SEQ ID NO 5 and an ALS III gene of SEQ ID NO: 7 were deposited with the NCIMB, Aberdeen, UK, under Number NCIMB 41813.

Due to the fact that the mutated *B. napus* plants described herein are herbicide resistant and were generated by "random evolution", i.e., methods preferably leading to fertile *Brassica* plants, preferably *B. napus* plants, having two point mutation as described herein in more detail without exogenous genetic manipulation, they are non-transgenic as far as the ALS gene in its endogenous gene locus is concerned.

The term "wild-type" as used herein refers to a plant, a nucleic acid molecule or protein that can be found in nature as distinct from being artificially produced or mutated by man. Thus, in one embodiment, a "wild type" *Brassica*, preferably *B. napus*, plant does not produce or comprise ALS proteins with an amino acid different from alanine205 (A205), tryptophane574 (W574), serine653 (S653) and glycine654 (G654) (the amino acids and the numbers following the amino acids indicate the amino acids and their position corresponding to these positions of SEQ ID NO: 10).

In one embodiment, a "wild-type" *B. napus* plant refers to a *B. napus* plant having at least one AHAS nucleic acid sequence of SEQ ID NO: 1 and at least one AHAS nucleic acid sequence of SEQ ID NO: 3. The use of the term "wild-type" is not intended to necessarily imply that a plant, plant tissue, plant cell, or other host cell lacks recombinant DNA in its genome, and/or does not possess herbicide resistant characteristics that are different from those disclosed herein. However, a wild type plant does not comprise an ALS I gene carrying a point mutation in the Ala190 codon (in relation to the *B. napus* ALS wild type amino acid sequence shown in SEQ ID NO: 2; this equals position 205 of the referenced *Arabidopsis thaliana* sequence as shown in SEQ ID NO: 10) yielding in an amino acid different from Ala, and an ALS III gene carrying a point mutation in the Trp556 codon (in relation to the *B. napus* ALS amino acid wild type sequence shown in SEQ ID NO: 4; this equals position 574 of the referenced *A. thaliana* sequence as shown in SEQ ID NO: 10) yielding in an amino acid different from Trp.

An "amino acid different from alanine" ("Ala" or "A") includes any naturally-occurring amino acid different from Ala. These naturally-occurring amino acids include neutral-nonpolar amino acids trypthophan (W), valine (V), methionine (M), isoleucine (I), leucine (L), proline (P), phenylalanine (F), basic amino acids arginine (R), lysine (K), histidine (H), polar/neutral amino acids aspartate (D), cysteine (C), glutamate (E), glycine (G), serine (S), threonine (T), tyrosine (Y) and acidic amino acids glutamine (Q) and asparagine (N).

In one embodiment, the "amino acid different from alanine" is an amino acid with physico-chemical properties different from alanine, i.e. belonging to any of the amino acids showing neutral-polar, acidic, or basic properties. In another embodiment, the amino acid different from alanine is another neutral-nonpolar amino acid. In one embodiment, such a neutral-nonpolar amino acid is valine, leucine or isoleucine. In another embodiment, said neutral-nonpolar amino acid is valine. In one embodiment, the amino acid different from alanine is glycine, isoleucine, leucine, methionine, phenylalanine, proline, valine, or arginine. In another embodiment, said amino acid different from alanine is valine, glycine, isoleucine, leucine, methionine, phenylalanine, proline or valine. In yet another embodiment, said amino acid different from alanine is valine, glycine, isoleucine or leucine. In even another embodiment, said amino acid different from alanine is valine, glycine and leucine. In one embodiment, said amino acid different from alanine is valine.

An "amino acid different from serine" ("Ser" or "S") includes any naturally-occurring amino acid different from Ser. These naturally-occurring amino acids include alanine (A), trypthophan (W), valine (V), methionine (M), isoleucine (I), leucine (L), proline (P), phenylalanine (F), arginine (R), lysine (K), histidine (H), aspartate (D), cysteine (C), glutamate (E), glycine (G), threonine (T), tyrosine (Y), glutamine (Q) and asparagine (N).

An "amino acid different from glycine" ("Gly" or "G") includes any naturally-occurring amino acid different from Gly. These naturally-occurring amino acids include alanine (A), trypthophan (W), valine (V), methionine (M), isoleucine (I), leucine (L), proline (P), phenylalanine (F), arginine (R), lysine (K), histidine (H), aspartate (D), cysteine (C), glutamate (E), serine (S), threonine (T), tyrosine (Y), glutamine (Q) and asparagine (N).

An "amino acid different from tryptophan" ("Trp" or "W") includes any naturally-occurring amino acid different from Trp. These naturally-occurring amino acids include alanine (A), arginine (R), asparagine (N), aspartate (D), cysteine (C), glutamine (Q), glutamate (E), glycine (G), histidine (H), isoleucine (I), leucine (L), lysine (K), methionine (M), phenylalanine (F), proline (P), tryptophan (W), threonine (T), tyrosine (Y) or valine (V).

In one embodiment, the amino acid different from tryptophan is an amino acid with physico-chemical properties different from tryptophan, i.e. belonging to any of the amino acids showing neutral-polar, acidic, or basic properties. In another embodiment, the amino acid different from tryptophan is another neutral-nonpolar amino acid. In one embodiment, the amino acid different from Trp is alanine, glycine, isoleucine, leucine, methionine, phenylalanine, proline, valine, and arginine. In another embodiment, said amino acid different from tryptophan is alanine, glycine, isoleucine, leucine, methionine, phenylalanine, proline or valine. In yet another embodiment, said amino acid different from tryptophan is alanine, glycine, isoleucine, leucine or valine. In even another embodiment, said amino acid different from tryptophan is glycine and leucine. In one embodiment, said amino acid different from tryptophan is leucine.

The making, selection and propagation of respective ALS inhibitor herbicide tolerant *Brassica* mutants and their progenies, especially respective ALS inhibitor herbicide tolerant *B. napus* mutants and their progenies that were also used in the biological examples disclosed subsequently, is described in detail in the European Patent Application having the title "ALS inhibitor herbicide tolerant *B. napus* mutants" and which was filed electronically on the same day (Apr. 5, 2011) at the European Patent Office as the present application and of which Bayer CropScience AG is an applicant, and which has received the Application number EP 11164720.2.

Therefore, these respective techniques concerning the preparation of such ALS inhibitor herbicide tolerant *B. napus* mutants comprising non-transgenic mutations of its endogenous acetolactate synthase (ALS) genes, wherein an ALS I gene encodes an ALS I polypeptide containing at least one amino acid different from a naturally occurring amino acid at a position corresponding to a position A205, W574, S653 or G654 of SEQ ID NO: 10 and wherein an ALS III gene encodes an ALS III polypeptide containing at least one amino acid different from a naturally occurring amino acid at a position corresponding to a position A205, W574, S653 or G654 of SEQ ID NO: 10 are described herein only in brief and the content; especially concerning the examples of the above cited patent application is referenced in its entirety.

Sequences/Position

The term "sequence" when used herein relates to nucleotide sequence(s), polynucleotide(s), nucleic acid sequence(s), nucleic acid(s), nucleic acid molecule, peptides, polypeptides and proteins, depending on the context in which the term "sequence" is used.

Generally, the skilled person knows, because of his common general knowledge and the context when the terms ALS, ALSL, AHAS or AHASL are used herein as to whether the nucleotide sequence or nucleic acid, or the amino acid sequence or polypeptide, respectively, is meant.

The term "position" when used in accordance with the present invention means the position of either an amino acid within an amino acid sequence depicted herein or the position of a nucleotide within a nucleotide sequence depicted herein. The term "corresponding" as used herein also includes that a position is not only determined by the number of the preceding nucleotides/amino acids.

The position of a given nucleotide in accordance with the present invention which may be substituted may vary due to deletions or additional nucleotides elsewhere in the ALS 5'-untranslated region (UTR) including the promoter and/or any other regulatory sequences or gene (including exons and introns) Similarly, the position of a given amino acid in accordance with the present invention which may be substituted may vary due to deletion or addition of amino acids elsewhere in the ALS polypeptide.

Thus, under a "corresponding position" or "position corresponding to aposition" in accordance with the present invention it is to be understood that nucleotides/amino acids may differ in the indicated number but may still have similar neighbouring nucleotides/amino acids. Said nucleotides/amino acids which may be exchanged, deleted or added are also comprised by the term "corresponding position".

In order to determine whether a nucleotide residue or amino acid residue in a given ALS nucleotide/amino acid sequence corresponds to a certain position in the nucleotide sequence of SEQ ID NO: 1, 3 or 9, respectively, or their corresponding amino acid sequences of SEQ ID NO: 2, 4 or 10, respectively, the skilled person can use means and methods well-known in the art, e.g., alignments, either manually or by using computer programs such as BLAST (Altschul et al. (1990), Journal of Molecular Biology, 215, 403-410), which stands for Basic Local Alignment Search Tool or ClustalW (Thompson et al. (1994), Nucleic Acid Res., 22, 4673-4680) or any other suitable program which is suitable to generate sequence alignments.

In one embodiment, SEQ ID NO: 1 is preferred as the reference nucleotide sequence for mutated ALS I *B. napus* protein encoding sequences such as SEQ ID NO: 5, and SEQ ID NO: 2 is preferred as the reference amino acid sequence fur mutated sequences such as SEQ ID NO: 6 in all of the subsequent disclosures.

Similarily, SEQ ID NO: 3 is preferred as the reference nucleotide sequence for mutated ALS III *B. napus* protein encoding sequences such as SEQ ID NO: 7 and SEQ ID NO: 4 is preferred as the reference amino acid sequence fur mutated sequences such as SEQ ID NO: 8 in all of the subsequent disclosures.

Thus, in any event, the equivalent position can still be determined through alignment with a reference sequence, such as SEQ II) NO: 1 or 5 (nucleotide sequence) or SEQ ID NO: 2 or 6 (amino acid sequence). Alignments of the various sequences listed above are given in FIGS. 1A-1D and 2A-2B In view of the difference between the *B.* (*napus*) wild-type ALS genes (ALS I and III gene) and the mutated *B.* (*napus*) ALS genes comprised by a *B.* (*napus*) plant of the present invention or progeny thereof, the ALS genes (or polynucleotides or nucleotide sequences) comprised by a *B.* (*napus*) plant of the present invention or progeny thereof may also be regarded as a "mutant ALS gene", "mutant ALS allele", "mutant ALS polynucleotide" or the like. Thus, throughout the specification, the terms "mutant allele", "mutant ALS allele", "mutant ALS gene" or "mutant ALS polynucleotide" are used interchangeably.

Unless indicated otherwise herein, these terms, when referring to *B. napus*, refer to a nucleotide sequence encoding an ALS I protein that comprises a codon at a position which corresponds to position 568-570 of SEQ ID NO: 1 and said codon encodes an amino acid different from alanine; and to a second nucleotide sequence encoding for an ALS III protein that comprises a codon at a position which corresponds to position 1666-1668 of SEQ ID NO: 3 and said codon of said second nucleotide sequence encodes an amino acid different from tryptophan.

Likewise, when referring to *Brassica*, these terms refer to nucleotide sequences that encodes an ALS I or ALS III *Brassica* protein having at least at a position corresponding to positions 205, 574, 653 and 654 of the amino acid sequence of *A. thaliana* (SEQ ID NO: 10) an amino acid different from an amino acid at this position in SEQ ID NO: 10. For example, FIGS. 1A-1D disclose an alignment of SEQ ID NOs: 9 (*A. thaliana*), 5 mutant ALS I gene *B. napus* (Ala190Val), 1 (wild type ALS I *B. napus*), 3 (wild type ALS III *B. napus*) and 7 mutant ALS III gene *B. napus* (Trp556Leu) to demonstrate one possible embodiment of the present invention. FIGS. 2A-2B disclose an alignment of the corresponding amino acid sequences.

The terms "nucleotide sequence(s)", "polynucleotide(s)", "nucleic acid sequence(s)", "nucleic acid(s)", "nucleic acid molecule" are used interchangeably herein and refer to nucleotides, either ribonucleotides or deoxyribonucleotides or a combination of both, in a polymeric unbranched form of any length. Nucleic acid sequences include DNA, cDNA, genomic DNA, RNA, synthetic forms and mixed polymers, both sense and antisense strands, or may contain non-natural or derivatized nucleotide bases, as will be readily appreciated by those skilled in the art.

Homology/Identity

In order to determine whether a nucleic acid sequence has a certain degree of identity to the nucleotide sequences of the present invention, the skilled person can use means and methods well-known in the art, e.g., alignments, either manually or by using computer programs such as those mentioned further down below in connection with the definition of the term "hybridization" and degrees of homology.

For the purpose of this invention, the "sequence identity" or "sequence homology" (the terms are used interchangeably herein) of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

The term *B. napus* "ALS" or "AHAS" gene also includes *B. napus* nucleotide sequences which are at least 60, 70, 80, 90, 95, 97, 98, or 99% identical to the *B. napus* ALS nucleotide sequence of SEQ ID NO: 1 or 3, wherein these 60, 70, 80, 90, 95, 97, 98, or 99% identical nucleotide sequences comprise at a position corresponding to position 568-570 of the nucleotide sequence of SEQ ID NO: 1 a codon encoding an amino acid different from Ala (at position 190 of SEQ ID NO: 2) or at a position corresponding to position 1666-1668 of the nucleotide sequence of SEQ ID NO: 3 a codon encoding an amino acid different from Trp (at position 556 of SEQ ID NO: 4).

Likewise, these at least 60, 70, 80, 90, 95, 97, 98, or 99% identical nucleotide sequences encode an ALS polypeptide comprising at a position corresponding to position 190 of SEQ ID NO: 2 an amino acid different from Ala, or at a position corresponding to position 556 of SEQ ID NO: 4 an amino acid different from Trp. Of course, these nucleotide sequences encode for ALS proteins which retains the activity as described herein, more preferably the thus-encoded ALS polypeptide is tolerant to one or more ALS inhibitor herbicides as described herein. Said term also includes allelic variants and homologs encoding an ALS polypeptide which is preferably tolerant to one or more ALS inhibitor herbicides as described herein.

When used herein, the term "polypeptide" or "protein" (both terms are used interchangeably herein) means a peptide, a protein, or a polypeptide which encompasses amino acid chains of a given length, wherein the amino acid residues are linked by covalent peptide bonds. However, peptidomimetics of such proteins/polypeptides wherein amino acid(s) and/or peptide bond(s) have been replaced by functional analogs are also encompassed by the invention as well as other than the 20 gene-encoded amino acids, such as selenocysteine. Peptides, oligopeptides and proteins may be termed polypeptides. The term polypeptide also refers to, and does not exclude, modifications of the polypeptide, e.g., glycosylation, acetylation, phosphorylation and the like. Such modifications are well described in basic texts and in more detailed monographs, as well as in the research literature. The polypeptide (or protein) that are preferably meant herein are the mutated *B. napus* ALS I and III polypeptidea (or ALS I and III proteins) of SEQ ID NO: 6 and 8, respectively.

The term *B. (napus)* "ALS" or "AHAS" polypeptide also includes amino acid sequences which are at least 90, 95, 97, 98, or 99% identical to the ALS amino acid sequence of the corresponding wild type, e.g., SEQ ID NOs: 2 or 4 for *B. napus*, wherein these at least 90, 95, 97, 98, or 99% identical amino acid sequences comprising at a position corresponding to position 205 of SEQ ID NO: 10 an amino acid different from alanine and at a position corresponding to position 574 of SEQ ID NO: 10 an amino acid different from tryptophan. Said X % identical amino acid sequences retain the activity of ALS as described herein, more preferably the ALS polypeptide is tolerant to ALS inhibitor herbicides as described herein. However, such "ALS" or "AHAS" polypeptides still show ALS activity of at least 20%, 30%, 40%, 50%, 60%, 70%, 80%, 90% compared to ALS activity of an protein having the SEQ ID NO: 2 (when referring to an ALS I protein) or 4 (when referring to an ALS III protein).

The same techniques, e.g., BLAST, as described above for the alignment of nucleic acid sequences can be used for alignments of protein sequences as well. For Example, a BLAST search can be perdormed from those skilled in the art using ExPASy (see world wide net: http://expasy.org/tools/).

Thus, in any event, the equivalent position could still be determined through alignment with a reference sequence, such as SEQ ID NO: 1 or 5 (nucleotide sequence) or SEQ ID NO: 2 or 6 (amino acid sequence).

Use

The present invention relates to the use of one or more ALS inhibitor herbicide(s) in *B. napus* mutants comprising non-transgenic mutations of its endogenous acetolactate synthase (ALS) genes, wherein an ALS I gene encodes an ALS I polypeptide containing an amino acid different from alanine at a position 190 of said ALS I polypeptide and wherein an ALS III gene encodes an ALS III polypeptide containing an amino acid different from tryptophan at a position 559 of said ALS III polypeptide and wherein the ALS inhibitor herbicide(s) belong to:

the group of the (sulfon)amides (group (A)) consisting of:
    the subgroup (A1) of the sulfonylureas, consisting of:
        amidosulfuron [CAS RN 120923-37-7] (=A1-1);
        azimsulfuron [CAS RN 120162-55-2] (=A1-2);
        bensulfuron-methyl [CAS RN 83055-99-6] (=A1-3);
        chlorimuron-ethyl [CAS RN 90982-32-4] (=A1-4);
        chlorsulfuron [CAS RN 64902-72-3] (=A1-5);
        cinosulfuron [CAS RN 94593-91-6] (=A1-6);
        cyclosulfamuron [CAS RN 136849-15-5] (=A1-7);
        ethametsulfuron-methyl [CAS RN 97780-06-8] (=A1-8);
        ethoxysulfuron [CAS RN 126801-58-9] (=A1-9);
        flazasulfuron [CAS RN 104040-78-0] (=A1-10);
        flucetosulfuron [CAS RN 412928-75-7] (=A1-11);
        flupyrsulfuron-methyl-sodium [CAS RN 144740-54-5] (=A1-12);
        foramsulfuron [CAS RN 173159-57-4] (=A1-13);
        halosulfuron-methyl [CAS RN 100784-20-1] (=A1-14);
        imazosulfuron [CAS RN 122548-33-8] (=A1-15);
        iodosulfuron-methyl-sodium [CAS RN 144550-36-7] (=A1-16);

mesosulfuron-methyl [CAS RN 208465-21-8] (=A1-17);
metsulfuron-methyl [CAS RN 74223-64-6] (=A1-18);
monosulfuron [CAS RN 155860-63-2] (=A1-19);
nicosulfuron [CAS RN 111991-09-4] (=A1-20);
orthosulfamuron [CAS RN 213464-77-8] (=A1-21);
oxasulfuron [CAS RN 144651-06-9] (=A1-22);
primisulfuron-methyl [CAS RN 86209-51-0] (=A1-23);
prosulfuron [CAS RN 94125-34-5] (=A1-24);
pyrazosulfuron-ethyl [CAS RN 93697-74-6] (=A1-25);
rimsulfuron [CAS RN 122931-48-0] (=A1-26);
sulfometuron-methyl [CAS RN 74222-97-2] (=A1-27);
sulfosulfuron [CAS RN 141776-32-1] (=A1-28);
thifensulfuron-methyl [CAS RN 79277-27-3] (=A1-29);
triasulfuron [CAS RN 82097-50-5] (=A1-30);
tribenuron-methyl [CAS RN 101200-48-0] (=A1-31);
trifloxysulfuron [CAS RN 145099-21-4] (sodium) (=A1-32);
triflusulfuron-methyl [CAS RN 126535-15-7] (=A1-33);
tritosulfuron [CAS RN 142469-14-5] (=A1-34);
NC-330 [CAS RN 104770-29-8] (=A1-35);
NC-620 [CAS RN 868680-84-6] (=A1-36);
TH-547 [CAS RN 570415-88-2] (=A1-37);
monosulfuron-methyl [CAS RN 175076-90-1] (=A1-38);
2-iodo-N-[(4-methoxy-6-methyl-1,3,5-triazinyflcarbamoyl]benzene-sulfonamide (=A1-39);
a compound of the general formula (I)

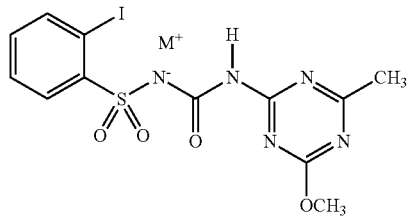
(I)

where M⁺ denotes the respective salt of the compound (I), i.e.
its lithium salt (=A1-40); its sodium salt (=A1-41); its potassium salt (=A1-42); its magnesium salt (=A1-43); its calcium (=A1-44); its ammonium salt (=A1-45); its methylammonium salt (=A1-46); its dimethylammonium salt (=A1-47); its tetramethylammonium salt (=A1-48); its ethylammonium salt (=A1-49); its diethylammonium salt (=A1-50); its tetraethylammonium salt (=A1-51); its propylammonium salt (=A1-52); its tetrapropylammonium salt (=A1-53); its isopropylammonium salt (=A1-54); its diisopropylammonium salt (=A1-55); its butylammonium salt (=A1-56); its tetrabutylammonium salt (=A1-57); its (2-hydroxyeth-1-yl)ammonium salt (=A1-58); its bis-N,N-(2-hydroxyeth-1-yl)ammonium salt (=A1-59); its tris-N,N,N-(2-hydroxyeth-1-yl)ammonium salt (=A1-60); its 1-phenylethylammonium salt (=A1-61); its 2-phenylethylammonium salt (=A1-62); its trimethylsulfonium salt (=A1-63); its trimethyloxonium salt (=A1-64); its pyridinium salt (=A1-65); its 2-methylpyridinium salt (=A1-66); its 4-methylpyridinium salt (=A1-67); its 2,4-dimethylpyridinium salt (=A1-68); its 2,6-dimethylpyridinium salt (=A1-69); its piperidinium salt (=A1-70); its imidazolium salt (=A1-71); its morpholinium salt (=A1-72); its 1,5-diazabicyclo[4.3.0]non-7-enium salt (=A1-73); its 1,8-diazabicyclo[5.4.0]undec-7-enium salt (=A1-74);

or a compound of the formula (II) or salts thereof

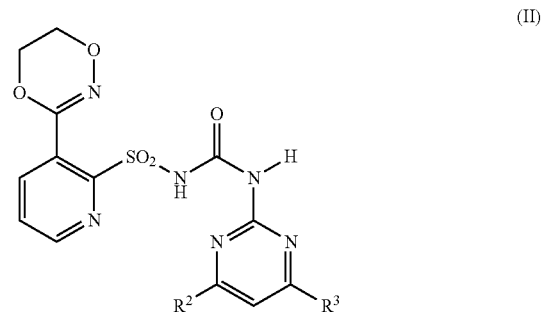
(II)

with R², and R³ having the meaning as defined in the below table

| Compound | R² | R³ |
|---|---|---|
| A1-75 | OCH₃ | OC₂H₅ |
| A1-76 | OCH₃ | CH₃ |
| A1-77 | OCH₃ | C₂H₅ |
| A1-78 | OCH₃ | CF₃ |
| A1-79 | OCH₃ | OCF₂H |
| A1-80 | OCH₃ | NHCH₃ |
| A1-81 | OCH₃ | N(CH₃)₂ |
| A1-82 | OCH₃ | Cl |
| A1-83 | OCH₃ | OCH₃ |
| A1-84 | OC₂H₅ | OC₂H₅ |
| A1-85 | OC₂H₅ | CH₃ |
| A1-86 | OC₂H₅ | C₂H₅ | or the compound of formula (III) (=A1-87), i.e. the sodium salt of compound (A1-83)

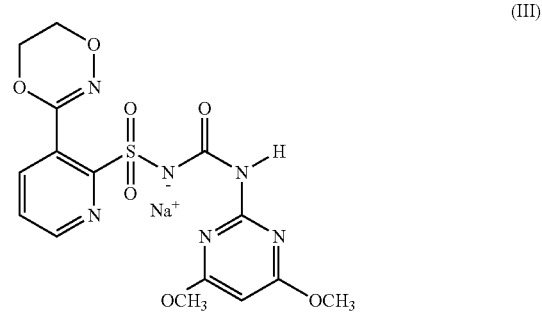 [SMILES: COc1cc(OC)nc(NC(=O)NS(=O)(=O)c2ncccc2C2=NOCCO2)n1 ; [Na+]]
(III)

or the compound of formula (IV) (=A1-88), i.e. the sodium salt of compound (A1-82).

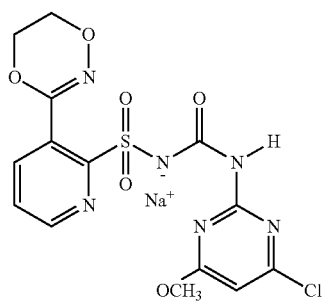
(IV)

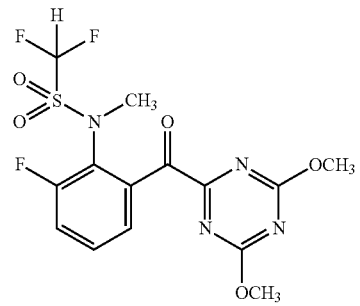
(A4-1)

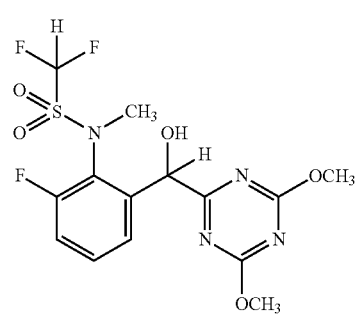
(A4-2)

the subgroup of the sulfonylaminocarbonyltriazolinones (subgroup ((A2)), consisting of:
  flucarbazone-sodium [CAS RN 181274-17-9] (=A2-1);
  propoxycarbazone-sodium [CAS RN 181274-15-7] (=A2-2);
  thiencarbazone-methyl [CAS RN 317815-83-1] (=A2-3);
the subgroup of the triazolopyrimidines (subgroup (A3)), consisting of:
  cloransulam-methyl [147150-35-4] (=A3-1);
  diclosulam [CAS RN 145701-21-9] (=A3-2);
  florasulam [CAS RN 145701-23-1] (=A3-3);
  flumetsulam [CAS RN 98967-40-9] (=A3-4);
  metosulam [CAS RN 139528-85-1] (=A3-5);
  penoxsulam [CAS RN 219714-96-2] (=A3-6);
  pyroxsulam [CAS RN 422556-08-9] (=A3-7);
the subgroup of the sulfonanilides (subgroup (A4)), consisting of:
  compounds or salts thereof from the group described by the general formula (I):

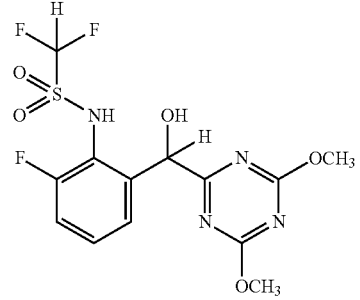
(A4-3)

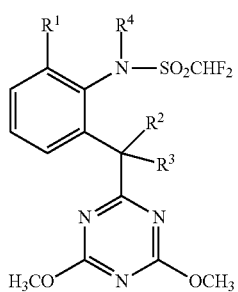
(V)

in which
R$^1$ is halogen, preferably fluorine or chlorine,
R$^2$ is hydrogen and R$^3$ is hydroxyl or
R$^2$ and R$^3$ together with the carbon atom to which they are attached are a carbonyl group C=O and
R$^4$ is hydrogen or methyl;
and more especially compounds of the below given chemical structure (A4-1) to (A4-8)

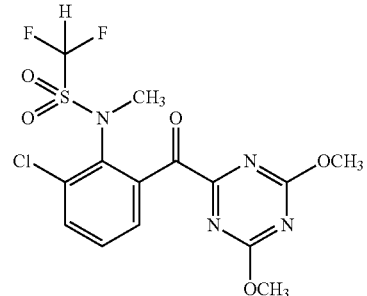
(A4-4)

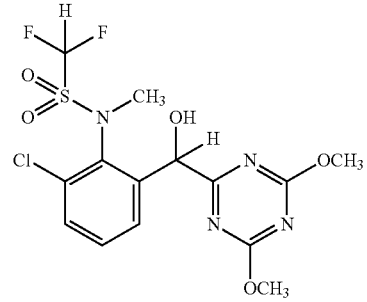
(A4-5)

-continued

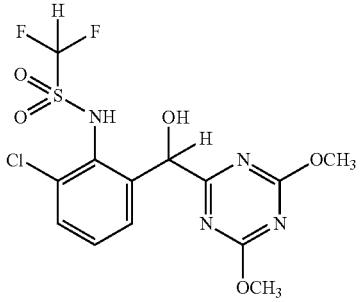

(A4-6)

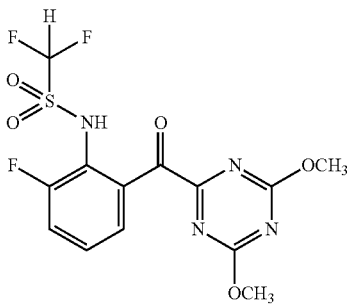

(A4-7)

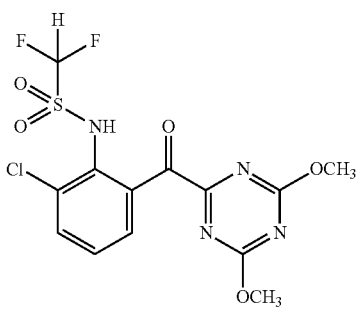

(A4-8)

the group of the imidazolinones (group (B1)), consisting of:
  imazamethabenzmethyl [CAS RN 81405-85-8] (=B1-1);
  imazamox [CAS RN 114311-32-9] (=B1-2);
  imazapic [CAS RN 104098-48-8] (=B1-3);
  imazapyr [CAS RN 81334-34-1] (=B1-4);
  imazaquin [CAS RN 81335-37-7] (=B1-5);
  imazethapyr [CAS RN 81335-77-5] (=B1-6);
  SYP-298 [CAS RN 557064-77-4] (=B1-7);
  SYP-300 [CAS RN 374718-10-2] (=B1-8).
the group of the pyrimidinyl(thio)benzoates (group (C)), consisting of:
  the subgroup of the pyrimidinyloxybenzoeacids (subgroup (C1)) consisting of:
    bispyribac-sodium [CAS RN 125401-92-5] (=C1-1);
    pyribenzoxim [CAS RN 168088-61-7] (=C1-2);
    pyriminobac-methyl [CAS RN 136191-64-5] (=C1-3);
    pyribambenz-isopropyl [CAS RN 420138-41-6] (=C1-4);
    pyribambenz-propyl [CAS RN 420138-40-5] (=C1-5);
  the subgroup of the pyrimidinylthiobenzoeacids (subgroup (C2)), consisting of:
    pyriftalid [CAS RN 135186-78-6] (=C2-1);
    pyrithiobac-sodium [CAS RN 123343-16-8] (=C2-2).

In this context, "tolerance" or "tolerant" means that the application of one or more ALS inhibitor herbicide(s) belonging to any of the above defined groups (A), (B), (C) does not show any apparent effect(s) concerning the physiological functions/phytotoxicity when applied to the respective *Brassica*, preferably *B. napus*, plant having non-transgenic mutations of its endogenous acetolactate synthase (ALS) genes, wherein the ALS I *Brassica*, preferably *B. napus*, gene encodes a first ALS *Brassica*, preferably *B. napus*, polypeptide containing an amino acid different from, e.g., alanine at a position corresponding to position 205 of SEQ ID NO: 10 and wherein the ALS III *Brassica*, preferably *B. napus*, gene encodes a second ALS III *Brassica*, preferably *B. napus*, polypeptide containing an amino acid different from tryptophan at a position corresponding to position 574 of SEQ ID NO: 10 and whereas the application of the same amount of the respective ALS inhibitor herbicide(s) on non-tolerant *Brassica*, preferably *B. napus*, wild type plants leads to significant negative effects concerning plant growth, its physiological functions or shows phytotoxic symptoms. For example, plants according to the present invention shows essentially no injury (injury less than 5%, 1% or no injury at all, i.e., 0%) when 15 g a.i./ha is applied to these plants whereas plants of variety SR002201 show more than 90% damage when treated in the same way. Qualtity and quantity of the observed effects may depend on the chemical composition of the respective ALS inhibitor heribicide(s) applied, dose rate and timing of the application as well growth conditions/stage of the treated plants.

The "CAS RN" stated in square brackets after the names (common names) mentioned under groups A to C corresponds to the "chemical abstract service registry number", a customary reference number which allows the substances named to be classified unambiguously, since the "CAS RN" distinguishes, inter alia, between isomers including stereoisomers.

ALS inhibitor herbicides which are preferably used for control of unwanted vegetation in *B. napus* growing areas which *B. napus* plants comprise non-transgenic mutations of its endogenous acetolactate synthase (ALS) genes, wherein the ALS I gene encodes an ALS I polypeptide containing an amino acid different from alanine at a position 190 of said first ALS I polypeptide and wherein the ALS III gene encodes an ALS III polypeptide containing an amino acid different from tryptophan at a position 559 of said ALS III polypeptide and thereby providing tolerance against the ALS inhibitor herbicide(s) according to this invention belonging to group (A) are:
amidosulfuron [CAS RN 120923-37-7] (=A1-1);
chlorimuron-ethyl [CAS RN 90982-32-4] (=A1-4);
chlorsulfuron [CAS RN 64902-72-3] (=A1-5);
ethametsulfuron-methyl [CAS RN 97780-06-8] (=A1-8);
ethoxysulfuron [CAS RN 126801-58-9] (=A1-9);
flupyrsulfuron-methyl-sodium [CAS RN 144740-54-5] (=A1-12);
foramsulfuron [CAS RN 173159-57-4] (=A1-13);
iodosulfuron-methyl-sodium [CAS RN 144550-36-7] (=A1-16);
mesosulfuron-methyl [CAS RN 208465-21-8] (=A1-17);
metsulfuron-methyl [CAS RN 74223-64-6] (=A1-18);
monosulfuron [CAS RN 155860-63-2] (=A1-19);
nicosulfuron [CAS RN 111991-09-4] (=A1-20);
rimsulfuron [CAS RN 122931-48-0] (=A1-26);
sulfosulfuron [CAS RN 141776-32-1] (=A1-28);
thifensulfuron-methyl [CAS RN 79277-27-3] (=A1-29);
tribenuron-methyl [CAS RN 101200-48-0] (=A1-31);
triflusulfuron-methyl [CAS RN 126535-15-7] (=A1-33);
2-iodo-N-[(4-methoxy-6-methyl-1,3,5-triazinyl)carbamoyl] benzene-sulfonamide (=A1-39);
2-iodo-N-[(4-methoxy-6-methyl-1,3,5-triazinyl)carbamoyl] benzene-sulfonamide sodium salt (=A1-41);
(A1-83) or its sodium salt (=A1-87);
flucarbazone-sodium [CAS RN 181274-17-9] (=A2-1);

propoxycarbazone-sodium [CAS RN 181274-15-7] (=A2-2);
thiencarbazone-methyl [CAS RN 317815-83-1] (=A2-3);
florasulam [CAS RN 145701-23-1] (=A3-3);
metosulam [CAS RN 139528-85-1] (=A3-5);
pyroxsulam [CAS RN 422556-08-9] (=A3-7);
(A4-1); (A4-2) and (A4-3).

ALS inhibitor herbicides which are more preferably used for control of unwanted vegetation in *B. napus* growing areas which *B. napus* plants are described herein comprise non-transgenic mutations of its endogenous acetolactate synthase (ALS) genes, wherein the ALS I gene encodes an ALS I polypeptide containing an amino acid different from alanine at a position 190 of said first ALS I polypeptide and wherein the ALS III gene encodes an ALS III polypeptide containing an amino acid different from tryptophan at a position 559 of said ALS III polypeptide and thereby providing tolerance against the ALS inhibitor herbicide(s) according to this invention belonging
to group (A) are:

amidosulfuron [CAS RN 120923-37-7] (=A1-1);
ethoxysulfuron [CAS RN 126801-58-9] (=A1-9);
flupyrsulfuron-methyl-sodium [CAS RN 144740-54-5] (=A1-12);
foramsulfuron [CAS RN 173159-57-4] (=A1-13);
iodosulfuron-methyl-sodium [CAS RN 144550-36-7] (=A1-16);
mesosulfuron-methyl [CAS RN 208465-21-8] (=A1-17);
metsulfuron-methyl [CAS RN 74223-64-6] (=A1-18);
nicosulfuron [CAS RN 111991-09-4] (=A1-20);
rimsulfuron [CAS RN 122931-48-0] (=A1-26);
sulfosulfuron [CAS RN 141776-32-1] (=A1-28);
thifensulfuron-methyl [CAS RN 79277-27-3] (=A1-29);
tribenuron-methyl [CAS RN 101200-48-0] (=A1-31);
the sodium salt of compound of formula (I) (=A1-41);
compound of formula (III) (=A1-87);
propoxycarbazone-sodium [CAS RN 181274-15-7] (=A2-2);
thiencarbazone-methyl [CAS RN 317815-83-1] (=A2-3);
florasulam [CAS RN 145701-23-1] (=A3-3);
metosulam [CAS RN 139528-85-1] (=A3-5); and
pyroxsulam [CAS RN 422556-08-9] (=A3-7).

ALS inhibitor herbicides which are especially preferably used for control of unwanted vegetation in *B. napus* growing areas which *B. napus* plants comprise non-transgenic mutations of its endogenous acetolactate synthase (ALS) genes, wherein the ALS I gene encodes an ALS I polypeptide containing an amino acid different from alanine at a position 190 of said first ALS I polypeptide and wherein the ALS III gene encodes an ALS III polypeptide containing an amino acid different from tryptophan at a position 559 of said ALS III polypeptide and thereby providing tolerance against the ALS inhibitor herbicide(s) according to this invention belonging to group (A) are:

amidosulfuron [CAS RN 120923-37-7] (=A1-1);
foramsulfuron [CAS RN 173159-57-4] (=A1-13);
sodium salt of compound of formula (I) (=A1-41);
compound of formula (III) (=A1-87); and
thiencarbazone-methyl [CAS RN 317815-83-1] (=A2-3).

Another ALS inhibitor herbicide which is preferably used for control of unwanted vegetation in *B. napus* growing areas which *B. napus* plants comprise non-transgenic mutations of its endogenous acetolactate synthase (ALS) genes, wherein the ALS I gene encodes an ALS I polypeptide containing an amino acid different from alanine at a position 190 of said first ALS I polypeptide and wherein the ALS III gene encodes an ALS III polypeptide containing an amino acid different from tryptophan at a position 559 of said ALS III polypeptide and thereby providing tolerance against the ALS inhibitor herbicide(s) according to this invention belonging to group (B) is imazamox [CAS RN 114311-32-9] (=B1-2).

Another ALS inhibitor herbicide which is preferably used for control of unwanted vegetation in *B. napus* growing areas which *B. napus* plants comprise non-transgenic mutations of its endogenous acetolactate synthase (ALS) genes, wherein the ALS I gene encodes an ALS I polypeptide containing an amino acid different from alanine at a position 190 of said first ALS I polypeptide and wherein the ALS III gene encodes an ALS III polypeptide containing an amino acid different from tryptophan at a position 559 of said ALS III polypeptide and thereby providing tolerance against the ALS inhibitor herbicide(s) according to this invention belonging to group (C) is bispyribac-sodium [CAS RN 125401-92-5] (=C1-1).

In another preferred embodiment, ALS inhibitor herbicides which are preferably used for control of unwanted vegetation in *B. napus* growing areas which *B. napus* plants are plants according to the invention are selected from the group consisting of Amidosulfuron, Bispyribac-sodium, Ethoxysulfuron, Flazasulfuron, Florasulam, Flupyrsulfuron-methyl, Foramsulfuron, Imazamox, Iodosulfuron-methy-sodium, Mesosulfuron-methyl, Metosulam, Metsulfuron-methyl, Nicosulfuron, Propoxycarbazone, Rimsulfuron, Sulfosulfuron, Thiencarbazone-methyl, Thifensulfuron-Methyl, more preferably Amidosulfuron, Ethoxysulfuron, Florasulam, Foramsulfuron, Imazamox, Iodosulfuron-methy-sodium, Mesosulfuron-methyl, Metosulam, Metsulfuron-methyl, Nicosulfuron, Rimsulfuron, Sulfosulfuron, Thifensulfuron-Methyl or Amidosulfuron, Ethoxysulfuron, Florasulam, Foramsulfuron, Iodosulfuron-methy-sodium, Mesosulfuron-methyl, Metosulam, Metsulfuron-methyl, Nicosulfuron, Rimsulfuron, Sulfosulfuron, Thifensulfuron-Methyl.

It is to be further understood that concerning all above defined ALS inhibitor herbicides and where not already specified by the respective CAS RN, all use forms, such as acids, and salts can be applied according to the invention.

Additionally, the ALS inhibitor herbicide(s) to be used according to the invention may comprise further components, for example agrochemically active compounds of a different type of mode of action and/or the formulation auxiliaries and/or additives customary in crop protection, or may be used together with these.

In a preferred embodiment, the herbicide combinations to be used according to the invention comprise effective amounts of the ALS inhibitor herbicide(s) belonging to groups (A), (B) and/or (C) and/or have synergistic actions. The synergistic actions can be observed, for example, when applying one or more ALS inhibitor herbicide(s) belonging to groups (A), (B), and/or (C) together, for example as a coformulation or as a tank mix; however, they can also be observed when the active compounds are applied at different times (splitting). It is also possible to apply the herbicides or the herbicide combinations in a plurality of portions (sequential application), for example pre-emergence applications followed by post-emergence applications or early post-emergence applications followed by medium or late post-emergence applications. Preference is given here to the joint or almost simultaneous application of the ALS-inhibitor herbicides belonging to groups (A), (B) and/or (C) of the combination in question.

The synergistic effects permit a reduction of the application rates of the individual ALS inhibitor herbicides, a higher efficacy at the same application rate, the control of species which were as yet uncontrolled (gaps), control of species which are tolerant or resistant to individual ALS inhibitor herbicides or to a number of ALS inhibitor herbicides, an extension of the period of application and/or a reduction in the number of individual applications required and—as a result for the user—weed control systems which are more advantageous economically and ecologically.

The herbicides to be used according to this invention are all acetolactate synthase (ALS) inhibitor herbicides and thus inhibit protein biosynthesis in plants.

The application rate of the ALS inhibitor herbicides belonging to groups (A), (B) or (C) (as defined above) can vary within a wide range, for example between 0.001 g and 1500 g of ai/ha (ai/ha means here and below "active substance per hectare"=based on 100% pure active compound). Applied at application rates of from 0.001 g to 1500 g of ai/ha, the herbicides belonging to classes A, B and C according to this invention, preferably the compounds A1-1; A1-4; A1-9; A1-12; A1-13; A1-16; A1-17; A1-18; A1-20; A1-26; A1-28; A1-29; A1-31; A1-41; A1-87; A2-2; A3-3; A3-5; A3-7, control, when used by the pre- and post-emergence method, a relatively wide spectrum of harmful plants, for example of annual and perennial mono- or dicotyledonous weeds, and also of unwanted crop plants (together also defined as "unwanted vegetation).

In many applications according to the invention, the application rates are generally lower, for example in the range of from 0.001 g to 1000 g of ai/ha, preferably from 0.1 g to 500 g of ai/ha, particularly preferably from 0.5 g to 250 g of ai/ha, and even more preferably 1.0 g to 200 g of ai/ha. In cases where the application of several ALS inhibitor herbicides is conducted, the quantity represents the total quantity of all of the applied ALS inhibitor herbicides.

For example, the combinations according to the invention of ALS inhibitor herbicides (belonging to groups (A), (B) and/or (C)) allow the activity to be enhanced synergistically in a manner which, by far and in an unexpected manner, exceeds the activities which can be achieved using the individual ALS inhibitor herbicides (belonging to groups (A), (B) and/or (C)).

For combinations of ALS inhibitor herbicides, the preferred conditions are illustrated below.

Of particular interest according to present invention is the use of herbicidal compositions for control of unwanted vegetation in *B. napus* plants, preferably in mutated *B. napus* plants as described herein having a content of the following ALS inhibitor herbicides:

(A1-1)+(A1-9); (A1-1)+(A1-12); (A1-1)+(A1-13); (A1-1)+(A1-16); (A1-1)+(A1-17); (A1-1)+(A1-18); (A1-1)+(A1-20); (A1-1)+(A1-26); (A1-1)+(A1-28); (A1-1)+(A1-29); (A1-1)+(A1-31); (A1-1)+(A1-41); (A1-1)+(A1-87); (A1-1)+(A2-2); (A1-1)+(A2-3); (A1-1)+(A3-3); (A1-1)+(A3-5); (A1-1)+(A3-7); (A1-1)+(B1-2); (A1-1)+(C1-1);

(A1-9)+(A1-12); (A1-9)+(A1-13); (A1-9)+(A1-16); (A1-9)+(A1-17); (A1-9)+(A1-18); (A1-9)+(A1-20); (A1-9)+(A1-26); (A1-9)+(A1-28); (A1-9)+(A1-29); (A1-9)+(A1-31); (A1-9)+(A1-41); (A1-9)+(A1-87); (A1-9)+(A2-2); (A1-9)+(A2-3); (A1-9)+(A3-3); (A1-9)+(A3-5); (A1-9)+(A3-7); (A1-9)+(B1-2); (A1-9)+(C1-1);

(A1-12)+(A1-13); (A1-12)+(A1-16); (A1-12)+(A1-17); (A1-12)+(A1-18); (A1-12)+(A1-20); (A1-12)+(A1-26); (A1-12)+(A1-28); (A1-12)+(A1-29); (A1-12)+(A1-31); (A1-12)+(A1-41); (A1-12)+(A1-87); (A1-12)+(A2-2); (A1-12)+(A2-3); (A1-12)+(A3-3); (A1-12)+(A3-5); (A1-12)+(A3-7); (A1-12)+(B1-2); (A1-12)+(C1-1);

(A1-13)+(A1-16); (A1-13)+(A1-17); (A1-13)+(A1-18); (A1-13)+(A1-20); (A1-13)+(A1-26); (A1-13)+(A1-28); (A1-13)+(A1-29); (A1-13)+(A1-31); (A1-13)+(A1-41); (A1-13)+(A1-87); (A1-13)+(A2-2); (A1-13)+(A2-3); (A1-13)+(A3-3); (A1-13)+(A3-5); (A1-13)+(A3-7); (A1-13)+(B1-2); (A1-13)+(C1-1);

(A1-16)+(A1-17); (A1-16)+(A1-18); (A1-16)+(A1-20); (A1-16)+(A1-26); (A1-16)+(A1-28); (A1-16)+(A1-29); (A1-16)+(A1-31); (A1-16)+(A1-41); (A1-16)+(A1-87); (A1-16)+(A2-2); (A1-16)+(A2-3); (A1-16)+(A3-3); (A1-16)+(A3-5); (A1-16)+(A3-7); (A1-16)+(B1-2); (A1-16)+(C1-1);

(A1-17)+(A1-18); (A1-17)+(A1-20); (A1-17)+(A1-26); (A1-17)+(A1-28); (A1-17)+(A1-29); (A1-17)+(A1-31); (A1-17)+(A1-41); (A1-17)+(A1-87); (A1-17)+(A2-2); (A1-17)+(A2-3); (A1-17)+(A3-3); (A1-17)+(A3-5); (A1-17)+(A3-7); (A1-17)+(B1-2); (A1-17)+(C1-1);

(A1-18)+(A1-20); (A1-18)+(A1-26); (A1-18)+(A1-28); (A1-18)+(A1-29); (A1-18)+(A1-31); (A1-18)+(A1-41); (A1-18)+(A1-87); (A1-18)+(A2-2); (A1-18)+(A2-3); (A1-18)+(A3-3); (A1-18)+(A3-5); (A1-18)+(A3-7); (A1-18)+(B1-2); (A1-18)+(C1-1);

(A1-20)+(A1-26); (A1-20)+(A1-28); (A1-20)+(A1-29); (A1-20)+(A1-31); (A1-20)+(A1-41); (A1-20)+(A1-87); (A1-20)+(A2-2); (A1-20)+(A2-3); (A1-20)+(A3-3); (A1-20)+(A3-5); (A1-20)+(A3-7); (A1-20)+(B1-2); (A1-20)+(C1-1);

(A1-26)+(A1-28); (A1-26)+(A1-29); (A1-26)+(A1-31); (A1-26)+(A1-41); (A1-26)+(A1-87); (A1-26)+(A2-2); (A1-26)+(A2-3); (A1-26)+(A3-3); (A1-26)+(A3-5); (A1-26)+(A3-7); (A1-26)+(B1-2); (A1-26)+(C1-1);

(A1-28)+(A1-29); (A1-28)+(A1-31); (A1-28)+(A1-41); (A1-28)+(A1-87); (A1-28)+(A2-2); (A1-28)+(A2-3); (A1-28)+(A3-3); (A1-28)+(A3-5); (A1-28)+(A3-7); (A1-28)+(B1-2); (A1-28)+(C1-1);

(A1-29)+(A1-31); (A1-29)+(A1-41); (A1-29)+(A1-87); (A1-29)+(A2-2); (A1-29)+(A2-3); (A1-29)+(A3-3); (A1-29)+(A3-5); (A1-29)+(A3-7); (A1-29)+(B1-2); (A1-29)+(C1-1);

(A1-31)+(A1-41); (A1-31)+(A1-87); (A1-31)+(A2-2); (A1-31)+(A2-3); (A1-31)+(A3-3); (A1-31)+(A3-5); (A1-31)+(A3-7); (A1-31)+(B1-2); (A1-31)+(C1-1);

(A1-41)+(A1-87); (A1-41)+(A2-2); (A1-41)+(A2-3); (A1-41)+(A3-3); (A1-41)+(A3-5); (A1-41)+(A3-7); (A1-41)+(B1-2); (A1-41)+(C1-1);

(A1-87)+(A2-2); (A1-87)+(A2-3); (A1-87)+(A3-3); (A1-87)+(A3-5); (A1-87)+(A3-7); (A1-87)+(B1-2); (A1-87)+(C1-1);

(A2-2)+(A2-3); (A2-2)+(A3-3); (A2-2)+(A3-5); (A2-2)+(A3-7); (A2-2)+(B1-2); (A2-2)+(C1-1);

(A2-3)+(A3-3); (A2-3)+(A3-5); (A2-3)+(A3-7); (A2-3)+(B1-2); (A2-3)+(C1-1);

(A3-3)+(A3-5); (A3-3)+(A3-7); (A3-3)+(B1-2); (A3-3)+(C1-1);

(A3-5)+(A3-7); (A3-5)+(B1-2); (A3-5)+(C1-1);

(A3-7)+(B1-2); (A3-7)+(C1-1);

(B1-2)+(C1-1).

Additionally, the ALS inhibitor herbicides to be used according to the invention may comprise further components, for example agrochemically active compounds of a different type of mode of action and/or the formulation auxiliaries and/or additives customary in crop protection, or may be used together with these.

The ALS inhibitor herbicide(s) to be used according to the invention or combinations of various such ALS inhibitor herbicides may furthermore comprise various agrochemically active compounds, for example from the group of the safeners, fungicides, insecticides, or from the group of the formulation auxiliaries and additives customary in crop protection.

In a further embodiment, the invention relates to the use of effective amounts of ALS inhibitor herbicide(s) (i.e. members of the groups (A), (B) and/or (C)) and non-ALS inhibitor herbicides (i.e. herbicides showing a mode of action that is different to the inhibition of the ALS enzyme [acetohydroxy-acid synthase; EC 2.2.1.6] (group D herbicides) in order obtain synergistic effect for the control of unwanted vegetation. Such synergistic actions can be observed, for example, when applying one or more ALS inhibitor herbicides (i.e. members of the groups (A), (B), and/or (C)) and one or more non ALS inhibitor herbicides (group D herbicides) together, for example as a coformulation or as a tank mix; however, they can also be observed when the active compounds are applied at different times (splitting). It is also possible to apply the ALS inhibitor herbicides and non ALS inhibitor herbicides in a plurality of portions (sequential application), for example pre-emergence applications followed by post-emergence applications or early post-emergence applications followed by medium or late post-emergence applications. Preference is given here to the joint or almost simultaneous application of the herbicides ((A), (B) and/or (C)) and (D) of the combination in question.

Suitable partner herbicides to be applied together with ALS inhibitor herbicideds are, for example, the following herbicides which differ structurally from the herbicides belonging to the groups (A), (B), and (C) as defined above, preferably herbicidally active compounds whose action is based on inhibition of, for example, acetyl coenzyme A carboxylase, PS I, PS II, HPPDO, phytoene desaturase, protoporphyrinogen oxidase, glutamine synthetase, cellulose biosynthesis, 5-enolpyruvylshikimate 3-phosphate synthetase, as described, for example, in Weed Research 26, 441-445 (1986), or "The Pesticide Manual", 14th edition, The British Crop Protection Council, 2007, or $15^{th}$ edition 2010, or in the corresponding "e-Pesticide Manual", Version 5 (2010), in each case published by the British Crop Protection Council, (hereinbelow in short also "PM"), and in the literature cited therein. Lists of common names are also available in "The Compendium of Pesticide Common Names" on the internet. Herbicides known from the literature (in brackets behind the common name hereinafter also classified by the indicators D1 to D426), which can be combined with ALS-inhibitor herbicides of groups (A), (B) and/or (C) and to be used according to present invention are, for example, the active compounds listed below: (note: the herbicides are referred to either by the "common name" in accordance with the International Organization for Standardization (ISO) or by the chemical name, together where appropriate with a customary code number, and in each case include all use forms, such as acids, salts, esters and isomers, such as stereoisomers and optical isomers, in particular the commercial form or the commercial forms, unless the context indicates otherwise. The citation given is of one use form and in some cases of two or more use forms):

acetochlor (=D1), acibenzolar (=D2), acibenzolar-S-methyl (=D3), acifluorfen (=D4), acifluorfen-sodium (=D5), aclonifen (=D6), alachlor (=D7), allidochlor (=D8), alloxydim (=D9), alloxydim-sodium (=D10), ametryn (=D11), amicarbazone (=D12), amidochlor (=D13), aminocyclopyrachlor (=D14), aminopyralid (=D15), amitrole (=D16), ammonium sulfamate (=D17), ancymidol (=D18), anilofos (=D19), asulam (=D20), atrazine (=D21), azafenidin (=D22), aziprotryn (=D23), beflubutamid (=D24), benazolin (=D25), benazolin-ethyl (=D26), bencarbazone (=D27), benfluralin (=D28), benfuresate (=D29), bensulide (=D30), bentazone (=D31), benzfendizone (=D32), benzobicyclon (=D33), benzofenap (=D34), benzofluor (=D35), benzoylprop (=D36), bicyclopyrone (=D37), bifenox (=D38), bilanafos (=D39), bilanafos-sodium (=D40), bromacil (=D41), bromobutide (=D42), bromofenoxim (=D43), bromoxynil (=D44), bromuron (=D45), buminafos (=D46), busoxinone (=D47), butachlor (=D48), butafenacil (=D49), butamifos (=D50), butenachlor (=D51), butralin (=D52), butroxydim (=D53), butylate (=D54), cafenstrole (=D55), carbetamide (=D56), carfentrazone (=D57), carfentrazone-ethyl (=D58), chlomethoxyfen (=D59), chloramben (=D60), chlorazifop (=D61), chlorazifop-butyl (=D62), chlorbromuron (=D63), chlorbufam (=D64), chlorfenac (=D65), chlorfenac-sodium (=D66), chlorfenprop (=D67), chlorflurenol (=D68), chlorflurenol-methyl (=D69), chloridazon (=D70), chlormequat-chloride (=D71), chlornitrofen (=D72), chlorophthalim (=D73), chlorthal-dimethyl (=D74), chlorotoluron (=D75), cinidon (=D76), cinidon-ethyl (=D77), cinmethylin (=D78), clethodim (=D79), clodinafop (=D80), clodinafop-propargyl (=D81), clofencet (=D82), clomazone (=D83), clomeprop (=D84), cloprop (=D85), clopyralid (=D86), cloransulam (=D87), cloransulam-methyl (=D88), cumyluron (=D89), cyanamide (=D90), cyanazine (=D91), cyclanilide (=D92), cycloate (=D93), cycloxydim (=D94), cycluron (=D95), cyhalofop (=D96), cyhalofop-butyl (=D97), cyperquat (=D98), cyprazine (=D99), cyprazole (=D100), 2,4-D (=D101), 2,4-DB (=D102), daimuron/dymron (=D103), dalapon (=D104), daminozide (=D105), dazomet (=D106), n-decanol (=D-107), desmedipham (=D108), desmetryn (=D109), detosyl-pyrazolate (=D110), diallate (=D111), dicamba (=D112), dichlobenil (=D113), dichlorprop (=D114), dichlorprop-P (=D115), diclofop (=D116), diclofop-methyl (=D117), diclofop-P-methyl (=D118), diethatyl (=D119), diethatyl-ethyl (=D120), difenoxuron (=D121), difenzoquat (=D122), diflufenican (=D123), diflufenzopyr (=D124), diflufenzopyr-sodium (=D125), dimefuron (=D126), dikegulac-sodium (=D127), dimefuron (=D128), dimepiperate (=D129), dimethachlor (=D130), dimethametryn (=D131), dimethenamid (=D132), dimethenamid-P (=D133), dimethipin (=D134), dimetrasulfuron (=D135), dinitramine (=D136), dinoseb (=D137), dinoterb (=D138), diphenamid (=D139), dipropetryn (=D140), diquat (=D141), diquat-dibromide (=D142), dithiopyr (=D143), diuron (=D144), DNOC (=D145), eglinazine-ethyl (=D146), endothal (=D147), EPTC (=D148), esprocarb (=D149), ethalfluralin (=D150), ethephon (=D151), ethidimuron (=D152), ethiozin (=D153), ethofumesate (=D154), ethoxyfen (=D155), ethoxyfen-ethyl (=D156), etobenzanid (=D157), F-5331 (=2-Chlor-4-fluor-5-[4-(3-fluorpropyl)-4,5-dihydro-5-oxo-1H-tetrazol-1-yl]-phenyl]-ethansulfonamid) (=D158), F-7967 (=3-[7-Chlor-5-fluor-2-(trifluormethyl)-1H-benzimidazol-4-yl]-1-methyl-6-(trifluormethyl)pyrimidin-2,4(1H,3H)-dion) (=D159), fenoprop (=D160), fenoxaprop (=D161), fenoxaprop-P (=D162), fenoxaprop-ethyl (=D163), fenoxaprop-P-ethyl (=D164), fenoxasulfone (=D165), fentrazamide (=D166), fenuron (=D167), flamprop (=D168), flamprop-M-isopropyl (=D169), flamprop-M-methyl (=D170), fluazifop (=D171), fluazifop-P (=D172), fluazifop-butyl (=D173), fluazifop-P-butyl (=D174), fluazolate (=D175), fluchloralin (=D176), flufenacet (thiafluamide) (=D177), flufenpyr (=D178), flufenpyr-ethyl (=D179), flumetralin (=D180), flumiclorac (=D181), flumiclorac-pentyl (=D182), flumioxazin (=D183), flumipropyn (=D184), fluometuron (=D185), fluorodifen (=D186), fluoroglycofen (=D187), fluoroglycofen-ethyl (=D188), flupoxam (=D189), flupropacil (=D190), flupropanate (=D191), flurenol (=D192), flurenol-butyl (=D193), fluridone (=D194), flurochloridone (=D195), fluroxypyr (=D196), fluroxypyr-meptyl (=D197), flurprimidol (=D198), flurtamone (=D199), fluthiacet (=D200), fluthiacet-methyl (=D201), fluthiamide (=D202), fomesafen (=203), forchlorfenuron (=D204), fosamine (=D205), furyloxyfen (=D206), gibberellic acid (=D207), glufosinate (=D208), glufosinate-ammonium (=D209), glufosinate-P (=D210), glufosinate-P-ammonium (=D211), glufosinate-P-sodium (=D212), glyphosate (=D213), glyphosate-isopropylammonium (=D214), H-9201 (=O-(2,4-Dimethyl-6-nitrophenyl)-O-ethyl-isopropylphosphoramidothioat) (=D215), halosafen (=D216), haloxyfop (=D217), haloxyfop-P (=D218), haloxyfop-ethoxyethyl (=D219), haloxyfop-P-ethoxyethyl (=D220), haloxyfop-methyl (=D221), haloxyfop-P-methyl (=D222), hexazinone (=D223), HW-02 (=1-(Dimethoxyphosphoryl)-ethyl(2,4-dichlorphenoxy) acetate) (=D224), inabenfide (=D225), indanofan (=D226), indaziflam (=D227), indol-3-acetic acid (IAA) (=D228), 4-indol-3-ylbutyric acid (IBA) (=D229), ioxynil (=D230), ipfencarbazone (=D231), isocarbamid (=D232), isopropalin (=D233), isoproturon (=D234), isouron (=D235), isoxaben (=D236), isoxachlortole (=D237), isoxaflutole (=D238), isoxapyrifop (=D239), KUH-043 (=3-({ [5-(Difluormethyl)-1-methyl-3-(trifluormethyl)-1H-pyrazol-4-yl]methyl}sulfonyl)-5,5-dimethyl-4,5-dihydro-1,2-oxazol) (=D240), karbutilate (=D241), ketospiradox (=D242), lactofen (=D243), lenacil (=D244), linuron (=D245), male is hydrazide (=D246), MCPA (=D247), MCPB (=D248), MCPB-methyl, -ethyl and -sodium (=D249), mecoprop (=D250), mecoprop-sodium (=D251), mecoprop-butotyl (=D252), mecoprop-P-butotyl (=D253), mecoprop-P-dimethylammonium (=D254), mecoprop-P-2-ethylhexyl (=D255), mecoprop-P-potassium (=D256), mefenacet (=D257), mefluidide (=D258), mepiquat-chloride (=D259), mesotrione (=D260), methabenzthiazuron (=D261), metam (=D262), metamifop (=D263), metamitron (=D264), metazachlor (=D265), metazole (=D266), methiopyrsulfuron (=D267), methiozolin (=D268), methoxyphenone (=D269), methyldymron (=D270), 1-methylcyclopropen (=D271), methylisothiocyanat (=D272), metobenzuron (=D273), metobromuron (=D274), metolachlor (=D275), S-metolachlor (=D-276), metoxuron (=D277), metribuzin (=D278), molinate (=D279), monalide (=D280), monocarbamide (=D281), monocarbamide-dihydrogensulfate (=D282), monolinuron (=D283), monosulfuron-ester (=D284), monuron (=D285), MT-128 (=6-Chlor-N-[(2E)-3-chlorprop-2-en-1-yl]-5-methyl-N-phenylpyridazin-3-amine) (=D286), MT-5950 (=N-[3-Chlor-4-(1-methylethyl)-phenyl]-2-methylpentanamide) (=D287), NGGC-011 (=D288), naproanilide (=D289), napropamide (=D290), naptalam (=D291), NC-310 (=4-(2,4-Dichlorobenzoyl)-1-methyl-5-benzyloxypyrazole) (=D292), neburon (=D293), nipyraclofen (=D294), nitralin (=D295), nitrofen (=D296), nitrophenolat-sodium (isomer mixture) (=D297), nitrofluorfen (=D298), nonanoic acid (=D299), norflurazon (=D300), orbencarb (=D301), oryzalin (=D302), oxadiargyl (=D303), oxadiazon (=D304), oxaziclomefone (=D305), oxyfluorfen (=D306), paclobutrazol (=D307), paraquat (=D308), paraquat-dichloride (=D309), pelargonic acid (nonanoic acid) (=D310), pendimethalin (=D311), pendralin (=D312), pentanochlor (=D313), pentoxazone (=D314), perfluidone (=D315), pethoxamid (=D317), phenisopham (=D318), phenmedipham (=D319), phenmedipham-ethyl (=D320), picloram (=D321), picolinafen (=D322), pinoxaden (=D323), piperophos (=D324), pirifenop (=D325), pirifenop-butyl (=D326), pretilachlor (=D327), probenazole (=D328), profluazol (=D329), procyazine (=D330), prodiamine (=D331), prifluraline (=D332), profoxydim (=D333), prohexadione (=D334), prohexadione-calcium (=D335), prohydrojasmone (=D336), prometon (=D337), prometryn (=D338), propachlor (=D339), propanil (=D340), propaquizafop (=D341), propazine (=D342), propham (=D343), propisochlor (=D344), propyzamide (=D345), prosulfalin (=D346), prosulfocarb (=D347), prynachlor (=D348), pyraclonil (=D349), pyraflufen (=D350), pyraflufen-ethyl (=D351), pyrasulfotole (=D352), pyrazolynate (pyrazolate) (=D353), pyrazoxyfen (=D354), pyribambenz (=D355), pyributicarb (=D356), pyridafol (=D357), pyridate (=D358), pyriminobac (=D359), pyrimisulfan (=D360), pyroxasulfone (=D361), quinclorac (=D362), quinmerac (=D363), quinoclamine (=D364), quizalofop (=D365), quizalofop-ethyl (=D366), quizalofop-P (=D367), quizalofop-P-ethyl (=D368), quizalofop-P-tefuryl (=D369), saflufenacil (=D370), secbumeton (=D371), sethoxydim (=D372), siduron (=D373), simazine (=D374), simetryn (=D375), SN-106279 (=Methyl-(2R)-2-({7-[2-chlor-4-(trifluormethyl)phenoxy]-2-naphthyl}oxy)-propanoate) (=D376), sulcotrione (=D377), sulfallate (CDEC) (=D378), sulfentrazone (=D379), sulfosate (glyphosate-trimesium) (=D380), SYN-523 (=D381), SYP-249 (=1-Ethoxy-3-methyl-1-oxobut-3-en-2-yl-5-[2-chlor-4-(trifluormethyl)phenoxy]-2-nitrobenzoate) (=D382), tebutam (=D383), tebuthiuron (=D384), tecnazene (=D385), tefuryltrione (=D386), tembotrione (=D387), tepraloxydim (=D388), terbacil (=D389), terbucarb (=D390), terbuchlor (=D391), terbumeton (=D392), terbuthylazine (=D393), terbutryn (=D394), thenylchlor (=D395), thiafluamide (=D396), thiazafluron (=D397), thiazopyr (=D398), thidiazimin (=D399), thidiazuron (=D400), thiobencarb (=D401), tiocarbazil (=D402), topramezone (=D403), tralkoxydim (=D404), triallate (=D405), triaziflam (=D406), triazofenamide (=D407), trichloracetic acid (TCA) (=D408), triclopyr (=D409), tridiphane (=D410), trietazine (=D411), trifluralin (=D412), trimeturon (=D413), trinexapac (=D414), trinexapac-ethyl (=D415), tsitodef (=D416), uniconazole (=D417), uniconazole-P (=D418), vernolate (=D419), ZJ-0862 (=3,4-Dichlor-N-{2-[(4,6-dimethoxypyrimidin-2-yl)oxy]benzyl}aniline) (=D420), the below compounds defined by their chemical structure, respectively:

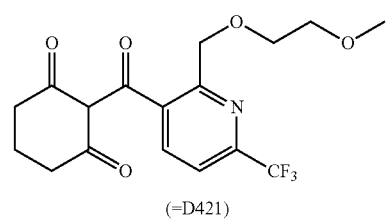

(=D421)

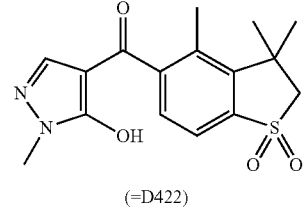

(=D422)

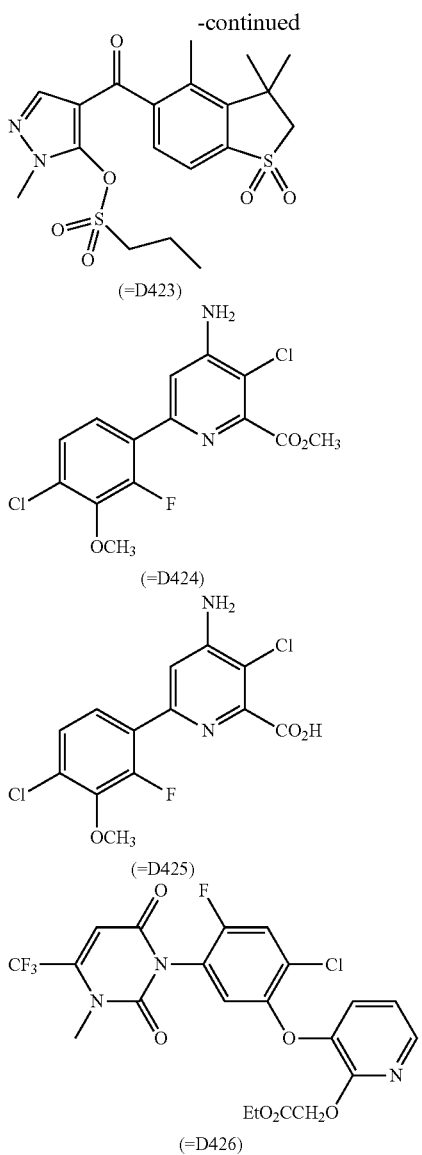

and propachlor (D 427).

Preferably, further herbicides which differ structurally and via their mode of action from the ALS inhibitor herbicides belonging to the groups (A), (B), and (C) as defined above and to be applied according to the present invention for control of unwanted vegetation in ALS inhibitor herbicide tolerant *B. napus* plants, preferably in mutated *B. napus* plants as described herein. In connection with ALS inhibitor herbicides belonging to the groups (A), (B), and (C) are those selected from the group consisting of acetochlor (=D1), carbetamide (=D56), fenoxaprop-P-ethyl (=D164), fluazifop-P-butyl (=D174), haloxyfop-P-methyl (=D222), metolachlor (=D275), dimethenamid (=D132), napropamide (=D290), pethoxamid (=D317), propaquizafop (=D341), propisochlor (=D344), propyzamide (=D345), quinmerac (=D363), propachlor (D 427), clomazone (=D83), clopyralid (=D86), dimethachlor (=D130), metazachlor (=D265), picloram (=D321), and quizalofop-P-ethyl (=D368).

Even more preferably, further herbicides which differ from the ALS inhibitor herbicides belonging to the groups (A), (B), and (C) as defined above and to be applied according to the invention in connection with ALS inhibitor herbicides belonging to the groups (A), (B), and (C) are those selected from the group consisting of clomazone (=D83), clopyralid (=D86), dimethachlor (=D130), metazachlor (=D265), picloram (=D321), and quizalofop-P-ethyl (=D368).

Mixtures containing ALS inhibitor herbicides and non ALS inhibitor herbicides, compositions comprising mixtures of one or more ALS inhibitor herbicide(s) (compounds belonging to one or more of groups (A), (B) and (C)) and non ALS inhibitor heribicide(s) (group (D) members; as defined above) that are of very particular interest in order to be used according to present invention for control of unwanted vegetation are:

(A1-1)+(D83); (A1-1)+(D86); (A1-1)+(D130); (A1-1)+(D265); (A1-1)+(D321); (A1-1)+(D368);
(A1-9)+(D83); (A1-1)+(D86); (A1-1)+(D130); (A1-1)+(D265); (A1-1)+(D321); (A1-1)+(D368);
(A1-12)+(D83); (A1-1)+(D86); (A1-1)+(D130); (A1-1)+(D265); (A1-1)+(D321); (A1-1)+(D368);
(A1-13)+(D83); (A1-1)+(D86); (A1-1)+(D130); (A1-1)+(D265); (A1-1)+(D321); (A1-1)+(D368);
(A1-16)+(D83); (A1-1)+(D86); (A1-1)+(D130); (A1-1)+(D265); (A1-1)+(D321); (A1-1)+(D368);
(A1-17)+(D83); (A1-1)+(D86); (A1-1)+(D130); (A1-1)+(D265); (A1-1)+(D321); (A1-1)+(D368);
(A1-18)+(D83); (A1-1)+(D86); (A1-1)+(D130); (A1-1)+(D265); (A1-1)+(D321); (A1-1)+(D368);
(A1-20)+(D83); (A1-1)+(D86); (A1-1)+(D130); (A1-1)+(D265); (A1-1)+(D321); (A1-1)+(D368);
(A1-26)+(D83); (A1-1)+(D86); (A1-1)+(D130); (A1-1)+(D265); (A1-1)+(D321); (A1-1)+(D368);
(A1-28)+(D83); (A1-1)+(D86); (A1-1)+(D130); (A1-1)+(D265); (A1-1)+(D321); (A1-1)+(D368);
(A1-29)+(D83); (A1-1)+(D86); (A1-1)+(D130); (A1-1)+(D265); (A1-1)+(D321); (A1-1)+(D368);
(A1-31)+(D83); (A1-1)+(D86); (A1-1)+(D130); (A1-1)+(D265); (A1-1)+(D321); (A1-1)+(D368);
(A1-41)+(D83); (A1-1)+(D86); (A1-1)+(D130); (A1-1)+(D265); (A1-1)+(D321); (A1-1)+(D368);
(A1-87)+(D83); (A1-1)+(D86); (A1-1)+(D130); (A1-1)+(D265); (A1-1)+(D321); (A1-1)+(D368);
(A2-2)+(D83); (A1-1)+(D86); (A1-1)+(D130); (A1-1)+(D265); (A1-1)+(D321); (A1-1)+(D368);
(A2-3)+(D83); (A1-1)+(D86); (A1-1)+(D130); (A1-1)+(D265); (A1-1)+(D321); (A1-1)+(D368);
(A3-3)+(D83); (A1-1)+(D86); (A1-1)+(D130); (A1-1)+(D265); (A1-1)+(D321); (A1-1)+(D368);
(A3-5)+(D83); (A1-1)+(D86); (A1-1)+(D130); (A1-1)+(D265); (A1-1)+(D321); (A1-1)+(D368);
(A3-7)+(D83); (A1-1)+(D86); (A1-1)+(D130); (A1-1)+(D265); (A1-1)+(D321); (A1-1)+(D368);
(A4-1)+(D83); (A4-1)+(D86); (A4-1)+(D130); (A4-1)+(D265); (A4-1)+(D321); (A4-1)+(D368);
(A4-2)+(D83); (A4-2)+(D86); (A4-2)+(D130); (A4-2)+(D265); (A4-2)+(D321); (A4-2)+(D368);
(A4-3)+(D83); (A4-3)+(D86); (A4-3)+(D130); (A4-3)+(D265); (A4-3)+(D321); (A4-3)+(D368);
(A4-2)+(D83); (A4-2)+(D86); (A4-2)+(D130); (A4-2)+(D265); (A4-2)+(D321); (A4-2)+(D368);
(B1-2)+(D83); (B1-2)+(D86); (B1-2)+(D130); (B1-2)+(D265); (B1-2)+(D321); (B1-2)+(D368);
(C1-1)+(D83); (C1-1)+(D86); (C1-1)+(D130); (C1-1)+(D265); (C1-1)+(D321); (C1-1)+(D368).

The application of ALS inhibitor herbicides also act efficiently on perennial weeds which produce shoots from rhizomes, root stocks and other perennial organs and which are difficult to control. Here, the substances can be applied, for example, by the pre-sowing method, the pre-emergence method or the post-emergence method, for example jointly or separately. Preference is given, for example, to application by the post-emergence method, in particular to the emerged harmful plants.

Specific examples may be mentioned of some representatives of the monocotyledonous and dicotyledonous weed flora which can be controlled by the ALS inhibitor herbicides, without the enumeration being restricted to certain species.

Examples of weed species on which the application according to present invention act efficiently are, from amongst the monocotyledonous weed species, *Avena* spp., *Alopecurus* spp., *Apera* spp., *Brachiaria* spp., *Bromus* spp., *Digitaria* spp., *Lolium* spp., *Echinochloa* spp., *Panicum* spp., *Phalaris* spp., *Poa* spp., *Setaria* spp., volunteer cereals (*Triticum* sp., *Hordeum* sp.) and also *Cyperus* species from the annual group, and, among the perennial species, *Agropyron*, *Cynodon*, *Imperata* and *Sorghum* and also perennial *Cyperus* species.

In the case of the dicotyledonous weed species, the spectrum of action extends to genera such as, for example, *Aethusa* spp., *Amaranthus* spp., *Capsella* spp, *Centaurea* spp., *Chenopodium* spp., *Chrysanthemum* spp., *Galium* spp., *Geranium* spp., *Lamium* spp., *Matricaria* spp., *Myosotis* spp., *Papaver* spp., *Polygonum* spp., *Sinapis* spp., *Solanum* spp., *Stellaria* spp., *Thlaspi* spp., *Urtica* spp., *Veronica* spp. and *Viola* spp., *Xanthium* spp., among the annuals, and *Convolvulus, Cirsium, Rumex* and *Artemisia* in the case of the perennial weeds.

In one embodiment, a *Brassica*, preferably *B. napus*, plant as described herein to which one or more ALS inhibitor herbicide(s) alone or in combination with one or more herbicide(s) that do(es) not belong to the class of ALS inhibitor herbicides are applied for control of unwanted vegetation in *Brassica*, preferably *B. napus*, plant comprising an altered ALS I *Brassica*, preferably *B. napus*, gene carrying a point mutation which leads to an amino acid in the polypeptide encoded by said ALS I gene, wherein said amino acid is at a position corresponding to a position selected from the group consisting of 205, 574, 653 and 654 of SEQ ID NO: 10 and wherein said amino acid is different from alanine at position 205, tryptophan at position 574, serine at position 653 and glycine at position 654 of SEQ ID NO: 10; and comprising an altered ALS III *Brassica*, preferably *B. napus*, gene carrying a point mutation which leads to an amino acid in the polypeptide encoded by said ALS III gene, wherein said amino acid is at a position corresponding to a position selected from the group consisting of 205, 574, 653 and 654 of SEQ ID NO: 10 and wherein said amino acid is different from alanine at position 205, tryptophan at position 574, serine at position 653 and glycine at position 654 of SEQ ID NO: 10.

In another embodiment, a *Brassica*, preferably *B. napus*, plant as described herein to which one or more ALS inhibitor herbicide(s) alone or in combination with one or more herbicide(s) that do(es) not belong to the class of ALS inhibitor herbicides are applied for control of unwanted vegetation in *Brassica*, preferably *B. napus*, plant comprising an ALS I polypeptide containing an amino acid different from alanine at a position of said ALS I a *Brassica*, preferably *B. napus*, polypeptide corresponding to position 205 of SEQ ID NO: 10 and an ALS III *Brassica*, preferably *B. napus*, polypeptide containing an amino acid different from tryptophan at a position of said ALS III polypeptide corresponding to position 574 of SEQ ID NO: 10.

In another embodiment, a *Brassica*, preferably *B. napus*, plant as described herein to which one or more ALS inhibitor herbicide(s) alone or in combination with one or more herbicide(s) that do(es) not belong to the class of ALS inhibitor herbicides are applied for control of unwanted vegetation in *Brassica*, preferably *B. napus*, plant comprising non-transgenic mutations of its endogenous acetolactate synthase (ALS) *Brassica*, preferably *B. napus*, genes, wherein the ALS I *Brassica*, preferably *B. napus*, gene encodes an ALS I *Brassica*, preferably *B. napus*, polypeptide containing an amino acid different from alanine at a position corresponding to position 205 of SEQ ID NO: 10 and wherein the ALS III *Brassica*, preferably *B. napus*, gene encodes an ALS III *Brassica*, preferably *B. napus*, polypeptide containing an amino acid different from tryptophan at a position corresponding to position 574 of SEQ ID NO: 10.

In yet another embodiment, a *Brassica*, such as *B. napus*, plant as described herein is homozygous regarding the mutation of an ALS I gene and an ALS II gene, respectively, as described herein.

As used herein, the term "heterozygous" means a genetic condition existing when two different alleles reside at a specific locus, but are positioned individually on corresponding pairs of homologous chromosomes in the cell. In other words, two different ALS I alleles and two different ALS III alleles, respectively, reside at specific loci but are positioned individually on corresponding pairs of homologous chromosomes in the cell.

Conversely, as used herein, the term "homozygous" means a genetic condition existing when two (all) identical alleles reside at a specific locus, but are positioned individually on corresponding pairs of homologous chromosomes in the cell.

As used herein, the term "locus" (loci plural) means a specific place or places or a site on a chromosome where, e.g., a gene or genetic marker is found.

Therefore, the present invention relates to the use of one or more ALS inhibitor herbicide(s) alone or in combination with one or more non ALS inhibitor herbicide(s) for weed control in *Brassica*, preferably *B. napus*, growing areas which *Brassica*, preferably *B. napus*, comprise an altered ALS I *Brassica*, preferably *B. napus*, protein having at least one amino acid different at a position corresponding to at least one position selected from the group consisting of A205, W574, S653 and G654 of SEQ ID NO: 10 (wherein the letters in front of the numbers refer to the one letter code of amino acids); and comprise an altered ALS III *Brassica*, preferably *B. napus*, protein having at least one amino acid different at a position corresponding to at least one position selected from the group consisting of A205, W574, S653 and G654 of SEQ ID NO: 10 (wherein the letters in front of the numbers refer to the one letter code of amino acids).

In one embodiment, the present invention relates to the use of one or more ALS inhibitor herbicide(s) alone or in combination with one or more non ALS inhibitor herbicide(s) for weed control in *B. napus* growing areas which *B. napus* comprise an endogenous ALS I gene, wherein the ALS I gene comprises a codon encoding an amino acid different from Ala, preferably Val, at a position corresponding to position 568-570 of the nucleotide sequence of the *B. napus* ALS I gene shown in SEQ ID NO: 1, and an endogenous ALS III gene, wherein the ALS III gene comprises a codon encoding an amino acid different from Trp, preferably Leu, at a position corresponding to position 1666-1668 of the nucleotide sequence of the *B. napus* ALS III gene shown in SEQ ID NO: 3, which plants are heterozygous or homozygous, preferably homozygous concerning the mutation in codon 568-570 of the endogenous ALS I gene and the mutation in codon 1666-1668 of the endogenous ALS III gene.

Owing to their herbicidal and plant growth-regulatory properties, ALS inhibitor herbicides belonging to one or more of the groups (A), (B), and (C) either alone or in combination with non ALS inhibitor herbicides can be employed for controlling harmful plants in known *Brassica*, preferably *B. napus*, plants but also in tolerant or genetically modified crop plants that do already exists or need still to be developed. In general, the transgenic plants are distinguished by specific advantageous properties, in addition to tolerances to the ALS inhibitor herbicides according to the invention, for example, by tolerances to non ALS inhibitor herbicides, resistances to plant diseases or the causative organisms of plant diseases such as certain insects or microorganisms, such as funghi, bacteria or viruses. Other specific characteristics relate, for example, to the harvested material with regard to quantity, quality, storability, composition and specific constituents. Thus, transgenic plants are known whose oil content is increased, or whose oil quality is altered, or those where the harvested material has a different fatty acid composition.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which exhibit tolerance to non ALS inhibitor herbicides, transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology are known in principle with the aid of which novel transgenic plants with modified properties can be generated; see, for example, Sambrook et al., 1989, Molecular Cloning, A Laboratory Manual, 2$^{nd}$ Edition, Cold Spring Harbor Laboratory Press, Cold Spring Harbor, N.Y.; or Winnacker "Gene and Klone", VCH Weinheim 2$^{nd}$ Edition 1996 or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, the abovementioned standard methods allow base exchanges to be carried out, subsequences to be removed, or natural or synthetic sequences to be added. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give rise to entire plants. Thus, transgenic *Brassica*, preferably *B. napus*, plants can be obtained whose properties are altered by overexpression, suppression or inhibition of homologous (=natural) genes or gene sequences or the expression of heterologous (=foreign) genes or gene sequences.

The present invention furthermore provides a method for controlling unwanted plants in *B. napus* plants as described herein which comprises applying one or more ALS inhibitor herbicides belonging to groups (A), (B) and/or (C) to the plants (for example harmful plants, such as monocotyledonous or dicotyledonous weeds or unwanted crop plants), the seed (seeds or vegetative propagation organs, such as tubers or shoot parts) or to the area in which the plants grow (for example the area under cultivation), for example together or separately.

The present invention furthermore provides a method for controlling unwanted plants in *B. napus* plants as described herein which comprises applying one or more ALS inhibitor herbicide(s) belonging to groups (A), (B) and/or (C) alone or in combination with non ALS inhibitor herbicides belonging to class (D) compound according to the invention to the plants (for example harmful plants, such as monocotyledonous or dicotyledonous weeds or unwanted crop plants), the seed (seeds or vegetative propagation organs, such as tubers or shoot parts) or to the area in which the plants grow (for example the area under cultivation), for example together or separately. One or more non ALS inhibitor herbicides may be applied in combination with one or more ALS inhibitor herbicide(s) before, after or simultaneously with the ALS inhibitor herbicide(s) to the plants, the seed or the area in which the plants grow (for example the area under cultivation).

"Unwanted plants" or "unwanted vegetation" are to be understood as meaning all plants which grow in locations where they are unwanted. This can, for example, be harmful plants (for example monocotyledonous or dicotyledonous species or other unwanted crop plants (volunteers)) such as *Geranium dissectum, Centaurea cyanus, Sinapis arvensis* and/or *Alopecurus myosuroides.*

In one embodiment, an unwanted plant is at least one dicotyledonous plant selected from the group consisting of *Aethusa cynapium, Agrostemma githago, Amaranthus* sp., *Ambrosia artemisifolia, Ammi majus, Anagallis arvensis, Anchusa officinalis, Anthemis* sp., *Aphanes arvensis, Arabidopsis thaliana, Artemisia vulgaris, Atriplex* sp., *Bidens* sp., *Bifora radians, Brassica nigra, Calendula arvensis, Capsella bursa pastoris, Cardamine hirsute, Cardaria draba, Centaurea cyanus, Cerastium arvense, Chaenorhinum minus, Chenopodium* sp., *Chrysanthemum segetum, Cirsium arvense, Convolvulus* sp., *Coronopus* sp., *Datura stramonium, Daucus carota, Descurainia sophia, Diplotaxis muralis, Echium vulgare, Erigeron Canadensis, Erodium circutarium, Erysium cheiranthoides, Euphorbia* sp., *Filaginella uliginosa, Fumaria officinalis, Galeopsis* sp., *Galeopsis tetraclit, Galinsoga parviflora, Galium aparine, Geranium* sp., *Juncus bufonius, Kickxia spuria, Lactuca sericola, Lamium* sp, *Lapsana*

*communis, Lathyrus tuberosus, Legousia speculum-veneris, Linaria vulgaris, Lithospermum arvense, Lycopsis arvensis, Malva* sp., *Matricaria* sp., *Menta arvensis, Mercurialis annua, Myagrum perfoliatum, Myosotis arvensis, Papaver* sp., *Picris echioides, Polygonum* sp., *Portulaca oleracea, Ranunculus* sp., *Raphanus raphanistrum, Rumex* sp., *Scandix pecten-veneris, Senecio vulgaris, Silene* sp., *Sinapis arvensis, Sisymbrium officinale, Solanum nigrum, Sonchus* sp., *Spergula arvensis, Stachys arvensis, Stellaria media, Thlaspi arvense, Tussilago farfara, Urtica urens, Verbena officinalis, Veronica* sp., *Vicia* sp., *Viola arvensis* and *Xanthium* sp. In another embodiment, an unwanted plant is at least one plant selected from the group consisting of *Aethusa cynapium, Galium aparine, Geranium* sp., *Lamium* sp, *Matricaria* sp., *Myosotis arvensis, Papaver* sp., *Polygonum* sp., *Sisymbrium officinale, Stellaria media, Thlaspi arvense, Urtica urens* and *Viola arvensis.*

In yet another embodiment, an unwanted plant is at least one monocotyledonous plant selected from the group consisting of *Agropyron repens, Alopecurus myosuroides, Apera spica-venti, Avena* sp., *Bromus* sp., *Cyperus* sp., *Digitaria* sp., *Echinochloa* sp., *Hordeum murinum, Lolium multiflorum, Panicum dichotomiflorum, Phalaris canariensis, Poa* sp., *Setaria* sp., *Sorghum halepense, Leptochloa filiformis.* In another embodiment, an unwanted plant is at least one plant selected from the group consisting of *Agropyron repens, Alopecurus myosuroides, Apera spica-venti, Avena* sp. and *Poa* sp.

In yet another embodiment, an unwanted plant is at least one monocotyledonous plant selected from the group consisting of *Beta vulgaris, Helianthus annuus, Solanum tuberosum, Triticum vulgare, Hordeum vulgare, Secale cereale, Avena sativa.* In another embodiment, an unwanted plant is *Triticum vulgare* and *Hordeum vulgare.*

The herbicide combinations to be used according to the invention can be prepared by known processes, for example as mixed formulations of the individual components, if appropriate with further active compounds, additives and/or customary formulation auxiliaries, which combinations are then applied in a customary manner diluted with water, or as tank mixes by joint dilution of the components, formulated separately or formulated partially separately, with water. Also possible is the split application of the separately formulated or partially separately formulated individual components.

It is also possible to apply ALS inhibitor herbicides or the combination comprising ALS inhibitor herbicide(s) and non ALS inhibitor herbicide(s) in a plurality of portions (sequential application) using, for example, pre-emergence applications followed by post-emergence applications or using early post-emergence applications followed by medium or late post-emergence applications. Preference is given here to the joint or almost simultaneous application of the active compounds of the combination in question.

The herbicides belonging to any of the above defined groups (A), (B), (C) and (D) and to be applied according to present invention can be converted jointly or separately into customary formulations, such as solutions, emulsions suspensions, powders, foams, pastes, granules, aerosols, natural and synthetic materials impregnated with active compound and microencapsulations in polymeric materials. The formulations may comprise the customary auxiliaries and additives.

These formulations are produced in a known manner, for example by mixing the active compounds with extenders, that is liquid solvents, pressurized liquefied gases and/or solid carriers, if appropriate with the use of surfactants, that is emulsifiers and/or dispersants, and/or foam formers.

If the extender used is water, it is also possible to use, for example, organic solvents as auxiliary solvents. Suitable liquid solvents are essentially: aromatics, such as xylene, toluene, alkylnaphthalenes, chlorinated aromatics or chlorinated aliphatic hydrocarbons, such as chlorobenzenes, chloroethylenes, or methylene chloride, aliphatic hydrocarbons, such as cyclohexane or paraffins, for example mineral oil fractions, mineral and vegetable oils, alcohols, such as butanol or glycol, and ethers and esters thereof, ketones, such as acetone, methyl ethyl ketone, methyl isobutyl ketone or cyclohexanone, strongly polar solvents, such as dimethylformamide or dimethyl sulfoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite and dolomite, and also synthetic granules of inorganic and organic meals, and granules of organic material, such as sawdust, coconut shells, corn cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins and synthetic phospholipids, can be used in the formulations. Other possible additives are mineral and vegetable oils.

The herbicidal action of the herbicide combinations to be used according to the invention can be improved, for example, by surfactants, preferably by wetting agents from the group of the fatty alcohol polyglycol ethers. The fatty alcohol polyglycol ethers preferably comprise 10-18 carbon atoms in the fatty alcohol radical and 2-20 ethylene oxide units in the polyglycol ether moiety. The fatty alcohol polyglycol ethers may be present in nonionic form, or ionic form, for example in the form of fatty alcohol polyglycol ether sulfates, which may be used, for example, as alkali metal salts (for example sodium salts and potassium salts) or ammonium salts, or even as alkaline earth metal salts, such as magnesium salts, such as $C_{12}/C_{14}$-fatty alcohol diglycol ether sulfate sodium (Genapol® LRO, Clariant GmbH); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, ($C_{10}$-$C_{18}$)-, preferably ($C_{10}$-$C_{14}$)-fatty alcohol polyglycol ethers (for example isotridecyl alcohol polyglycol ethers) which comprise, for example, 2-20, preferably 3-15, ethylene oxide units, for example those from the Genapol® X-series, such as Genapol® X-030, Genapol® X-060, Genapol® X-080 or Genapol® X-150 (all from Clariant GmbH).

The present invention further comprises the combination of ALS inhibitor herbicides belonging to any of the groups (A), (B), and (C) according to present invention with the wetting agents mentioned above from the group of the fatty alcohol polyglycol ethers which preferably contain 10-18 carbon atoms in the fatty alcohol radical and 2-20 ethylene oxide units in the polyglycol ether moiety and which may be present in nonionic or ionic form (for example as fatty alcohol polyglycol ether sulfates). Preference is given to $C_{12}/C_{14}$-fatty alcohol diglycol ether sulfate sodium (Genapol® LRO, Clariant GmbH) and isotridecyl alcohol polyglycol ether having 3-15 ethylene oxide units, for example from the Genapol® X-series, such as Genapol® X-030, Genapol® X-060, Genapol® X-080 and Genapol® X-150 (all from Clariant GmbH). Furthermore, it is known that fatty alcohol polyglycol ethers, such as nonionic or ionic fatty alcohol polyglycol ethers (for example fatty alcohol polyglycol ether sulfates) are also suitable for use as penetrants and activity enhancers for a number of other herbicides (see, for example, EP-A-0502014).

Furthermore, it is known that fatty alcohol polyglycol ethers, such as nonionic or ionic fatty alcohol polyglycol ethers (for example fatty alcohol polyglycol ether sulfates) are also suitable for use as penetrants and activity enhancers for a number of other herbicides (see, for example, EP-A-0502014).

The herbicidal action of the herbicide combinations according to the invention can also be enhanced by using vegetable oils. The term vegetable oils is to be understood as meaning oils of oleaginous plant species, such as soybean oil, rapeseed oil, corn oil, sunflower oil, cottonseed oil, linseed oil, coconut oil, palm oil, thistle oil or castor oil, in particular rapeseed oil, and also their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-, fatty acids. The $C_{10}$-$C_{22}$-fatty acid esters are, for example, esters of unsaturated or saturated $C_{10}$-$C_{22}$-fatty acids, in particular those having an even number of carbon atoms, for example erucic acid, lauric acid, palmitic acid and in particular $C_{18}$-fatty acids, such as stearic acid, oleic acid, linoleic acid or linolenic acid.

Examples of $C_{10}$-$C_{22}$-fatty acid esters are esters obtained by reacting glycerol or glycol with the $C_{10}$-$C_{22}$-fatty acids contained, for example, in oils of oleaginous plant species, or $C_1$-$C_{20}$-alkyl-$C_{10}$-$C_{22}$-fatty acid esters which can be obtained, for example, by transesterification of the aforementioned glycerol- or glycol-$C_{10}$-$C_{22}$-fatty acid esters with $C_1$-$C_{20}$-alcohols (for example methanol, ethanol, propanol or butanol). The transesterification can be carried out by known methods as described, for example, in Römpp Chemie Lexikon, 9th edition, Volume 2, page 1343, Thieme Verlag Stuttgart.

Preferred $C_1$-$C_{20}$-alkyl-$C_{10}$-$C_{22}$-fatty acid esters are methyl esters, ethyl esters, propyl esters, butyl esters, 2-ethylhexyl esters and dodecyl esters. Preferred glycol- and glycerol-$C_{10}$-$C_{22}$-fatty acid esters are the uniform or mixed glycol esters and glycerol esters of $C_{10}$-$C_{22}$-fatty acids, in particular fatty acids having an even number of carbon atoms, for example erucic acid, lauric acid, palmitic acid and, in particular, $C_{18}$-fatty acids, such as stearic acid, oleic acid, linoleic acid or linolenic acid.

In the herbicidal compositions to be used according to the invention, the vegetable oils can be present, for example, in the form of commercially available oil-containing formulation additives, in particular those based on rapeseed oil, such as Hasten® (Victorian Chemical Company, Australia, hereinbelow referred to as Hasten, main ingredient: rapeseed oil ethyl ester), Actirob®B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

In a further embodiment, herbicidal combinations to be used according to present invention can be formulated with the vegetable oils mentioned above, such as rapeseed oil, preferably in the form of commercially available oil-containing formulation additives, in particular those based on rapeseed oil, such as Hasten® (Victorian Chemical Company, Australia, hereinbelow referred to as Hasten, main ingredient: rapeseed oil ethyl ester), Actirob®B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

It is possible to use colorants, such as inorganic pigments, for example iron oxide, titanium oxide, Prussian Blue, and organic dyes, such as alizarin dyes, azo dyes and metal phthalocyanine dyes, and trace nutrients such as salts of iron, manganese, boron, copper, cobalt, molybdenum and zinc.

The formulations to be used according to present invention generally comprise from 0.1 to 95% by weight of active compounds, preferably from 0.5 to 90% by weight.

As such or in their formulations, the ALS inhibitor herbicides belonging to any of the above defined groups (A), (B), and (C) can also be used as a mixture with other agrochemically active compounds, such as known non ALS inhibitor herbicides, for controlling unwanted vegetation, for example for controlling weeds or for controlling unwanted crop plants, finished formulations or tank mixes, for example, being possible.

The use of a mixture of ALS inhibitor herbicides belonging to any of the above defined groups (A), (B), and (C) with other known active compounds, such as fungicides, insecticides, acaricides, nematicides, safeners, bird repellants, plant nutrients and soil structure improvers is likewise possible.

The ALS inhibitor herbicides belonging to any of the above defined groups (A), (B), (C) can be used as such, in the form of their formulations or in the use forms prepared therefrom by further dilution, such as ready-to-use solutions, suspensions, emulsions, powders, pastes and granules. Application is carried out in a customary manner, for example by watering, spraying, atomizing, broadcasting.

According to the invention, one or more of the ALS inhibitor herbicides belonging to any of the above defined groups (A), (B), and (C) can be applied either alone or in combination with one or more non ALS inhibitor herbicides belonging to group (DO) to the plants (for example harmful plants, such as monocotyledonous or dicotyledonous weeds or unwanted crop plants), the seed (for example grains, seeds or vegetative propagation organs, such as tubers or shoot parts with buds) or the area under cultivation (for example the soil), preferably to the green plants and parts of plants and, if appropriate, additionally the soil. One possible use is the joint application of the active compounds in the form of tank mixes, where the optimally formulated concentrated formulations of the individual active compounds are, together, mixed in a tank with water, and the spray liquor obtained is applied.

ALS Activity Tolerance

For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope.

"Herbicide resistance" or "herbicide tolerance" can, be measured as described in the present application, i.e., by comparing injury of plants when treated with herbecides or, e.g., it can be measured by comparison of AHAS activity obtained from cell extracts from plants containing the mutagenized AHAS sequence and from plants lacking the mutagenized AHAS sequence in the presence of an AHAS inhibitor, such as foramsulfuron or imazamox, using the methods disclosed in Singh, et al. Anal. Biochem., (1988), 171: 173-179. In one embodiment, resistant or tolerant plants demonstrate greater than 25% uninhibition using the methods disclosed in Singh et al (1988) when assayed, e.g., using 10 µM foramsulfuron or 10 µM imazamox.

Seed Deposits

A representative sample of seeds of oilseed rape line SR002201 were deposited by Bayer CropScience AG on Feb. 21, 2011 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 41813.

A representative sample of seeds of oilseed rape line FM202 were deposited by Bayer CropScience AG on Feb. 21, 2011 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 41812.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Biological Examples

Selection for Obtaining ALS Inhibitor Tolerant *B. napus* Plants

The making, selection and propagation of the respective ALS inhibitor herbicide tolerant *B. napus* mutants and their progenies that were used in all the biological examples disclosed subsequently is described in detail in the European Patent Application having the title "ALS inhibitor herbicide tolerant *B. napus* mutants" and which was filed electronically on the same day (Apr. 5, 2011) at the European Patent Office as present application and of which Bayer CropScience AG is an applicant, and which has received the Application number EP 11164720.2.

Preparation of the Spray Mixtures

The individual components herbicide and surfactant with regard to type and application rate as stated in table 1 were added with stirring to a water application rate of 300 l/ha so that a homogeneous spray mixture was formed. The adjuvant Mero® (Bayer CropScience AG: active ingredient is 81% rapeseed oil methyl ester) was always added to the spray liquids with a use rate of one l/ha.

Biological Examples

The abbreviations used herein below denote:
a.i.=active ingredient g a.i./ha=grams of active substance/hectare l/ha=liter/hectare ALS-Inhibitors=Acetolactate Synthetase Inhibitors Seeds of *B. napus* were sown in a sandy loam soil and placed in a climate chamber in a greenhouse under good growth conditions (16 h light, temperature day 14° C., night: 8° C.). The plants (10 per experiment) were grown up to growth stage of BBCH 12 to BBCH 13. The plants were treated on a track sprayer with spray mixtures which had been prepared in accordance with the examples. After the treatment, the plants were returned to the climate chamber.

Visual scoring 14 days after the application gave the results shown in Table 1. Visual scoring was carried out using a percentage scale of 0%=no damage to 100%=all plants dead.

The ALS-inhibitor tolerance of the mutant FM 202 compared to a wild type variety is clearly shown in table 1.

Wild type seeds SR002201 for microspore isolation, culture and selection experiments of mutants have been deposited with the NCIMB, Aberdeen, UK, under Number NCIMB 41813.

TABLE 1

| | | Herbicide injury on BRSNS [%] | |
|---|---|---|---|
| Herbicide | g a.i./ha | SR002201 | FM 202 |
| Foramsulfuron | 35 | 75 | 0 |
| Iodosulfuron | 7 | 95 | 0 |
| Thiencarbazone | 20 | 90 | 0 |
| A1-87 | 15 | 95 | 0 |
| Metsulfuron | 8 | 93 | 0 |
| Amidosulfuron | 30 | 93 | 0 |
| Ethoxysulfuron | 60 | 98 | 0 |
| Mesosulfuron | 15 | 90 | 0 |
| Chlorsulfuron | 9 | 97 | 0 |
| Tribenuron | 30 | 95 | 3 |
| Triflusulfuron | 20 | 65 | 0 |
| Imazamox | 40 | 93 | 0 |

P150-Values (=Negative Logarithm of the Molar Concentration Inhibiting the Enzyme Activity by 50%) for *A. thaliana* Wild-Type, A205V-, W574L- and S653N-Mutant ALS Genes The coding sequences of the *Arabidosis thaliana* wild-type and the A205V-, W574L- and S653N-mutant ALS genes were cloned into Novagen pET-32a(+) vectors and the vectors transformed into *Escherichia coli* AD494 according to the instructions of the manufacturer. Bacteria were grown at 37° C. in LB-medium containing 100 mg/l carbenicillin and 25 mg/l canamycin, induced with 1 mM isopropyl-β-D-thiogalactopyranoside at an $OD_{600}$ of 0.6, cultivated for 16 hours at 18° C. and harvested by centrifugation. Bacterial pellets were resuspended in 100 mM sodium phosphate buffer pH 7.0 containing 0.1 mM thiamine-pyrophosphate, 1 mM $MgCl_2$, and 1 μM FAD at a concentration of 1 gram wet weight per 25 ml of buffer and disrupted by sonification. The crude protein extract obtained after centrifugation was used for ALS activity measurements.

ALS assays were carried out in 96-well microtiter plates using a modification of the procedure described by Ray (1984), Plant Physiol 75:827-831. The reaction mixture contained 20 mM potassium phosphate buffer pH 7.0, 20 mM sodium pyruvate, 0.45 mM thiamine-pyrophosphate, 0.45 mM MgCl$_2$, 9 µM FAD, ALS enzyme and various concentrations of ALS inhibitors in a final volume of 90 µl. Assays were initiated by adding enzyme and terminated after 75 min incubation at 30° C. by the addition of 40 µl 0.5 M H$_2$SO$_4$. After 60 min at room temperature 80 µl of a solution of 1.4% α-naphtol and 0.14% creatine in 0.7 M NaOH was added and after an additional 45 min incubation at room temperature the absorbance was determined at 540 nm. pI50-values for inhibition of ALS were determined as described by Ray (1984), using the XLFit Excel add-in version 4.3.1 curve fitting program of ID Business Solutions Limited.

| Name | ALS PI50 WT | st. dev. | ALS PI50 W574L | st. dev. | ALS PI50 A205V | st. dev. | ALS PI50 S653N | st. dev. |
|---|---|---|---|---|---|---|---|---|
| Amidosulfuron | 6.7 | 0.2 | <4 | | 4.9 | 0.3 | 8.9 | |
| Bispyribac-sodium | 7.8 | 0.2 | 5.1 | | 7.0 | | 6.8 | |
| Ethoxysulfuron | 8.0 | 0.9 | <4 | | 6.0 | 0.8 | 7.8 | |
| Flazasulfuron | 8.6 | 0.5 | 5.5 | 0.2 | 7.8 | | n.m. | |
| Florasulam | 7.9 | 0.1 | 4.6 | 0.1 | 6.1 | | 7.6 | |
| Flupyrsulfuron-methyl | 8.4 | | 5.4 | 0.1 | 7.5 | 0.1 | n.m. | |
| Foramsulfuron | 8.2 | 0.2 | 4.3 | 0.0 | 6.3 | 0.1 | 7.3 | |
| Imazamox | 5.4 | 0.2 | <4 | | <4 | | <4 | |
| Iodosulfuron-methy-sodium | 8.7 | 0.4 | 5.8 | 0.2 | 6.4 | 0.3 | 7.6 | |
| Mesosulfuron-methyl | 9.1 | 0.5 | 4.4 | 0.1 | 6.6 | 0.1 | 7.7 | |
| Metosulam | 8.5 | 0.1 | 4.7 | 0.2 | 6.1 | | 7.4 | |
| Metsulfuron-methyl | 8.0 | 0.2 | 5.0 | 0.3 | 6.0 | 0.2 | 7.3 | |
| Nicosulfuron | 7.2 | 0.1 | <4 | | 6.0 | | 5.8 | |
| Propoxycarbazone | 7.9 | 0.2 | 5.2 | 0.1 | 6.7 | | 6.5 | |
| Rimsulfuron | 8.0 | | 5.0 | 0.1 | 6.8 | | 8.6 | |
| Sulfosulfuron | 7.8 | | <4 | | 5.9 | | 7.1 | |
| Thiencarbazone-methyl | 8.0 | 0.3 | 4.9 | 0.5 | 6.4 | 0.2 | 6.0 | |
| Thifensulfuron-Methyl | 7.5 | 0.2 | 4.2 | | 6.2 | | 6.8 | | n.m. = not measured
if no standard deviation is given, the IP50 value of a compound was measured only once

The invention claimed is:

1. An ALS inhibitor herbicide applied to *Brassica* growing area, comprising a *Brassica* plant comprising an altered ALS I *Brassica* polypeptide comprising an amino acid different from an amino acid corresponding to position alanine205 (A205) of SEQ ID NO: 10, wherein said amino acid different from alanine is valine; and an altered ALS III *Brassica* polypeptide comprising an amino acid different from an amino acid corresponding to position tryptophan574 (W574) of SEQ ID NO: 10, wherein said amino acid different from tryptophan is leucine, wherein said ALS inhibitor herbicide is effective in controlling unwanted vegetation in said *Brassica* growing area.

2. The ALS inhibitor herbicide according to claim 1, wherein said ALS inhibitor herbicide belongs to at least one of:
a group of (sulfon)amides (group (A)) comprising:
a subgroup (AI) of sulfonylureas, comprising:
amidosulfuron [CAS RN 120923-37-7] (=A1-1);
azimsulfuron [CAS RN 120162-55-2] (=A1-2);
bensulfuron-methyl [CAS RN 83055-99-6] (=A1-3);
chlorimuron-ethyl [CAS RN 90982-32-4] (=A1-4);
chlorsulfuron [CAS RN 64902-72-3] (=A1-5);
cinosulfuron [CAS RN 94593-91-6] (=A1-6);
cyclosulfamuron [CAS RN 136849-15-5] (=A1-7);
ethametsulfuron-methyl [CAS RN 97780-06-8] (=A1-8);
ethoxysulfuron [CAS RN 126801-58-9] (=A1-9);
flazasulfuron [CAS RN 104040-78-0] (=A1-10);
flucetosulfuron [CAS RN 412928-75-7] (=A1-11);
flupyrsulfuron-methyl-sodium [CAS RN 144740-54-5] (=A1-12);
foramsulfuron [CAS RN 173159-57-4] (=A1-13);
halosulfuron-methyl [CAS RN 100784-20-1] (=A1-14);
imazosulfuron [CAS RN 122548-33-8] (=A1-15);
iodosulfuron-methyl-sodium [CAS RN 144550-36-7] (=A1-16);
mesosulfuron-methyl [CAS RN 208465-21-8] (=A1-17);
metsulfuron-methyl [CAS RN 74223-64-6] (=A1-18);
monosulfuron [CAS RN 155860-63-2] (=A1-19);
nicosulfuron [CAS RN 111991-09-4] (=A1-20);
orthosulfamuron [CAS RN 213464-77-8] (=A1-21);
oxasulfuron [CAS RN 144651-06-9] (=A1-22);
primisulfuron-methyl [CAS RN 86209-51-0] (=A1-23);
prosulfuron [CAS RN 94125-34-5] (=A1-24);
pyrazosulfuron-ethyl [CAS RN 93697-74-6] (=A1-25);
rimsulfuron [CAS RN 122931-48-0] (=A1-26);
sulfometuron-methyl [CAS RN 74222-97-2] (=A1-27);
sulfosulfuron [CAS RN 141776-32-1] (=A1-28);
thifensulfuron-methyl [CAS RN 79277-27-3] (=A1-29);
triasulfuron [CAS RN 82097-50-5] (=A1-30);

tribenuron-methyl [CAS RN 101200-48-0] (=A1-31);
trifloxysulfuron [CAS RN 145099-21-4] (sodium) (=A1-32);
triflusulfuron-methyl [CAS RN 126535-15-7] (=A1-33);
tritosulfuron [CAS RN 142469-14-5] (=A1-34);
NC-330 [CAS RN 104770-29-8] (=A1-35);
NC-620 [CAS RN 868680-84-6] (=A1-36);
TH-547 [CAS RN 570415-88-2] (=A1-37);
monosulfuron-methyl [CAS RN 175076-90-1] (=A1-38);
2-iodo-N-[(4-methoxy-6-methyl-1,3,5-triazinyl)carbamoyl]benzene-sulfonamide (=A1-39);
a compound of formula (I)

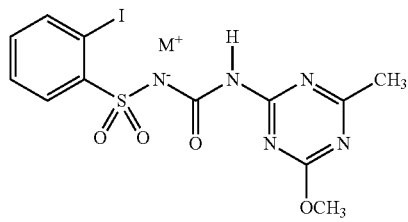

(I)

where M+ denotes a respective salt of compound (I), optionally a lithium salt (=A1-40); a sodium salt (=A1-41); a potassium salt (=A1-42); a magnesium salt (=A1-43); a Calcium (=A1-44); an ammonium salt (=A1-45); a methylammonium salt (=A1-46); a dimethylammonium salt (=A1-47); a tetramethylammonium salt (=A1-48); an ethylammonium salt (=A1-49); a diethylammonium salt (=A1-50); a tetraethylammonium salt (=A1-51); a propylammonium salt (=A1-52); a tetrapropylammonium salt (=A1-53); an isopropylammonium salt (=A1-54); a diisopropylammonium salt (=A1-55); a butylammonium salt (=A1-56); a tetrabutylammonium salt (=A1-57); a (2-hydroxyeth-1-yl)ammonium salt (=A1-58); a bis-N,N-(2-hydroxyeth-1-yl)ammonium salt (=A1-59); a tris-N,N,N-(2-hydroxyeth-1-yl)ammonium salt (=A1-60); a phenylethylammonium salt (=A1-61); a 2-phenylethylammonium salt (=A1-62); a trimethylsulfonium salt (=A1-63); a trimethyloxonium salt (=A1-64); a pyridinium salt (=A1-65); a 2-methylpyridinium salt (=A1-66); a 4-methylpyridinium salt (=A1-67); a 2,4-dimethylpyridinium salt (=A1-68); a 2,6-dimethylpyridinium salt (=A1-69); a piperidinium salt (=A1-70); an imidazolium salt (=A1-71); a morpholinium salt (=A1-72); a 1,5-diazabicyclo[4.3.0]non-7-enium salt (=A1-73); and/or a 1,8-diazabicyclo[5.4.0]undec-7-enium salt (=A1-74);
or a compound of formula (II) and/or a salt thereof

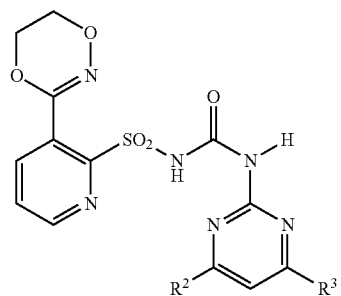

(II)

with $R^2$, and $R^3$ having the meaning as defined in the below table

| Compound | $R^2$ | $R^3$ |
|---|---|---|
| A1-75 | $OCH_3$ | $OC_2H_5$ |
| A1-76 | $OCH_3$ | $CH_3$ |
| A1-77 | $OCH_3$ | $C_2H_5$ |
| A1-78 | $OCH_3$ | $CF_3$ |
| A1-79 | $OCH_3$ | $OCF_2H$ |
| A1-80 | $OCH_3$ | $NHCH_3$ |
| A1-81 | $OCH_3$ | $N(CH_3)_2$ |
| A1-82 | $OCH_3$ | Cl |
| A1-83 | $OCH_3$ | $OCH_3$ |
| A1-84 | $OC_2H_5$ | $OC_2H_5$ |
| A1-85 | $OC_2H_5$ | $CH_3$ |
| A1-86 | $OC_2H_5$ | $C_2H_5$ | or a compound of formula (III) (=A1-87), optionally a sodium salt of compound (A1-83)

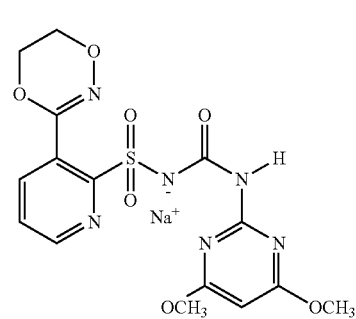

(III)

And/or a compound of formula (IV) (=A1-88), optionally a sodium salt of compound (A1-82)

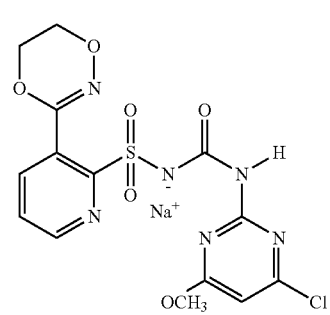

(IV)

a subgroup of sulfonylaminocarbonyltriazolinones (subgroup ((A2)), comprising:
flucarbazone-sodium [CAS RN 181274-17-9] (=A2-1);
propoxycarbazone-sodium [CAS RN 181274-15-7] (=A2-2);
thiencarbazone-methyl [CAS RN 317815-83-1] (=A2-3);
a subgroup of thetriazolopyrimidines (subgroup (A2)), comprising:
cloransulam-methyl [147150-35-4] (=A3-1);
diclosulam [CAS RN 145701-21-9] (=A3-2);
florasulam [CAS RN 145701-23-1] (=A3-3);
flumetsulam [CAS RN 98967-40-9] (=A3-4);
metosulam [CAS RN 139528-85-1] (=A3-5);

penoxsulam [CAS RN 219714-96-2] (=A3-6);
pyroxsulam [CAS RN 422556-08-9] (=A3-7);
a subgroup of sulfonanilides (subgroup (A4)), comprising:
a compound and/or a salt thereof from the group described by formula (I):

(V)

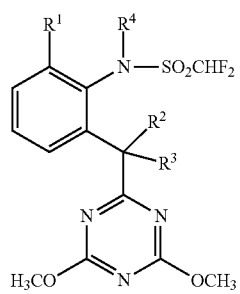

in which $R^1$ is halogen, optionally fluorine or chlorine, $R^2$ is hydrogen and $R^3$ is hydroxyl or $R^2$ and $R^3$ together with the carbon atom to which they are attached are a carbonyl group C=O and $R^4$ is hydrogen or methyl;

and optionally a compound of the below given chemical structure (A4-1) to (A4-8)

(A4-1)
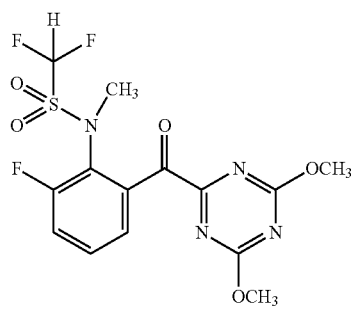

(A4-2)
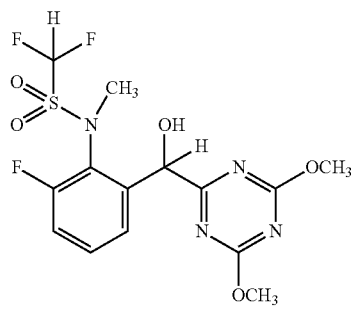

(A4-3)
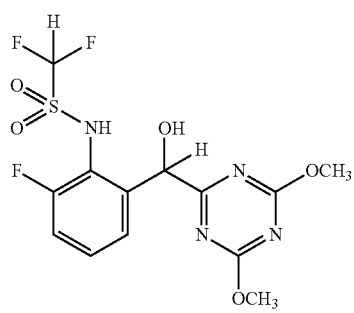

(A4-4)
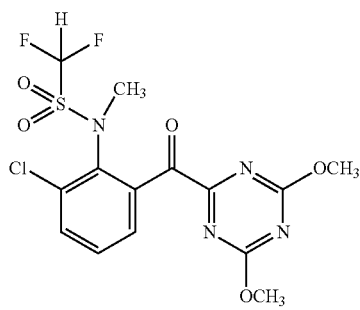

(A4-5)
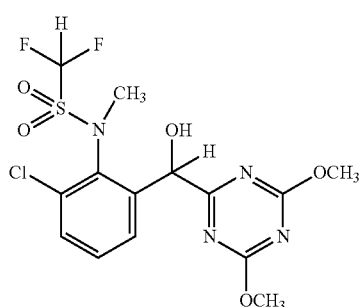

(A4-6)
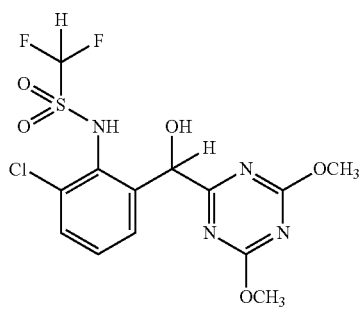

(A4-7)
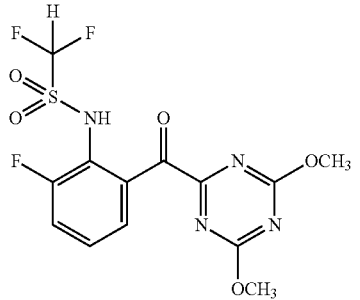

(A4-8)
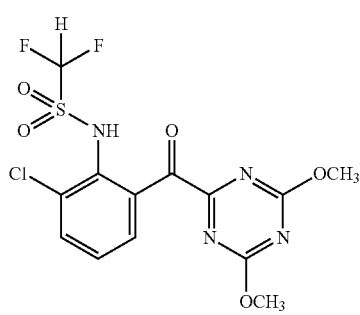

a group of imidazolinones (group (B)), comprising:
imazamethabenzmethyl [CAS RN 81405-85-8] (=B1-1);
imazamox [CAS RN 114311-32-9] (=B1-2);

imazapic [CAS RN 104098-48-8] (=B1-3);
imazapyr [CAS RN 81334-34-1] (=B1-4);
imazaquin [CAS RN 81335-37-7] (=B1-5);
imazethapyr [CAS RN 81335-77-5] (=B1-6);
SYP-298 [CAS RN 557064-77-4] (=B1-7); and
SYP-300 [CAS RN 374718-10-2] (=B1-8);
a group of pyrimidinyl(thio)benzoates (group (C)), comprising:
  a subgroup of pyrimidinyloxybenzoeacids (subgroup (C1)) comprising:
    bispyribac-sodium [CAS RN 125401-92-5] (=C1-1);
    pyribenzoxim [CAS RN 168088-61-7] (=C1-2);
    pyriminobac-methyl [CAS RN 136191-64-5] (=C1-3);
    pyribambenz-isopropyl [CAS RN 420138-41-6] (=C1-4); and
    pyribambenz-propyl [CAS RN 420138-40-5] (=C1-5);
  a subgroup of pyrimidinylthiobenzoeacids (subgroup (C2)), comprising:
    pyriftalid [CAS RN 135186-78-6] (=C2-1); and
    pyrithiobac-sodium [CAS RN 123343-16-8] (=C2-2).

3. The ALS inhibitor herbicide according to claim 1, wherein said ALS inhibitor herbicide comprises:
amidosulfuron [CAS RN 120923-37-7] (=A1-1);
chlorimuron-ethyl [CAS RN 90982-32-4] (=A1-4);
chlorsulfuron [CAS RN 64902-72-3] (=A1-5);
ethametsulfuron-methyl [CAS RN 97780-06-8] (=A1-8);
ethoxysulfuron [CAS RN 126801-58-9] (=A1-9);
flupyrsulfuron-methyl-sodium [CAS RN 144740-54-5] (=A1-12);
foramsulfuron [CAS RN 173159-57-4] (=A1-13);
iodosulfuron-methyl-sodium [CAS RN 144550-36-7] (=A1-16);
mesosulfuron-methyl [CAS RN 208465-21-8] (=A1-17);
metsulfuron-methyl [CAS RN 74223-64-6] (=A1-18);
monosulfuron [CAS RN 155860-63-2] (=A1-19);
nicosulfuron [CAS RN 111991-09-4] (=A1-20);
rimsulfuron [CAS RN 122931-48-0] (=A1-26);
sulfosulfuron [CAS RN 141776-32-1] (=A1-28);
thifensulfuron-methyl [CAS RN 79277-27-3] (=A1-29);
tribenuron-methyl [CAS RN 101200-48-0] (=A1-31);
triflusulfuron-methyl [CAS RN 126535-15-7] (=A1-33);
2-iodo-N-[(4-methoxy-6-methyl-1,3,5-triazinyl)carbamoyl]benzene-sulfonamide (=A1-39);
2-iodo-N-[(4-methoxy-6-methyl-1,3,5-triazinyl)carbamoyl]benzene-sulfonamide sodium salt (=A1-41);
(A1-83) or its sodium salt (=A1-87);
flucarbazone-sodium [CAS RN 181274-17-9] (=A2-1);
propoxycarbazone-sodium [CAS RN 181274-15-7] (=A2-2);
thiencarbazone-methyl [CAS RN 317815-83-1] (=A2-3);
florasulam [CAS RN 145701-23-1] (=A3-3);
metosulam [CAS RN 139528-85-1] (=A3-5);
pyroxsulam [CAS RN 422556-08-9] (=A3-7)
(A4-1);
(A4-2);
(A4-3);
imazamox [CAS RN 114311-32-9] (=B1-2); and/or
bispyribac-sodium [CAS RN 125401-92-5] (=C1-1).

4. The ALS inhibitor herbicide according to claim 1, wherein the ALS inhibitor herbicide comprises:
amidosulfuron [CAS RN 120923-37-7] (=A1-1);
foramsulfuron [CAS RN 173159-57-4] (=A1-13);
sodium salt of compound of formula (I) (=A1-41);
compound of formula (III) (=A1-41);
thiencarbazone-methyl [CAS RN 317815-83-1] (=A2-3);
imazamox [CAS RN 114311-32-9] (=B1-2); and/or
bispyribac-sodium [CAS RN 125401-92-5] (=C1-1).

5. The ALS inhibitor herbicide according to claim 1, wherein the *Brassica* plant comprises a *B. napus* plant comprising an ALS I *B. napus* polypeptide containing an amino acid different from alanine at a position of said ALS I *B. napus* polypeptide corresponding to position 190 of SEQ ID NO: 2, wherein said amino acid different form alanine is valine, and wherein an ALS III *B. napus* polypeptide containing an amino acid different from tryptophan at a position of said ALS III polypeptide corresponding to position 556 of SEQ ID NO: 4, wherein said amino acid different from tryptophan is leucine.

6. The ALS inhibitor herbicide according to claim 1, in combination with a non-ALS inhibitor optionally a herbicide showing a mode of action that is different from inhibition of an ALS enzyme [acetohydroxyacid synthase; EC 2.2.1.6] (group D herbicides), and wherein the non ALS inhibitor herbicide is selected from the group consisting of:
acetochlor (=D1), carbetamide (=D56), fenoxaprop-P-ethyl (=D164), fluazifop-P-butyl (=D174), haloxyfop-P-methyl (=D222), metolachlor (=D275), dimethenamid (=D132), napropamide (=D290), pethoxamid (=D317), propaquizafop (=D341), propisochlor (=D344), propyzamide (=D345), quinmerac (=D363), propachlor (D 427), clomazone (=D83), clopyralid (=D86), dimethachlor (=D130), metazachlor (=D265), picloram (=D321), and quizalofop-P-ethyl (=D368).

7. The ALS inhibitor herbicide according to claim 6, and wherein the non ALS inhibitor herbicide is selected from the group consisting of:
clomazone (=D83), clopyralid (=D86), dimethachlor (=D130), metazachlor (=D265), picloram (=D321), and quizalofop-P-ethyl (=D368).

8. A method for controlling unwanted vegetation in the *Brassica* growing area, comprising applying an ALS inhibitor herbicide as defined in claim 3 to the area.

9. A method for controlling unwanted vegetation in the *Brassica* growing area comprising applying an ALS inhibitor herbicide as defined in claim 3 to the area.

10. The method according to claim 8 further comprising applying a non ALS inhibitor herbicide comprising at least one of: acetochlor (=D1), carbetamide (=D56), fenoxaprop-P-ethyl (=D164), fluazifop-P-butyl (=D174), haloxyfop-P-methyl (=D222), metolachlor (=D275), dimethenamid (=D132), napropamide (=D290), pethoxamid (=D317), propaquizafop (=D341), propisochlor (=D344), propyzamide (=D345), quinmerac (=D363), propachlor (D427), clomazone (=D83), clopyralid (=D86), dimethachlor (=D130), metazachlor (=D265), picloram (=D321), and quizalofop-P-ethyl (=D368) to the area.

11. The method according to claim 10, and wherein the non ALS inhibitor herbicide is selected from the group consisting of clomazone (=D83), clopyralid (=D86), dimethachlor (=D130), metazachlor (=D265), picloram (=D321), and quizalofop-P-ethyl (=D368).

12. A method for controlling unwanted vegetation in a *B. napus* plant growing area comprising applying to the area at least one ALS inhibitor herbicide alone or in combination with at least one herbicide that do(es) not belong to a class of ALS inhibitor herbicides for weed control in the *B. napus* plant growing area said *B. napus* plant in the area comprising an altered ALS I *Brassica* polypeptide comprising an amino acid different from an amino acid corresponding to position alanine205 (A205) of SEQ ID NO: 10, wherein said amino acid different from alanine is valine; and an altered ALS III *Brassica* polypeptide comprising an amino acid different from an amino acid corresponding to position tryptophan574 (W574) of SEQ ID NO: 10, wherein said amino acid different from tryptophan is leucine.

\* \* \* \* \*

```
                        SEQUENCE LISTING

<160> NUMBER OF SEQ ID NOS: 10

<210> SEQ ID NO 1
<211> LENGTH: 1968
<212> TYPE: DNA
<213> ORGANISM: Brassica napus

<400> SEQUENCE: 1
atggcggcgg caacatcgtc ttctccgatc tccttaaccg ctaaaccttc ttccaaatcc     60
cctctaccca tttccagatt ctcccttccc ttctccttaa ccccacagaa agactcctcc    120
cgtctccacc gtcctctcgc catctccgcc gttctcaact cacccgtcaa tgtcgcacct    180
ccttcccctg aaaaaaccga caagaacaag actttcgtct cccgctacgc tcccgacgag    240
ccccgcaagg gtgctgatat cctcgtcgaa gccctcgagc gtcaaggcgt cgaaaccgtc    300
tttgcttatc ccggaggtgc ttccatggag atccaccaag ccttgactcg ctcctccacc    360
atccgtaacg tccttccccg tcacgaacaa ggaggagtct tcgccgccga gggttacgct    420
cgttcctccg gcaaaccggg aatctgcata gccacttcgg gtcccggagc taccaacctc    480
gtcagcgggt tagcagacgc gatgcttgac agtgttcctc ttgtcgccat tacaggacag    540
gtccctcgcc ggatgatcgg tactgacgcc ttccaagaga caccaatcgt tgaggtaacg    600
aggtctatta cgaaacataa ctatttggtg atggatgttg atgacatacc taggatcgtt    660
caagaagctt tctttctagc tacttccggt agacccggac cggttttggt tgatgttcct    720
aaggatattc agcagcagct tgcgattcct aactgggatc aacctatgcg cttacctggc    780
tacatgtcta ggttgcctca gcctccggaa gtttctcagt taggtcagat cgttaggttg    840
atctcggagt ctaagaggcc tgtttttgtac gttggtggtg aagcttgaa ctcgagtgaa    900 gaactgggga gatttgtcga gcttactggg atccccgttg cgagtacttt gatggggctt    960
```

```
ggctcttatc cttgtaacga tgagttgtcc ctgcagatgc ttggcatgca cgggactgtg    1020
tatgctaact acgctgtgga gcatagtgat ttgttgctgg cgtttggtgt taggtttgat    1080
gaccgtgtca cgggaaagct cgaggctttc gctagcaggg ctaaaattgt gcacatagac    1140
attgattctg ctgagattgg gaagaataag acacctcacg tgtctgtgtg tggtgatgta    1200
aagctggctt tgcaagggat gaacaaggtt cttgagaacc gggcggagga gctcaagctt    1260
gatttcggtg tttggaggag tgagttgagc gagcagaaac agaagttccc tttgagcttc    1320
aaaacgtttg agaagccat tcctccgcag tacgcgattc agatcctcga cgagctaacc    1380
gaagggaagg caattatcag tactggtgtt ggacagcatc agatgtgggc ggcgcagttt    1440
tacaagtaca ggaagccgag acagtggctg tcgtcatcag gcctcggagc tatgggtttt    1500
ggacttcctg ctgcgattgg agcgtctgtg gcgaaccctg atgcgattgt tgtggatatt    1560
gacggtgatg aagcttcat aatgaacgtt caagagctgg ccacaatccg tgtagagaat    1620
cttcctgtga agatactctt gttaaacaac cagcatcttg gatggtcat gcaatgggaa    1680 gatcggttct acaaagctaa cagagctcac acttatctcg ggacccggc aagggagaac    1740 gagatcttcc ctaacatgct gcagtttgca ggagcttgcg ggattccagc tgcgagagtg    1800
acgaagaaag aagaactccg agaagctatt cagacaatgc tggatacacc aggaccatac    1860
ctgttggatg tgtatgtcc gcaccaagaa catgtgttac cgatgatccc aagtggtggc    1920
actttcaaag atgtaataac agaaggggat ggtcgcacta agtactga                 1968

<210> SEQ ID NO 2
<211> LENGTH: 655
<212> TYPE: PRT
<213> ORGANISM: Brassica napus

<400> SEQUENCE: 2

Met Ala Ala Ala Thr Ser Ser Pro Ile Ser Leu Thr Ala Lys Pro
1               5                   10                  15

Ser Ser Lys Ser Pro Leu Pro Ile Ser Arg Phe Ser Leu Pro Phe Ser
                20                  25                  30

Leu Thr Pro Gln Lys Asp Ser Ser Arg Leu His Arg Pro Leu Ala Ile
            35                  40                  45

Ser Ala Val Leu Asn Ser Pro Val Asn Val Ala Pro Pro Ser Pro Glu
        50                  55                  60

Lys Thr Asp Lys Asn Lys Thr Phe Val Ser Arg Tyr Ala Pro Asp Glu
65                  70                  75                  80

Pro Arg Lys Gly Ala Asp Ile Leu Val Glu Ala Leu Glu Arg Gln Gly
                85                  90                  95

Val Glu Thr Val Phe Ala Tyr Pro Gly Gly Ala Ser Met Glu Ile His
                100                 105                 110

Gln Ala Leu Thr Arg Ser Ser Thr Ile Arg Asn Val Leu Pro Arg His
            115                 120                 125

Glu Gln Gly Gly Val Phe Ala Ala Glu Gly Tyr Ala Arg Ser Ser Gly
        130                 135                 140

Lys Pro Gly Ile Cys Ile Ala Thr Ser Gly Pro Gly Ala Thr Asn Leu
145                 150                 155                 160

Val Ser Gly Leu Ala Asp Ala Met Leu Asp Ser Val Pro Leu Val Ala
                165                 170                 175

Ile Thr Gly Gln Val Pro Arg Arg Met Ile Gly Thr Asp Ala Phe Gln
                180                 185                 190
```

Glu Thr Pro Ile Val Glu Val Thr Arg Ser Ile Thr Lys His Asn Tyr
            195                 200                 205

Leu Val Met Asp Val Asp Ile Pro Arg Ile Val Gln Glu Ala Phe
    210                 215                 220

Phe Leu Ala Thr Ser Gly Arg Pro Gly Pro Val Leu Asp Val Pro
225                 230                 235                 240

Lys Asp Ile Gln Gln Gln Leu Ala Ile Pro Asn Trp Asp Gln Pro Met
                245                 250                 255

Arg Leu Pro Gly Tyr Met Ser Arg Leu Pro Gln Pro Pro Glu Val Ser
                260                 265                 270

Gln Leu Gly Gln Ile Val Arg Leu Ile Ser Glu Ser Lys Arg Pro Val
            275                 280                 285

Leu Tyr Val Gly Gly Gly Ser Leu Asn Ser Ser Glu Glu Leu Gly Arg
    290                 295                 300

Phe Val Glu Leu Thr Gly Ile Pro Val Ala Ser Thr Leu Met Gly Leu
305                 310                 315                 320

Gly Ser Tyr Pro Cys Asn Asp Glu Leu Ser Leu Gln Met Leu Gly Met
                325                 330                 335

His Gly Thr Val Tyr Ala Asn Tyr Ala Val Glu His Ser Asp Leu Leu
            340                 345                 350

Leu Ala Phe Gly Val Arg Phe Asp Asp Arg Val Thr Gly Lys Leu Glu
            355                 360                 365

Ala Phe Ala Ser Arg Ala Lys Ile Val His Ile Asp Ile Asp Ser Ala
    370                 375                 380

Glu Ile Gly Lys Asn Lys Thr Pro His Val Ser Val Cys Gly Asp Val
385                 390                 395                 400

Lys Leu Ala Leu Gln Gly Met Asn Lys Val Leu Glu Asn Arg Ala Glu
                405                 410                 415

Glu Leu Lys Leu Asp Phe Gly Val Trp Arg Ser Glu Leu Ser Glu Gln
            420                 425                 430

Lys Gln Lys Phe Pro Leu Ser Phe Lys Thr Phe Gly Glu Ala Ile Pro
    435                 440                 445

Pro Gln Tyr Ala Ile Gln Ile Leu Asp Glu Leu Thr Glu Gly Lys Ala
    450                 455                 460

Ile Ile Ser Thr Gly Val Gly Gln His Gln Met Trp Ala Ala Gln Phe
465                 470                 475                 480

Tyr Lys Tyr Arg Lys Pro Arg Gln Trp Leu Ser Ser Ser Gly Leu Gly
                485                 490                 495

Ala Met Gly Phe Gly Leu Pro Ala Ala Ile Gly Ala Ser Val Ala Asn
                500                 505                 510

Pro Asp Ala Ile Val Val Asp Ile Asp Gly Asp Gly Ser Phe Ile Met
            515                 520                 525

Asn Val Gln Glu Leu Ala Thr Ile Arg Val Glu Asn Leu Pro Val Lys
    530                 535                 540

Ile Leu Leu Leu Asn Asn Gln His Leu Gly Met Val Met Gln Trp Glu
545                 550                 555                 560

Asp Arg Phe Tyr Lys Ala Asn Arg Ala His Thr Tyr Leu Gly Asp Pro
                565                 570                 575

Ala Arg Glu Asn Glu Ile Phe Pro Asn Met Leu Gln Phe Ala Gly Ala
            580                 585                 590

Cys Gly Ile Pro Ala Ala Arg Val Thr Lys Lys Glu Glu Leu Arg Glu
    595                 600                 605

Ala Ile Gln Thr Met Leu Asp Thr Pro Gly Pro Tyr Leu Leu Asp Val 610                  615                  620
Ile Cys Pro His Gln Glu His Val Leu Pro Met Ile Pro Ser Gly Gly
625                  630                  635                  640

Thr Phe Lys Asp Val Ile Thr Glu Gly Asp Gly Arg Thr Lys Tyr
              645                  650                  655

<210> SEQ ID NO 3
<211> LENGTH: 1959
<212> TYPE: DNA
<213> ORGANISM: Brassica napus

<400> SEQUENCE: 3

| | |
|---|---|
| atggcggcgg caacatcgtc ttctccgatc tccttaaccg ctaaaccttc ttccaaatcc | 60 |
| cctctaccca tttccagatt ctcccttccc ttctccttaa ccccacagaa accctcctcc | 120 |
| cgtctccacc gtccactcgc catctccgcc gttctcaact cacccgtcaa tgtcgcacct | 180 |
| gaaaaaaccg acaagatcaa gactttcatc tcccgctacg ctcccgacga gccccgcaag | 240 |
| ggtgctgata tcctcgtgga agccctcgag cgtcaaggcg tcgaaaccgt cttcgcttat | 300 |
| cccggaggtg cctccatgga gatccaccaa gccttgactc gctcctccac catccgtaac | 360 |
| gtcctccccc gtcacgaaca aggaggagtc ttcgccgccg agggttacgc tcgttcctcc | 420 |
| ggcaaaccgg gaatctgcat agccacttcg ggtcccggag ctaccaacct cgtcagcggg | 480 |
| ttagccgacg cgatgcttga cagtgttcct ctcgtcgcca tcacaggaca ggtccctcgc | 540 |
| cggatgatcg gtactgacgc gttccaagag acgccaatcg ttgaggtaac gaggtctatt | 600 |
| acgaaacata actatctggt gatggatgtt gatgacatac taggatcgt tcaagaagca | 660 |
| ttctttctag ctacttccgg tagacccgga ccggttttgg ttgatgttcc taaggatatt | 720 |
| cagcagcagc ttgcgattcc taactgggat caacctatgc gcttgcctgg ctacatgtct | 780 |
| aggctgcctc agccaccgga gtttctcag ttaggccaga tcgttaggtt gatctcggag | 840 |
| tctaagaggc ctgttttgta cgttggtggt ggaagcttga actcgagtga gaactgggg | 900 |
| agatttgtcg agcttactgg gatccctgtt gcgagtacgt tgatgggct tggctcttat | 960 |
| ccttgtaacg atgagttgtc cctgcagatg cttggcatgc acgggactgt gtatgctaac | 1020 |
| tacgctgtgg agcatagtga tttgttgctg gcgtttggtg ttaggtttga tgaccgtgtc | 1080 |
| acgggaaagc tcgaggcgtt tgcgagcagg gctaagattg tgcacataga cattgattct | 1140 |
| gctgagattg ggaagaataa gacacctcac gtgtctgtgt gtggtgatgt aaagctggct | 1200 |
| ttgcaaggga tgaacaaggt tcttgagaac cgggcggagg agctcaagct tgatttcggt | 1260 |
| gtttggagga gtgagttgag cgagcagaaa cagaagttcc cgttgagctt caaaacgttt | 1320 |
| ggagaagcca ttcctccgca gtacgcgatt caggtcctag acgagctaac ccaagggaag | 1380 |
| gcaattatca gtactggtgt tggacagcat cagatgtggg cggcgcagtt ttacaagtac | 1440 |
| aggaagccga ggcagtggct gtcgtcctca ggactcggag ctatgggttt cggacttcct | 1500 |
| gctgcgattg gagcgtctgt ggcgaaccct gatgcgattg ttgtggacat tgacggtgat | 1560 |
| ggaagcttca taatgaacgt tcaagagctg gccacaatcc gtgtagagaa tcttcctgtg | 1620 |
| aagatactct tgttaaacaa ccagcatctt gggatggtca tgcaatggga agatcggttc | 1680 |
| tacaaagcta acagagctca cactatctc ggggacccgg caagggagaa cgagatcttc | 1740 |
| cctaacatgc tgcagtttgc aggagcttgc gggattccag ctgcgagagt gacgaagaaa | 1800 |
| gaagaactcc gagaagctat tcagacaatg ctggatacac tggaccgta cctgttggat | 1860 |
| gtcatctgtc cgcaccaaga acatgtgtta ccgatgatcc caagtggtgg cactttcaaa | 1920 |

```
gatgtaataa ccgaagggga tggtcgcact aagtactga                                   1959
```

<210> SEQ ID NO 4
<211> LENGTH: 652
<212> TYPE: PRT
<213> ORGANISM: Brassica napus

<400> SEQUENCE: 4

Met Ala Ala Thr Ser Ser Pro Ile Ser Leu Thr Ala Lys Pro
1               5                   10                  15

Ser Ser Lys Ser Pro Leu Pro Ile Ser Arg Phe Ser Leu Pro Phe Ser
            20                  25                  30

Leu Thr Pro Gln Lys Pro Ser Ser Arg Leu His Arg Pro Leu Ala Ile
        35                  40                  45

Ser Ala Val Leu Asn Ser Pro Val Asn Val Ala Pro Glu Lys Thr Asp
    50                  55                  60

Lys Ile Lys Thr Phe Ile Ser Arg Tyr Ala Pro Asp Glu Pro Arg Lys
65                  70                  75                  80

Gly Ala Asp Ile Leu Val Glu Ala Leu Glu Arg Gln Gly Val Glu Thr
                85                  90                  95

Val Phe Ala Tyr Pro Gly Gly Ala Ser Met Glu Ile His Gln Ala Leu
            100                 105                 110

Thr Arg Ser Ser Thr Ile Arg Asn Val Leu Pro Arg His Glu Gln Gly
        115                 120                 125

Gly Val Phe Ala Ala Glu Gly Tyr Ala Arg Ser Ser Gly Lys Pro Gly
    130                 135                 140

Ile Cys Ile Ala Thr Ser Gly Pro Gly Ala Thr Asn Leu Val Ser Gly
145                 150                 155                 160

Leu Ala Asp Ala Met Leu Asp Ser Val Pro Leu Val Ala Ile Thr Gly
                165                 170                 175

Gln Val Pro Arg Arg Met Ile Gly Thr Asp Ala Phe Gln Glu Thr Pro
            180                 185                 190

Ile Val Glu Val Thr Arg Ser Ile Thr Lys His Asn Tyr Leu Val Met
        195                 200                 205

Asp Val Asp Asp Ile Pro Arg Ile Val Gln Glu Ala Phe Phe Leu Ala
    210                 215                 220

Thr Ser Gly Arg Pro Gly Pro Val Leu Val Asp Val Pro Lys Asp Ile
225                 230                 235                 240

Gln Gln Gln Leu Ala Ile Pro Asn Trp Asp Gln Pro Met Arg Leu Pro
                245                 250                 255

Gly Tyr Met Ser Arg Leu Pro Gln Pro Pro Glu Val Ser Gln Leu Gly
            260                 265                 270

Gln Ile Val Arg Leu Ile Ser Glu Ser Lys Arg Pro Val Leu Tyr Val
        275                 280                 285

Gly Gly Gly Ser Leu Asn Ser Ser Glu Glu Leu Gly Arg Phe Val Glu
    290                 295                 300

Leu Thr Gly Ile Pro Val Ala Ser Thr Leu Met Gly Leu Gly Ser Tyr
305                 310                 315                 320

Pro Cys Asn Asp Glu Leu Ser Leu Gln Met Leu Gly Met His Gly Thr
                325                 330                 335

Val Tyr Ala Asn Tyr Ala Val Glu His Ser Asp Leu Leu Leu Ala Phe
            340                 345                 350

Gly Val Arg Phe Asp Asp Arg Val Thr Gly Lys Leu Glu Ala Phe Ala
        355                 360                 365

```
Ser Arg Ala Lys Ile Val His Ile Asp Ile Asp Ser Ala Glu Ile Gly
    370                 375                 380
Lys Asn Lys Thr Pro His Val Ser Val Cys Gly Asp Val Lys Leu Ala
385                 390                 395                 400
Leu Gln Gly Met Asn Lys Val Leu Glu Asn Arg Ala Glu Glu Leu Lys
                405                 410                 415
Leu Asp Phe Gly Val Trp Arg Ser Glu Leu Ser Glu Gln Lys Gln Lys
            420                 425                 430
Phe Pro Leu Ser Phe Lys Thr Phe Gly Glu Ala Ile Pro Pro Gln Tyr
        435                 440                 445
Ala Ile Gln Val Leu Asp Glu Leu Thr Gln Gly Lys Ala Ile Ile Ser
    450                 455                 460
Thr Gly Val Gly Gln His Gln Met Trp Ala Ala Gln Phe Tyr Lys Tyr
465                 470                 475                 480
Arg Lys Pro Arg Gln Trp Leu Ser Ser Gly Leu Gly Ala Met Gly
                485                 490                 495
Phe Gly Leu Pro Ala Ala Ile Gly Ala Ser Val Ala Asn Pro Asp Ala
            500                 505                 510
Ile Val Val Asp Ile Asp Gly Asp Gly Ser Phe Ile Met Asn Val Gln
        515                 520                 525
Glu Leu Ala Thr Ile Arg Val Glu Asn Leu Pro Val Lys Ile Leu Leu
    530                 535                 540
Leu Asn Asn Gln His Leu Gly Met Val Met Gln Trp Glu Asp Arg Phe
545                 550                 555                 560
Tyr Lys Ala Asn Arg Ala His Thr Tyr Leu Gly Asp Pro Ala Arg Glu
                565                 570                 575
Asn Glu Ile Phe Pro Asn Met Leu Gln Phe Ala Gly Ala Cys Gly Ile
            580                 585                 590
Pro Ala Ala Arg Val Thr Lys Lys Glu Glu Leu Arg Glu Ala Ile Gln
        595                 600                 605
Thr Met Leu Asp Thr Pro Gly Pro Tyr Leu Leu Asp Val Ile Cys Pro
    610                 615                 620
His Gln Glu His Val Leu Pro Met Ile Pro Ser Gly Gly Thr Phe Lys
625                 630                 635                 640
Asp Val Ile Thr Glu Gly Asp Gly Arg Thr Lys Tyr
                645                 650

<210> SEQ ID NO 5
<211> LENGTH: 1968
<212> TYPE: DNA
<213> ORGANISM: Brassica napus

<400> SEQUENCE: 5
atggcggcgg caacatcgtc ttctccgatc tccttaaccg ctaaaccttc ttccaaatcc      60
cctctaccca tttccagatt ctcccttccc ttctccttaa ccccacagaa agactcctcc     120
cgtctccacc gtcctctcgc catctccgcc gttctcaact cacccgtcaa tgtcgcacct     180
ccttcccctg aaaaaaccga caagaacaag actttcgtct cccgctacgc tcccgacgag     240
cccgcaaggt gtgctgatat cctcgtcgaa gccctcgagc gtcaaggcgt cgaaaccgtc     300
tttgcttatc ccggaggtgc ttccatggag atccaccaag ccttgactcg ctcctccacc     360
atccgtaacg tccttccccg tcacgaacaa ggaggagtct tcgccgccga gggttacgct     420
cgttcctccg gcaaaccggg aatctgcata gccacttcgg gtcccggagc taccaacctc     480
```

-continued

```
gtcagcgggt agcagacgc gatgcttgac agtgttcctc ttgtcgccat acaggacag      540
gtccctcgcc ggatgatcgg tactgacgtc ttccaagaga caccaatcgt tgaggtaacg    600
aggtctatta cgaaacataa ctatttggtg atggatgttg atgacatacc taggatcgtt   660
caagaagctt tctttctagc tacttccggt agacccggac cggttttggt tgatgttcct    720
aaggatattc agcagcagct tgcgattcct aactgggatc aacctatgcg cttacctggc   780
tacatgtcta ggttgcctca gcctccggaa gtttctcagt taggtcagat cgttaggttg   840
atctcggagt ctaagaggcc tgttttgtac gttggtggtg aagcttgaa ctcgagtgaa    900
gaactgggga gatttgtcga gcttactggg atccccgttg cgagtacttt gatgggctt    960
ggctcttatc cttgtaacga tgagttgtcc ctgcagatgc ttggcatgca cgggactgtg   1020
tatgctaact acgctgtgga gcatagtgat ttgttgctgg cgtttggtgt taggtttgat   1080
gaccgtgtca cgggaaagct cgaggctttc gctagcaggg ctaaaattgt gcacatagac   1140
attgattctg ctgagattgg gaagaataag acacctcacg tgtctgtgtg tggtgatgta   1200
aagctggctt tgcaagggat gaacaaggtt cttgagaacc gggcggagga gctcaagctt   1260
gatttcggtg tttggaggag tgagttgagc gagcagaaac agaagttccc tttgagcttc   1320
aaaacgtttg gagaagccat tcctccgcag tacgcgattc agatcctcga cgagctaacc   1380
gaagggaagg caattatcag tactggtgtt ggacagcatc agatgtgggc ggcgcagttt   1440
tacaagtaca ggaagccgag acagtggctg tcgtcatcag gcctcggagc tatgggtttt   1500
ggacttcctg ctgcgattgg agcgtctgtg gcgaaccctg atgcgattgt tgtggatatt   1560
gacggtgatg gaagcttcat aatgaacgtt caagagctgg ccacaatccg tgtagagaat   1620
cttcctgtga agatactctt gttaaacaac cagcatcttg gatggtcat gcaatgggaa    1680
gatcggttct acaaagctaa cagagctcac acttatctcg ggaccccggc aagggagaac   1740
gagatcttcc ctaacatgct gcagtttgca ggagcttgcg ggattccagc tgcgagagtg   1800
acgaagaaag aagaactccg agaagctatt cagacaatgc tggatacacc aggaccatac   1860
ctgttggatg tgatatgtcc gcaccaagaa catgtgttac cgatgatccc aagtggtggc   1920
actttcaaag atgtaataac agaaggggat ggtcgcacta agtactga                1968
```

<210> SEQ ID NO 6
<211> LENGTH: 655
<212> TYPE: PRT
<213> ORGANISM: Brassica napus

<400> SEQUENCE: 6

```
Met Ala Ala Ala Thr Ser Ser Ser Pro Ile Ser Leu Thr Ala Lys Pro
  1               5                  10                  15

Ser Ser Lys Ser Pro Leu Pro Ile Ser Arg Phe Ser Leu Pro Phe Ser
             20                  25                  30

Leu Thr Pro Gln Lys Asp Ser Ser Arg Leu His Arg Pro Leu Ala Ile
         35                  40                  45

Ser Ala Val Leu Asn Ser Pro Val Asn Val Ala Pro Ser Pro Glu
     50                  55                  60

Lys Thr Asp Lys Asn Lys Thr Phe Val Ser Arg Tyr Ala Pro Asp Glu
 65                  70                  75                  80

Pro Arg Lys Gly Ala Asp Ile Leu Val Glu Ala Leu Glu Arg Gln Gly
                 85                  90                  95

Val Glu Thr Val Phe Ala Tyr Pro Gly Gly Ala Ser Met Glu Ile His
            100                 105                 110
```

```
Gln Ala Leu Thr Arg Ser Ser Thr Ile Arg Asn Val Leu Pro Arg His
            115                 120                 125

Glu Gln Gly Gly Val Phe Ala Ala Glu Gly Tyr Ala Arg Ser Ser Gly
    130                 135                 140

Lys Pro Gly Ile Cys Ile Ala Thr Ser Gly Pro Gly Ala Thr Asn Leu
145                 150                 155                 160

Val Ser Gly Leu Ala Asp Ala Met Leu Asp Ser Val Pro Leu Val Ala
                165                 170                 175

Ile Thr Gly Gln Val Pro Arg Arg Met Ile Gly Thr Asp Val Phe Gln
                180                 185                 190

Glu Thr Pro Ile Val Glu Val Thr Arg Ser Ile Thr Lys His Asn Tyr
            195                 200                 205

Leu Val Met Asp Val Asp Asp Ile Pro Arg Ile Val Gln Glu Ala Phe
        210                 215                 220

Phe Leu Ala Thr Ser Gly Arg Pro Gly Pro Val Leu Val Asp Val Pro
225                 230                 235                 240

Lys Asp Ile Gln Gln Leu Ala Ile Pro Asn Trp Asp Gln Pro Met
                245                 250                 255

Arg Leu Pro Gly Tyr Met Ser Arg Leu Pro Gln Pro Pro Glu Val Ser
            260                 265                 270

Gln Leu Gly Gln Ile Val Arg Leu Ile Ser Glu Ser Lys Arg Pro Val
        275                 280                 285

Leu Tyr Val Gly Gly Gly Ser Leu Asn Ser Ser Glu Glu Leu Gly Arg
    290                 295                 300

Phe Val Glu Leu Thr Gly Ile Pro Val Ala Ser Thr Leu Met Gly Leu
305                 310                 315                 320

Gly Ser Tyr Pro Cys Asn Asp Glu Leu Ser Leu Gln Met Leu Gly Met
                325                 330                 335

His Gly Thr Val Tyr Ala Asn Tyr Ala Val Glu His Ser Asp Leu Leu
                340                 345                 350

Leu Ala Phe Gly Val Arg Phe Asp Asp Arg Val Thr Gly Lys Leu Glu
            355                 360                 365

Ala Phe Ala Ser Arg Ala Lys Ile Val His Ile Asp Ile Asp Ser Ala
        370                 375                 380

Glu Ile Gly Lys Asn Lys Thr Pro His Val Ser Val Cys Gly Asp Val
385                 390                 395                 400

Lys Leu Ala Leu Gln Gly Met Asn Lys Val Leu Glu Asn Arg Ala Glu
                405                 410                 415

Glu Leu Lys Leu Asp Phe Gly Val Trp Arg Ser Glu Leu Ser Glu Gln
            420                 425                 430

Lys Gln Lys Phe Pro Leu Ser Phe Lys Thr Phe Gly Glu Ala Ile Pro
        435                 440                 445

Pro Gln Tyr Ala Ile Gln Ile Leu Asp Glu Leu Thr Glu Gly Lys Ala
    450                 455                 460

Ile Ile Ser Thr Gly Val Gly Gln His Gln Met Trp Ala Ala Gln Phe
465                 470                 475                 480

Tyr Lys Tyr Arg Lys Pro Arg Gln Trp Leu Ser Ser Ser Gly Leu Gly
                485                 490                 495

Ala Met Gly Phe Gly Leu Pro Ala Ala Ile Gly Ala Ser Val Ala Asn
                500                 505                 510

Pro Asp Ala Ile Val Val Asp Ile Asp Gly Asp Gly Ser Phe Ile Met
            515                 520                 525

Asn Val Gln Glu Leu Ala Thr Ile Arg Val Glu Asn Leu Pro Val Lys
```

```
                530             535             540
Ile Leu Leu Leu Asn Asn Gln His Leu Gly Met Val Met Gln Trp Glu
545                 550             555             560

Asp Arg Phe Tyr Lys Ala Asn Arg Ala His Thr Tyr Leu Gly Asp Pro
                565             570             575

Ala Arg Glu Asn Glu Ile Phe Pro Asn Met Leu Gln Phe Ala Gly Ala
            580             585             590

Cys Gly Ile Pro Ala Ala Arg Val Thr Lys Lys Glu Glu Leu Arg Glu
            595             600             605

Ala Ile Gln Thr Met Leu Asp Thr Pro Gly Pro Tyr Leu Leu Asp Val
            610             615             620

Ile Cys Pro His Gln Glu His Val Leu Pro Met Ile Pro Ser Gly Gly
625             630             635             640

Thr Phe Lys Asp Val Ile Thr Glu Gly Asp Gly Arg Thr Lys Tyr
                645             650             655

<210> SEQ ID NO 7
<211> LENGTH: 1959
<212> TYPE: DNA
<213> ORGANISM: Brassica napus

<400> SEQUENCE: 7
```

| | | | | | |
|---|---|---|---|---|---|
| atggcggcgg | caacatcgtc | ttctccgatc | tccttaaccg | ctaaaccttc | ttccaaatcc | 60 |
| cctctaccca | tttccagatt | ctcccttccc | ttctccttaa | ccccacagaa | accctcctcc | 120 |
| cgtctccacc | gtcctctcgc | catctccgcc | gttctcaact | cacccgtcaa | tgtcgcacct | 180 |
| gaaaaaaccg | acaagatcaa | gactttcatc | tcccgctacg | ctcccgacga | gccccgcaag | 240 |
| ggtgctgata | tcctcgtgga | agccctcgag | cgtcaaggcg | tcgaaaccgt | cttcgcttat | 300 |
| cccggaggtg | cctccatgga | gatccaccaa | gccttgactc | gctcctccac | catccgtaac | 360 |
| gtcctccccc | gtcacgaaca | aggaggagtc | ttcgccgccg | agggttacgc | tcgttcctcc | 420 |
| ggcaaaccgg | gaatctgcat | agccacttcg | ggtcccggag | ctaccaacct | cgtcagcggg | 480 |
| ttagccgacg | cgatgcttga | cagtgttcct | ctcgtcgcca | tcacaggaca | ggtccctcgc | 540 |
| cggatgatcg | gtactgacgc | cttccaagag | acgccaatcg | ttgaggtaac | gaggtctatt | 600 |
| acgaaacata | actatctggt | gatggatgtt | gatgacatac | ctaggatcgt | tcaagaagca | 660 |
| ttctttctag | ctacttccgg | tagacccgga | ccggttttgg | ttgatgttcc | taaggatatt | 720 |
| cagcagcagc | ttgcgattcc | taactgggat | caacctatgc | gcttgcctgg | ctacatgtct | 780 |
| aggctgcctc | agccaccgga | agtttctcag | ttaggccaga | tcgttaggtt | gatctcggag | 840 |
| tctaagaggc | ctgttttgta | cgttggtggt | ggaagcttga | actcgagtga | agaactgggg | 900 |
| agatttgtcg | agcttactgg | gatccctgtt | gcgagtacgc | tgatgggct | ggctctttat | 960 |
| ccttgtaacg | atgagttgtc | cctgcagatg | cttggcatgc | acgggactgt | gtatgctaac | 1020 |
| tacgctgtgg | agcatagtga | tttgttgctg | gcgtttggtg | ttaggtttga | tgaccgtgtc | 1080 |
| acgggaaagc | tcgaggcgtt | tgcgagcagg | gctaagattg | tgcacataga | cattgattct | 1140 |
| gctgagattg | gaagaataa | gacacctcac | gtgtctgtgt | gtggtgatgt | aaagctggct | 1200 |
| tgcaaggga | tgaacaaggt | tcttgagaac | cgggcggagg | agctcaagct | tgatttcggt | 1260 |
| gtttggagga | gtgagttgag | cgagcagaaa | cagaagttcc | cgttgagctt | caaaacgttt | 1320 |
| ggagaagcca | ttcctccgca | gtacgcgatt | caggtcctag | acgagctaac | ccaagggaag | 1380 |
| gcaattatca | gtactggtgt | tggacagcat | cagatgtggg | cggcgcagtt | ttacaagtac | 1440 |

```
aggaagccga ggcagtggct gtcgtcctca ggactcggag ctatgggttt cggacttcct    1500
gctgcgattg gagcgtctgt ggcgaaccct gatgcgattg ttgtggacat tgacggtgat    1560
ggaagcttca taatgaacgt tcaagagctg gccacaatcc gtgtagagaa tcttcctgtg    1620
aagatactct tgttaaacaa ccagcatctt gggatggtca tgcaattgga agatcggttc    1680
tacaaagcta acagagctca cacttatctc ggggacccgg caagggagaa cgagatcttc    1740
cctaacatgc tgcagtttgc aggagcttgc gggattccag ctgcgagagt gacgaagaaa    1800
gaagaactcc gagaagctat tcagacaatg ctggatacac ctggaccgta cctgttggat    1860
gtcatctgtc cgcaccaaga acatgtgtta ccgatgatcc caagtggtgg cactttcaaa    1920
gatgtaataa ccgaagggga tggtcgcact aagtactga                            1959
```

<210> SEQ ID NO 8
<211> LENGTH: 652
<212> TYPE: PRT
<213> ORGANISM: Brassica napus

<400> SEQUENCE: 8

```
Met Ala Ala Ala Thr Ser Ser Pro Ile Ser Leu Thr Ala Lys Pro
1               5                   10                  15

Ser Ser Lys Ser Pro Leu Pro Ile Ser Arg Phe Ser Leu Pro Phe Ser
                20                  25                  30

Leu Thr Pro Gln Lys Pro Ser Ser Arg Leu His Arg Pro Leu Ala Ile
            35                  40                  45

Ser Ala Val Leu Asn Ser Pro Val Asn Val Ala Pro Glu Lys Thr Asp
        50                  55                  60

Lys Ile Lys Thr Phe Ile Ser Arg Tyr Ala Pro Asp Glu Pro Arg Lys
65                  70                  75                  80

Gly Ala Asp Ile Leu Val Glu Ala Leu Glu Arg Gln Gly Val Glu Thr
                85                  90                  95

Val Phe Ala Tyr Pro Gly Gly Ala Ser Met Glu Ile His Gln Ala Leu
                100                 105                 110

Thr Arg Ser Ser Thr Ile Arg Asn Val Leu Pro Arg His Glu Gln Gly
            115                 120                 125

Gly Val Phe Ala Ala Glu Gly Tyr Ala Arg Ser Ser Gly Lys Pro Gly
        130                 135                 140

Ile Cys Ile Ala Thr Ser Gly Pro Gly Ala Thr Asn Leu Val Ser Gly
145                 150                 155                 160

Leu Ala Asp Ala Met Leu Asp Ser Val Pro Leu Val Ala Ile Thr Gly
                165                 170                 175

Gln Val Pro Arg Arg Met Ile Gly Thr Asp Ala Phe Gln Glu Thr Pro
                180                 185                 190

Ile Val Glu Val Thr Arg Ser Ile Thr Lys His Asn Tyr Leu Val Met
            195                 200                 205

Asp Val Asp Asp Ile Pro Arg Ile Val Gln Glu Ala Phe Phe Leu Ala
        210                 215                 220

Thr Ser Gly Arg Pro Gly Pro Val Leu Val Asp Val Pro Lys Asp Ile
225                 230                 235                 240

Gln Gln Gln Leu Ala Ile Pro Asn Trp Asp Gln Pro Met Arg Leu Pro
                245                 250                 255

Gly Tyr Met Ser Arg Leu Pro Gln Pro Pro Glu Val Ser Gln Leu Gly
                260                 265                 270

Gln Ile Val Arg Leu Ile Ser Glu Ser Lys Arg Pro Val Leu Tyr Val
            275                 280                 285
```

Gly Gly Gly Ser Leu Asn Ser Glu Glu Leu Gly Arg Phe Val Glu
            290                 295                 300

Leu Thr Gly Ile Pro Val Ala Ser Thr Leu Met Gly Leu Gly Ser Tyr
305                 310                 315                 320

Pro Cys Asn Asp Glu Leu Ser Leu Gln Met Leu Gly Met His Gly Thr
                325                 330                 335

Val Tyr Ala Asn Tyr Ala Val Glu His Ser Asp Leu Leu Ala Phe
            340                 345                 350

Gly Val Arg Phe Asp Asp Arg Val Thr Gly Lys Leu Glu Ala Phe Ala
            355                 360                 365

Ser Arg Ala Lys Ile Val His Ile Asp Ile Asp Ser Ala Glu Ile Gly
370                 375                 380

Lys Asn Lys Thr Pro His Val Ser Val Cys Gly Asp Val Lys Leu Ala
385                 390                 395                 400

Leu Gln Gly Met Asn Lys Val Leu Glu Asn Arg Ala Glu Glu Leu Lys
            405                 410                 415

Leu Asp Phe Gly Val Trp Arg Ser Glu Leu Ser Glu Gln Lys Gln Lys
            420                 425                 430

Phe Pro Leu Ser Phe Lys Thr Phe Gly Glu Ala Ile Pro Pro Gln Tyr
            435                 440                 445

Ala Ile Gln Val Leu Asp Glu Leu Thr Gln Gly Lys Ala Ile Ile Ser
450                 455                 460

Thr Gly Val Gly Gln His Gln Met Trp Ala Ala Gln Phe Tyr Lys Tyr
465                 470                 475                 480

Arg Lys Pro Arg Gln Trp Leu Ser Ser Gly Leu Gly Ala Met Gly
            485                 490                 495

Phe Gly Leu Pro Ala Ala Ile Gly Ala Ser Val Ala Asn Pro Asp Ala
            500                 505                 510

Ile Val Val Asp Ile Asp Gly Asp Gly Ser Phe Ile Met Asn Val Gln
            515                 520                 525

Glu Leu Ala Thr Ile Arg Val Glu Asn Leu Pro Val Lys Ile Leu Leu
530                 535                 540

Leu Asn Asn Gln His Leu Gly Met Val Met Gln Leu Glu Asp Arg Phe
545                 550                 555                 560

Tyr Lys Ala Asn Arg Ala His Thr Tyr Leu Gly Asp Pro Ala Arg Glu
            565                 570                 575

Asn Glu Ile Phe Pro Asn Met Leu Gln Phe Ala Gly Ala Cys Gly Ile
            580                 585                 590

Pro Ala Ala Arg Val Thr Lys Lys Glu Glu Leu Arg Glu Ala Ile Gln
            595                 600                 605

Thr Met Leu Asp Thr Pro Gly Pro Tyr Leu Leu Asp Val Ile Cys Pro
610                 615                 620

His Gln Glu His Val Leu Pro Met Ile Pro Ser Gly Gly Thr Phe Lys
625                 630                 635                 640

Asp Val Ile Thr Glu Gly Asp Gly Arg Thr Lys Tyr
            645                 650

<210> SEQ ID NO 9
<211> LENGTH: 2013
<212> TYPE: DNA
<213> ORGANISM: Arabidopsis thaliana

<400> SEQUENCE: 9
atggcggcgg caacaacaac aacaacaaca tcttcttcga tctccttctc caccaaacca        60

-continued

```
tctccttcct cctccaaatc accattacca atctccagat tctccctccc attctcccta      120
aaccccaaca aatcatcctc ctcctcccgc cgccgcggta tcaaatccag ctctccctcc      180
tccatctccg ccgtgctcaa cacaaccacc aatgtgacaa ccactccctc tccaaccaaa      240
cctaccaaac ccgaaacatt catctcccga ttcgctccag atcaaccccg caaaggcgct      300
gatatcctcg tcgaagcttt agaacgtcaa ggcgtagaaa ccgtattcgc ttaccctgga      360
ggtgcatcaa tggagattca ccaagcctta acccgctctt cctcaatccg taacgtcctt      420
cctcgtcacg aacaaggagg tgtattcgca gcagaaggat acgctcgatc ctcaggtaaa      480
ccaggtatct gtatagccac ttcaggtccc ggagctacaa atctcgttag cggattagcc      540
gatgcgttgt tagatagtgt tcctcttgta gcaatcacag acaagtccc tcgtcgtatg      600 attggtacag atgcgtttca agagactccg attgttgagg taacgcgttc gattacgaag      660
cataactatc ttgtgatgga tgttgaagat atccctagga ttattgagga agctttcttt      720
ttagctactt ctggtagacc tggacctgtt tggttgatg ttcctaaaga tattcaacaa      780
cagcttgcga ttcctaattg ggaacaggct atgagattac ctggttatat gtctaggatg      840
cctaaacctc cggaagattc tcatttggag cagattgtta ggttgatttc tgagtctaag      900
aagcctgtgt tgtatgttgg tggtggttgt ttgaattcta gcgatgaatt gggtaggttt      960
gttgagctta cggggatccc tgttgcgagt acgttgatgg ggctgggatc ttatccttgt     1020
gatgatgagt tgtcgttaca tatgcttgga atgcatggga ctgtgtatgc aaattacgct     1080
gtggagcata gtgatttgtt gttggcgttt ggggtaaggt ttgatgatcg tgtcacgggt     1140
aagcttgagg cttttgctag tagggctaag attgttcata ttgatattga ctcggctgag     1200
attgggaaga ataagactcc tcatgtgtct gtgtgtggtg atgttaagct ggctttgcaa     1260
gggatgaata aggttcttga gaaccgagcg gaggagctta agcttgattt tggagtttgg     1320
aggaatgagt tgaacgtaca gaaacagaag tttccgttga gctttaagac gtttggggaa     1380
gctattcctc cacagtatgc gattaaggtc cttgatgagt tgactgatgg aaaagccata     1440
ataagtactg gtgtcgggca acatcaaatg tgggcggcgc agttctacaa ttacaagaaa     1500
ccaaggcagt ggctatcatc aggaggcctt ggagctatgg gatttggact tcctgctgcg     1560
attggagcgt ctgttgctaa ccctgatgcg atagttgtgg atattgacgg agatggaagc     1620
tttataatga atgtgcaaga gctagccact attcgtgtag agaatcttcc agtgaaggta     1680
cttttattaa acaaccagca tcttggcatg ttatgcaat ggcaagatcg gttctacaaa     1740
gctaaccgag ctcacacatt tctcggggat ccggctcagg aggacgagat attcccgaac     1800
atgttgctgt ttgcagcagc ttgcgggatt ccagcggcga gggtgacaaa gaaagcagat     1860
ctccgagaag ctattcagac aatgctggat acaccaggac cttacctgtt ggatgtgatt     1920
tgtccgcacc aagaacatgt gttgccgatg atcccgagtg gtggcacttt caacgatgtc     1980
ataacggaag gagatggccg gattaaatac tga                                  2013
```

<210> SEQ ID NO 10
<211> LENGTH: 670
<212> TYPE: PRT
<213> ORGANISM: Arabidopsis thaliana
<400> SEQUENCE: 10

```
Met Ala Ala Ala Thr Thr Thr Thr Thr Ser Ser Ser Ile Ser Phe
1               5                   10                  15

Ser Thr Lys Pro Ser Pro Ser Ser Ser Lys Ser Pro Leu Pro Ile Ser
```

```
                20                  25                  30
Arg Phe Ser Leu Pro Phe Ser Leu Asn Pro Asn Lys Ser Ser Ser
            35                  40                  45
Ser Arg Arg Gly Ile Lys Ser Ser Pro Ser Ser Ile Ser Ala
 50                  55                  60
Val Leu Asn Thr Thr Thr Asn Val Thr Thr Thr Pro Ser Pro Thr Lys
 65                  70                  75                  80
Pro Thr Lys Pro Glu Thr Phe Ile Ser Arg Phe Ala Pro Asp Gln Pro
                85                  90                  95
Arg Lys Gly Ala Asp Ile Leu Val Glu Ala Leu Glu Arg Gln Gly Val
            100                 105                 110
Glu Thr Val Phe Ala Tyr Pro Gly Gly Ala Ser Met Glu Ile His Gln
            115                 120                 125
Ala Leu Thr Arg Ser Ser Ile Arg Asn Val Leu Pro Arg His Glu
            130                 135                 140
Gln Gly Gly Val Phe Ala Ala Glu Gly Tyr Ala Arg Ser Ser Gly Lys
145                 150                 155                 160
Pro Gly Ile Cys Ile Ala Thr Ser Gly Pro Gly Ala Thr Asn Leu Val
                165                 170                 175
Ser Gly Leu Ala Asp Ala Leu Leu Asp Ser Val Pro Leu Val Ala Ile
            180                 185                 190
Thr Gly Gln Val Pro Arg Arg Met Ile Gly Thr Asp Ala Phe Gln Glu
            195                 200                 205
Thr Pro Ile Val Glu Val Thr Arg Ser Ile Thr Lys His Asn Tyr Leu
            210                 215                 220
Val Met Asp Val Glu Asp Ile Pro Arg Ile Ile Glu Glu Ala Phe Phe
225                 230                 235                 240
Leu Ala Thr Ser Gly Arg Pro Gly Pro Val Leu Val Asp Val Pro Lys
                245                 250                 255
Asp Ile Gln Gln Gln Leu Ala Ile Pro Asn Trp Glu Gln Ala Met Arg
            260                 265                 270
Leu Pro Gly Tyr Met Ser Arg Met Pro Lys Pro Pro Glu Asp Ser His
            275                 280                 285
Leu Glu Gln Ile Val Arg Leu Ile Ser Glu Ser Lys Lys Pro Val Leu
            290                 295                 300
Tyr Val Gly Gly Gly Cys Leu Asn Ser Ser Asp Glu Leu Gly Arg Phe
305                 310                 315                 320
Val Glu Leu Thr Gly Ile Pro Val Ala Ser Thr Leu Met Gly Leu Gly
                325                 330                 335
Ser Tyr Pro Cys Asp Asp Glu Leu Ser Leu His Met Leu Gly Met His
                340                 345                 350
Gly Thr Val Tyr Ala Asn Tyr Ala Val Glu His Ser Asp Leu Leu Leu
            355                 360                 365
Ala Phe Gly Val Arg Phe Asp Asp Arg Val Thr Gly Lys Leu Glu Ala
            370                 375                 380
Phe Ala Ser Arg Ala Lys Ile Val His Ile Asp Ile Asp Ser Ala Glu
385                 390                 395                 400
Ile Gly Lys Asn Lys Thr Pro His Val Ser Val Cys Gly Asp Val Lys
                405                 410                 415
Leu Ala Leu Gln Gly Met Asn Lys Val Leu Glu Asn Arg Ala Glu Glu
            420                 425                 430
Leu Lys Leu Asp Phe Gly Val Trp Arg Asn Glu Leu Asn Val Gln Lys
            435                 440                 445
```

```
Gln Lys Phe Pro Leu Ser Phe Lys Thr Phe Gly Glu Ala Ile Pro Pro
    450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
                485                 490                 495

Asn Tyr Lys Lys Pro Arg Gln Trp Leu Ser Ser Gly Gly Leu Gly Ala
            500                 505                 510

Met Gly Phe Gly Leu Pro Ala Ala Ile Gly Ala Ser Val Ala Asn Pro
            515                 520                 525

Asp Ala Ile Val Val Asp Ile Asp Gly Asp Gly Ser Phe Ile Met Asn
    530                 535                 540

Val Gln Glu Leu Ala Thr Ile Arg Val Glu Asn Leu Pro Val Lys Val
545                 550                 555                 560

Leu Leu Leu Asn Asn Gln His Leu Gly Met Val Met Gln Trp Gln Asp
                565                 570                 575

Arg Phe Tyr Lys Ala Asn Arg Ala His Thr Phe Leu Gly Asp Pro Ala
            580                 585                 590

Gln Glu Asp Glu Ile Phe Pro Asn Met Leu Leu Phe Ala Ala Ala Cys
            595                 600                 605

Gly Ile Pro Ala Ala Arg Val Thr Lys Lys Ala Asp Leu Arg Glu Ala
            610                 615                 620

Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Ser Gly Gly Thr
            645                 650                 655

Phe Asn Asp Val Ile Thr Glu Gly Asp Gly Arg Ile Lys Tyr
            660                 665                 670
```